US011969541B2

(12) United States Patent
Gordon et al.

(10) Patent No.: US 11,969,541 B2
(45) Date of Patent: *Apr. 30, 2024

(54) SYSTEMS AND METHODS FOR CONTROLLING OPERATION OF NEGATIVE PRESSURE WOUND THERAPY APPARATUS

(71) Applicant: Smith & Nephew PLC, Watford (GB)

(72) Inventors: Benjamin Gordon, Cambridge (GB); Jake Turner, Cambridge (GB); Edward Yerbury Hartwell, Heslington (GB); Stephen Jacob, Fenstanton (GB); Nathan Wrench, Cambridge (GB); Edward Vernon-Harcourt, Steyning (GB); David Harris, Milton (GB)

(73) Assignee: Smith & Nephew PLC, Watford (GB)

( * ) Notice: Subject to any disclaimer, the term of this patent is extended or adjusted under 35 U.S.C. 154(b) by 1232 days.

This patent is subject to a terminal disclaimer.

(21) Appl. No.: 16/443,749

(22) Filed: Jun. 17, 2019

(65) Prior Publication Data

US 2020/0000983 A1  Jan. 2, 2020

Related U.S. Application Data

(60) Continuation of application No. 15/228,987, filed on Aug. 4, 2016, now Pat. No. 10,328,187, which is a
(Continued)

(30) Foreign Application Priority Data

Jul. 2, 2007 (GB) ....................................... 0712736
Jul. 2, 2007 (GB) ....................................... 0712757
(Continued)

(51) Int. Cl.
*A61M 1/00* (2006.01)
*A61F 13/00* (2006.01)
(Continued)

(52) U.S. Cl.
CPC ................ *A61M 1/78* (2021.05); *A61M 1/60* (2021.05); *A61M 1/784* (2021.05); *A61M 1/96* (2021.05);
(Continued)

(58) Field of Classification Search
CPC .......... A61M 1/00; A61M 5/178; A61M 5/00; A61M 35/00; A61M 1/78; A61M 1/60;
(Continued)

(56) References Cited

U.S. PATENT DOCUMENTS 3,568,675 A   3/1971  Harvey
3,599,639 A   8/1971  Spotz
(Continued)

FOREIGN PATENT DOCUMENTS

CA   2 198 243   2/1996
CA   2 551 340   5/1997
(Continued)

OTHER PUBLICATIONS

Communication of the Registry—Opponents Reply to the Appeal for European Patent No. 2985044, dated Jan. 22, 2021, 25 pages.
(Continued)

*Primary Examiner* — Susan S Su
(74) *Attorney, Agent, or Firm* — Knobbe, Martens, Olson & Bear, LLP

(57) ABSTRACT

Methods and apparatuses for detecting full waste canister and/or fluid flow path blockage conditions are disclosed. Also disclosed are methods and apparatuses for controlling a pump. In some embodiments, flow of fluid can be restricted in a portion of the fluid flow path. A controller can be configured to compare a difference in pressure values upstream and downstream of a fluid flow restrictor to a pressure difference threshold, and determine based on the comparison whether to activate an alarm indicating the full
(Continued)

waste canister condition or the fluid flow path blockage condition. The controller can be additionally or alternatively configured to determine a fluid flow using a flow meter, open a selectable valve in response to a comparison of the fluid flow with a fluid flow threshold, determine fluid flow after opening the valve, and determine based on the fluid flow after opening the valve whether to activate the alarm.

20 Claims, 26 Drawing Sheets

Related U.S. Application Data division of application No. 13/589,021, filed on Aug. 17, 2012, now Pat. No. 9,408,954, which is a continuation-in-part of application No. 12/667,228, filed as application No. PCT/GB2008/050507 on Jun. 27, 2008, now abandoned, said application No. 13/589,021 is a continuation-in-part of application No. 12/667,231, filed as application No. PCT/GB2008/002118 on Jun. 20, 2008, now Pat. No. 8,494,349, said application No. 13/589,021 is a continuation-in-part of application No. 12/667,326, filed as application No. PCT/GB2008/002112 on Jun. 20, 2008, now Pat. No. 8,444,392, said application No. 13/589,021 is a continuation-in-part of application No. 12/672,055, filed as application No. PCT/GB2008/050511 on Jun. 27, 2008, now Pat. No. 8,974,429, said application No. 13/589,021 is a continuation-in-part of application No. 12/672,063, filed as application No. PCT/GB2008/002101 on Jun. 20, 2008, now abandoned, said application No. 13/589,021 is a continuation-in-part of application No. 12/672,065, filed as application No. PCT/GB2008/002099 on Jun. 20, 2008, now abandoned, said application No. 13/589,021 is a continuation-in-part of application No. 12/672,490, filed as application No. PCT/GB2008/002349 on Jul. 9, 2008, now abandoned, said application No. 13/589,021 is a continuation-in-part of application No. 12/672,468, filed as application No. PCT/GB2008/002346 on Jul. 9, 2008, now Pat. No. 8,843,327, said application No. 13/589,021 is a continuation-in-part of application No. 12/672,472, filed as application No. PCT/GB2008/050515 on Jun. 27, 2008, now abandoned.

(30) Foreign Application Priority Data

| | | | |
|---|---|---|---|
| Jul. 2, 2007 | (GB) | .................. | 0712759 |
| Aug. 6, 2007 | (GB) | .................. | 0715210 |
| Aug. 6, 2007 | (GB) | .................. | 0715211 |
| Aug. 6, 2007 | (GB) | .................. | 0715259 |
| Aug. 6, 2007 | (GB) | .................. | 0715263 |
| Aug. 6, 2007 | (GB) | .................. | 0715264 |
| Aug. 6, 2007 | (GB) | .................. | 0715276 |

(51) Int. Cl.

| | |
|---|---|
| A61F 13/02 | (2006.01) |
| A61M 5/00 | (2006.01) |
| A61M 5/178 | (2006.01) |
| A61M 35/00 | (2006.01) |

(52) U.S. Cl.

CPC ............ *A61M 1/962* (2021.05); *A61M 1/982* (2021.05); *A61M 1/984* (2021.05); *A61M 2205/15* (2013.01); *A61M 2205/18* (2013.01); *A61M 2205/3331* (2013.01); *A61M 2205/3334* (2013.01); *A61M 2205/3365* (2013.01); *A61M 2205/50* (2013.01); *A61M 2205/502* (2013.01); *A61M 2205/7536* (2013.01); *A61M 2205/8206* (2013.01); *A61M 2209/088* (2013.01)

(58) Field of Classification Search

CPC ........ A61M 1/96; A61M 1/962; A61M 1/982; A61M 1/984; A61M 2205/15; A61M 2205/18; A61M 2205/3331; A61M 2205/3334; A61M 2205/3365; A61M 2205/50; A61M 2205/502; A61M 2205/7536; A61M 2205/8206; A61M 2209/088; A61M 2205/42; A61F 13/00; A61F 13/02

See application file for complete search history.

(56) References Cited

U.S. PATENT DOCUMENTS

| | | |
|---|---|---|
| 3,882,861 A | 5/1975 | Kettering et al. |
| 4,080,966 A | 3/1978 | McNally et al. |
| 4,090,966 A | 5/1978 | Clendenen |
| 4,180,074 A | 12/1979 | Murry et al. |
| 4,291,260 A | 9/1981 | Nixon |
| 4,316,466 A | 2/1982 | Babb |
| 4,382,441 A | 5/1983 | Svedman |
| 4,468,219 A | 8/1984 | George et al. |
| 4,708,010 A | 11/1987 | Sgourakes |
| 4,710,165 A | 12/1987 | McNeil et al. |
| 4,740,202 A | 4/1988 | Stacey |
| 4,795,448 A | 1/1989 | Stacey et al. |
| 4,930,997 A | 6/1990 | Bennett |
| 4,936,832 A | 6/1990 | Vaillancourt |
| 4,936,834 A | 6/1990 | Beck et al. |
| 4,957,107 A | 9/1990 | Sipin |
| 4,969,880 A | 11/1990 | Zamierowski |
| 4,979,944 A | 12/1990 | Luzsicza |
| 5,002,539 A | 3/1991 | Coble |
| 5,149,331 A | 9/1992 | Ferdman et al. |
| 5,356,378 A | 10/1994 | Doan |
| 5,419,768 A | 5/1995 | Kayser |
| 5,429,601 A | 7/1995 | Conley et al. |
| 5,449,347 A | 9/1995 | Preen et al. |
| 5,454,700 A | 10/1995 | Iguchi et al. |
| 5,549,584 A | 8/1996 | Gross |
| 5,549,585 A | 8/1996 | Maher et al. |
| 5,575,762 A | 11/1996 | Peeler et al. |
| 5,630,855 A | 5/1997 | Lundback |
| 5,636,643 A | 6/1997 | Argenta et al. |
| 5,637,093 A | 6/1997 | Hyman et al. |
| 5,645,081 A | 7/1997 | Argenta et al. |
| 5,690,831 A | 11/1997 | Kenley et al. |
| 5,744,027 A | 4/1998 | Connell et al. |
| 5,760,754 A | 6/1998 | Amero, Jr. et al. |
| 5,782,608 A | 7/1998 | McKee |
| 5,844,137 A | 12/1998 | Carson |
| 5,951,502 A | 9/1999 | Peeler et al. |
| 5,951,863 A | 9/1999 | Kruger et al. |
| 5,988,842 A | 11/1999 | Johnsen et al. |
| 6,053,196 A | 4/2000 | Kortge |
| 6,129,440 A | 10/2000 | Reynolds |
| 6,135,116 A | 10/2000 | Vogel et al. |
| 6,142,982 A | 11/2000 | Hunt et al. |
| 6,159,160 A | 12/2000 | Hsei et al. |
| 6,229,286 B1 | 5/2001 | Tokuyama |
| 6,354,805 B1 | 3/2002 | Moller |
| 6,368,311 B1 | 4/2002 | Valerio |
| 6,387,086 B2 | 5/2002 | Mathias et al. |
| 6,443,983 B1 | 9/2002 | Nagyszalanczy et al. |
| 6,458,109 B1 | 10/2002 | Henley et al. |
| 6,468,042 B2 | 10/2002 | Moller |
| 6,503,219 B2 | 1/2003 | Milsom |
| 6,558,340 B1 | 5/2003 | Traeger |
| 6,585,675 B1 | 7/2003 | O'Mahony et al. |
| 6,602,468 B2 | 8/2003 | Patterson et al. |

(56) References Cited

U.S. PATENT DOCUMENTS

| | | | |
|---|---|---|---|
| 6,620,379 B1 | 9/2003 | Pluk et al. |
| 6,691,047 B1 | 2/2004 | Fredricks |
| 6,692,132 B1 | 2/2004 | Meeker |
| 6,695,823 B1 | 2/2004 | Lina et al. |
| 6,703,807 B2 | 3/2004 | Sakata et al. |
| 6,725,731 B2 * | 4/2004 | Wiklund ............. F15B 15/2838 |
| | | | 73/861.58 |
| 6,755,807 B2 | 6/2004 | Risk et al. |
| 6,764,462 B2 | 7/2004 | Risk, Jr. et al. |
| 6,786,879 B1 | 9/2004 | Bolam et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,868,739 B1 | 3/2005 | Krivitski et al. |
| 6,916,424 B2 | 7/2005 | Collins et al. |
| 6,951,553 B2 | 10/2005 | Bubb et al. |
| 6,988,423 B2 | 1/2006 | Bolam et al. |
| 7,004,915 B2 | 2/2006 | Boynton et al. |
| 7,004,923 B2 | 2/2006 | Deniega et al. |
| 7,022,113 B2 | 4/2006 | Lockwood et al. |
| 7,042,180 B2 | 5/2006 | Terry et al. |
| 7,092,797 B2 | 8/2006 | Gaines et al. |
| 7,108,683 B2 | 9/2006 | Zamierowski |
| 7,128,735 B2 | 10/2006 | Weston |
| 7,160,273 B2 | 1/2007 | Greter et al. |
| 7,195,624 B2 * | 3/2007 | Lockwood ............... A61M 1/90 |
| | | | 604/315 |
| 7,214,202 B1 | 5/2007 | Vogel et al. |
| 7,216,651 B2 | 5/2007 | Argenta et al. |
| 7,278,981 B2 | 10/2007 | Ellingboe et al. |
| 7,438,705 B2 | 10/2008 | Karpowicz et al. |
| 7,494,482 B2 | 2/2009 | Orgill et al. |
| 7,503,910 B2 | 3/2009 | Adahan |
| 7,553,306 B1 | 6/2009 | Hunt et al. |
| 7,611,500 B1 | 11/2009 | Lina et al. |
| 7,612,247 B2 | 11/2009 | Oyaski |
| 7,615,158 B2 | 11/2009 | Sternby et al. |
| 7,625,362 B2 | 12/2009 | Boehringer et al. |
| 7,666,171 B2 | 2/2010 | Mombrinie et al. |
| 7,670,323 B2 | 3/2010 | Hunt et al. |
| 7,678,090 B2 | 3/2010 | Risk, Jr. |
| 7,708,724 B2 | 5/2010 | Weston |
| 7,723,560 B2 | 5/2010 | Lockwood et al. |
| 7,744,066 B2 | 6/2010 | Williams |
| 7,744,553 B2 | 6/2010 | Kelly et al. |
| 7,763,000 B2 | 7/2010 | Risk, Jr. et al. |
| 7,776,001 B2 | 8/2010 | Brugger et al. |
| 7,776,028 B2 | 8/2010 | Miller et al. |
| 7,790,945 B1 | 9/2010 | Watson, Jr. |
| 7,811,269 B2 | 10/2010 | Boynton et al. |
| 7,837,673 B2 | 11/2010 | Vogel |
| 7,846,141 B2 | 12/2010 | Weston |
| 7,857,806 B2 | 12/2010 | Karpowicz et al. |
| 7,883,494 B2 | 2/2011 | Martin |
| 7,909,805 B2 | 3/2011 | Weston |
| 7,927,319 B2 | 4/2011 | Lawhorn |
| 7,998,125 B2 | 8/2011 | Weston |
| 8,062,272 B2 | 11/2011 | Weston |
| 8,100,887 B2 | 1/2012 | Weston et al. |
| 8,105,295 B2 | 1/2012 | Blott et al. |
| 8,162,909 B2 | 4/2012 | Blott et al. |
| 8,167,869 B2 | 5/2012 | Wudyka |
| 8,192,409 B2 | 6/2012 | Hardman et al. |
| 8,235,939 B2 | 8/2012 | Johnson et al. |
| 8,282,611 B2 | 10/2012 | Weston |
| 8,294,586 B2 | 10/2012 | Pidgeon et al. |
| 8,298,200 B2 | 10/2012 | Vess et al. |
| 8,308,714 B2 | 11/2012 | Weston et al. |
| 8,323,264 B2 | 12/2012 | Weston et al. |
| 8,333,744 B2 | 12/2012 | Hartwell et al. |
| 8,353,857 B2 | 1/2013 | Rosenberg |
| 8,366,692 B2 | 2/2013 | Weston |
| 8,377,016 B2 | 2/2013 | Argenta et al. |
| 8,444,392 B2 | 5/2013 | Turner et al. |
| 8,449,487 B2 | 5/2013 | Hovland et al. |
| 8,449,508 B2 | 5/2013 | Coulthard et al. |
| 8,494,349 B2 | 7/2013 | Gordon |
| 8,529,487 B2 | 9/2013 | Fava et al. |
| 8,551,061 B2 | 10/2013 | Hartwell |
| 8,617,129 B2 | 12/2013 | Hartwell |
| 8,622,981 B2 | 1/2014 | Hartwell et al. |
| 8,663,200 B2 | 3/2014 | Weston et al. |
| 8,715,256 B2 | 5/2014 | Greener |
| 8,734,425 B2 | 5/2014 | Nicolini |
| 8,771,259 B2 | 7/2014 | Karpowicz et al. |
| 8,785,059 B2 | 7/2014 | Hartwell |
| 8,814,841 B2 | 8/2014 | Hartwell |
| 8,814,842 B2 | 8/2014 | Coulthard et al. |
| 8,834,451 B2 | 9/2014 | Blott et al. |
| 8,843,327 B2 | 9/2014 | Vernon-Harcourt et al. |
| 8,845,603 B2 | 9/2014 | Middleton et al. |
| 8,852,149 B2 | 10/2014 | Weston et al. |
| 8,852,170 B2 | 10/2014 | Weston et al. |
| 8,905,985 B2 | 12/2014 | Allen et al. |
| 8,945,074 B2 | 2/2015 | Buan et al. |
| 8,951,235 B2 | 2/2015 | Allen et al. |
| 8,974,429 B2 | 3/2015 | Gordon et al. |
| 9,067,003 B2 | 6/2015 | Buan et al. |
| 9,084,845 B2 | 7/2015 | Adie et al. |
| 9,180,231 B2 | 11/2015 | Greener |
| 9,199,011 B2 | 12/2015 | Locke et al. |
| 9,205,183 B2 | 12/2015 | Hartwell et al. |
| 9,227,000 B2 | 1/2016 | Fink et al. |
| 9,314,557 B2 | 4/2016 | Ricci et al. |
| 9,421,309 B2 | 8/2016 | Robinson et al. |
| 9,427,505 B2 | 8/2016 | Askem et al. |
| 9,452,244 B2 | 9/2016 | Blott et al. |
| 9,526,817 B2 | 12/2016 | Blott et al. |
| 9,636,440 B2 | 5/2017 | Weston et al. |
| 9,642,950 B2 | 5/2017 | Hartwell |
| 10,328,187 B2 | 6/2019 | Gordon et al. |
| 2002/0156464 A1 | 10/2002 | Blischak et al. |
| 2002/0183702 A1 | 12/2002 | Henley et al. |
| 2002/0198504 A1 | 12/2002 | Risk et al. |
| 2003/0040687 A1 | 2/2003 | Boynton et al. |
| 2003/0097100 A1 | 5/2003 | Watson |
| 2003/0235635 A1 | 12/2003 | Fong et al. |
| 2004/0006319 A1 | 1/2004 | Lina et al. |
| 2004/0153029 A1 | 8/2004 | Blischak et al. |
| 2004/0167482 A1 | 8/2004 | Watson |
| 2004/0260429 A1 | 12/2004 | Saelens |
| 2005/0067191 A1 | 3/2005 | Miyamoto et al. |
| 2005/0166683 A1 | 8/2005 | Krivitski et al. |
| 2006/0059980 A1 | 3/2006 | Matsubara et al. |
| 2006/0129137 A1 | 6/2006 | Lockwood et al. |
| 2006/0167607 A1 | 7/2006 | Nakamura et al. |
| 2006/0198503 A1 | 9/2006 | Wahl et al. |
| 2007/0014837 A1 | 1/2007 | Johnson et al. |
| 2007/0016152 A1 | 1/2007 | Karpowicz et al. |
| 2007/0032763 A1 | 2/2007 | Vogel |
| 2007/0055209 A1 | 3/2007 | Patel et al. |
| 2007/0078370 A1 | 4/2007 | Shener et al. |
| 2007/0118096 A1 | 5/2007 | Smith et al. |
| 2007/0129660 A1 | 6/2007 | McLeod et al. |
| 2007/0154319 A1 | 7/2007 | Stiles, Jr. et al. |
| 2007/0156104 A1 | 7/2007 | Lockwood et al. |
| 2007/0179460 A1 | 8/2007 | Adahan |
| 2007/0219497 A1 | 9/2007 | Johnson et al. |
| 2007/0219532 A1 | 9/2007 | Karpowicz et al. |
| 2008/0071216 A1 | 3/2008 | Locke et al. |
| 2008/0071234 A1 | 3/2008 | Kelch et al. |
| 2008/0071235 A1 | 3/2008 | Locke et al. |
| 2008/0139674 A1 | 6/2008 | Archambeau et al. |
| 2008/0200906 A1 | 8/2008 | Sanders et al. |
| 2008/0234641 A1 | 9/2008 | Locke et al. |
| 2008/0281281 A1 | 11/2008 | Meyer et al. |
| 2008/0300578 A1 | 12/2008 | Freedman |
| 2009/0012441 A1 | 1/2009 | Mulligan |
| 2009/0030402 A1 | 1/2009 | Adahan |
| 2009/0105670 A1 | 4/2009 | Bentley et al. |
| 2009/0163882 A1 | 6/2009 | Koch et al. |
| 2009/0299255 A1 | 12/2009 | Kazala, Jr. et al. |
| 2009/0299306 A1 | 12/2009 | Buan |
| 2009/0306630 A1 | 12/2009 | Locke et al. |

(56) References Cited

U.S. PATENT DOCUMENTS

| | | |
|---|---|---|
| 2010/0036367 A1 | 2/2010 | Krohn |
| 2010/0125259 A1 | 5/2010 | Olson |
| 2010/0174270 A1 | 7/2010 | Charlez et al. |
| 2010/0211030 A1 | 8/2010 | Turner et al. |
| 2010/0249691 A1 | 9/2010 | Van Der Mooren et al. |
| 2011/0015593 A1 | 1/2011 | Svedman et al. |
| 2011/0028921 A1 | 2/2011 | Hartwell et al. |
| 2011/0054810 A1 | 3/2011 | Turner |
| 2011/0063117 A1 | 3/2011 | Turner |
| 2011/0077605 A1 | 3/2011 | Karpowicz et al. |
| 2011/0236460 A1 | 9/2011 | Stopek et al. |
| 2011/0251569 A1 | 10/2011 | Turner et al. |
| 2012/0001762 A1 | 1/2012 | Turner et al. |
| 2012/0111963 A1 | 5/2012 | Gordon et al. |
| 2013/0144227 A1 | 6/2013 | Locke et al. |
| 2013/0150813 A1 | 6/2013 | Gordon et al. |
| 2013/0296816 A1 | 11/2013 | Greener |
| 2014/0352407 A1 | 12/2014 | Vernon-Harcourt et al. |
| 2015/0051560 A1 | 2/2015 | Askem |

FOREIGN PATENT DOCUMENTS

| | | |
|---|---|---|
| CA | 2 349 638 | 5/2000 |
| CA | 2 458 285 | 3/2003 |
| CA | 2 483 654 | 11/2003 |
| CA | 2 237 606 | 8/2006 |
| DE | 1 963 258 | 6/1971 |
| DE | 4 016 034 | 11/1991 |
| DE | 195 17 699 | 11/1996 |
| DE | 10 2005 014 420 | 9/2006 |
| EP | 0 194 198 A2 | 9/1986 |
| EP | 0 669 463 | 8/1995 |
| EP | 0 853 950 | 7/1998 |
| EP | 0 777 504 | 10/1998 |
| EP | 1 088 569 A2 | 4/2001 |
| EP | 1 393 767 | 3/2004 |
| EP | 1 608 032 | 12/2005 |
| EP | 1 897 569 | 3/2008 |
| EP | 2 699 278 | 2/2014 |
| FR | 1 163 907 | 10/1958 |
| GB | 1334840 | 10/1973 |
| GB | 2047438 | 11/1980 |
| GB | 2235877 | 3/1991 |
| GB | 2307180 | 5/1997 |
| GB | 2336546 | 10/1999 |
| GB | 2342584 | 4/2000 |
| GB | 2356148 | 5/2001 |
| GB | 2378734 | 2/2003 |
| GB | 2418738 | 4/2006 |
| WO | WO 1996/005873 | 2/1996 |
| WO | WO 1997/018007 | 5/1997 |
| WO | WO 2000/017968 | 3/2000 |
| WO | WO 2000/021586 | 4/2000 |
| WO | WO 2000/061206 | 10/2000 |
| WO | WO 2001/005023 | 1/2001 |
| WO | WO 2001/037922 A2 | 5/2001 |
| WO | WO 2001/037922 A3 | 5/2001 |
| WO | WO 2001/072352 | 10/2001 |
| WO | WO 2002/019928 | 3/2002 |
| WO | WO 2003/005943 | 1/2003 |
| WO | WO 2003/022333 | 3/2003 |
| WO | WO 2003/030966 | 4/2003 |
| WO | WO 2003/053346 | 7/2003 |
| WO | WO 2003/092620 | 11/2003 |
| WO | WO 2003/101508 | 12/2003 |
| WO | WO 2004/037334 | 5/2004 |
| WO | WO 2005/004670 | 1/2005 |
| WO | WO 2005/006975 | 1/2005 |
| WO | WO 2005/046760 | 5/2005 |
| WO | WO 2005/105180 | 11/2005 |
| WO | WO 2005/115497 | 12/2005 |
| WO | WO 2006/052745 | 5/2006 |
| WO | WO 2006/100053 | 9/2006 |
| WO | WO 2006/105892 | 10/2006 |
| WO | WO 2006/114638 | 11/2006 |
| WO | WO 2006/135934 | 12/2006 |
| WO | WO 2007/013064 | 2/2007 |
| WO | WO 2007/019038 | 2/2007 |
| WO | WO 2007/030599 | 3/2007 |
| WO | WO 2007/030601 | 3/2007 |
| WO | WO 2007/062024 | 5/2007 |
| WO | WO 2007/070570 | 6/2007 |
| WO | WO 2007/087808 | 8/2007 |
| WO | WO 2007/087809 | 8/2007 |
| WO | WO 2007/088530 | 8/2007 |
| WO | WO 2007/133618 | 11/2007 |
| WO | WO 2008/010094 | 1/2008 |
| WO | WO 2008/030872 | 3/2008 |
| WO | WO 2008/036360 | 3/2008 |
| WO | WO 2008/036361 | 3/2008 |
| WO | WO 2008/039223 | 4/2008 |
| WO | WO 2008/039314 | 4/2008 |
| WO | WO 2008/048481 | 4/2008 |
| WO | WO 2008/049029 | 4/2008 |
| WO | WO 2009/004288 | 1/2009 |
| WO | WO 2009/004291 | 1/2009 |
| WO | WO 2009/019415 | 2/2009 |
| WO | WO 2009/019419 | 2/2009 |
| WO | WO 2009/019495 | 2/2009 |
| WO | WO 2009/019496 | 2/2009 |
| WO | WO 2009/077722 | 6/2009 |
| WO | WO 2009/089390 | 7/2009 |

OTHER PUBLICATIONS

Decision revoking the European Patent (Art. 101 (3)(b) EPC) for European Patent No. 2985044, mailed on Apr. 30, 2020, 28 pages.
International Search Report for Application No. PCT/GB2008/002099 dated Mar. 12, 2009, 4 pages.
KCI, Inc., "Acti V.A.C. Therapy System," User Manual, Sep. 2007, 64 pages.
KCI, "V.A.C. User Manual," The Clinical Advantage, 2003, 20 pages.
Notice of Appeal on behalf of Patentee for European Patent No. 2985044 mailed on Jul. 9, 2020, 2 pages.
Opponent Arguments for European Patent No. 2985044, mailed Jan. 3, 2020, 2 pages.
Oral Proceedings of Revocation for European Patent No. 2985044, dated Mar. 5, 2020, 9 pages.
Patent Proprietor Arguments for European Patent No. 2985044, mailed Jan. 3, 2020, 2 pages.
Proprietor's Statement of Grounds of Appeal for European Patent No. 2985044, dated Sep. 10, 2020, 7 pages.
Provisional Non-Binding Opinion of the Opposition Division, re the Opposition of European Patent No. EP 2 985 044, dated Aug. 21, 2019, in 7 pages.
Notice of Opposition—Statement of Facts and Evidence, re European Patent No. EP 2 985 044, dated Dec. 14, 2018, in 22 pages.
Opponent's Written Submission in Preparation for the Oral Proceedings, re the Opposition of European Patent No. EP 2 175 908, dated Sep. 21, 2018, in 43 pages.
Preparation for Oral Proceedings, re European Patent No. 2 175 906, dated Jun. 27, 2017, in 16 pages.
Reply of the Patent Proprietor to the Notice of Opposition, re European Patent No. EP 2 175 906, dated Mar. 24, 2017, in 26 pages.
Reply of the Patent Proprietor to the Notice(s) of Opposition, re the Opposition of European Patent No. 2 985 044, dated May 13, 2019, in 13 pages.
U.S. Appl. No. 10/599,720, filed Oct. 6, 2006, Blott et al.
U.S. Appl. No. 12/192,000, filed Aug. 14, 2008, Hartwell et al.
U.S. Appl. No. 15/851,020, filed Dec. 21, 2017, Vernon-Harcourt et al.
Bagautdinov, N.A., "Variant of External Vacuum Aspiration in the Treatment of Purulent Diseases of Soft Tissues", Current Problems in Modern Clinical Surgery—Interdepartmental Collection, edited by V. Ye. Volkov et al. (Chuvash State University, Cheboksary, USSR 1986), pp. 94-96, in 8 pages.

(56) References Cited

OTHER PUBLICATIONS

British Pump Manufacturers Association et al., "Variable Speed Driven Pumps: Best Practice Guide", published online Aug. 1, 2003 (retrieved Mar. 22, 2013), in 48 pages. URL: http://www.gambia.org.uk/web_images/documents/publications/GAMBICA_VSD_Pumps_Best_Practice_Guide.pdf.
Canadian Office Action, re CA App. No. 2,695,409, dated Aug. 15, 2014.
Canadian Office Action, re CA Application No. 2,695,409, dated Jun. 3, 2015.
Canadian Office Action, re CA Application No. 2,695,409, dated Apr. 28, 2016.
Canadian Office Action, re CA Application No. 2,948,629, dated Apr. 30, 2018.
European Office Action, dated Apr. 21, 2015, re EPO App. No. 08 762 428.4.
European Office Action, re EP Application No. 08 762 613.1, dated Dec. 16, 2015.
European Office Action, re EP Application No. 08 762 418.5, dated May 4, 2015.
European Office Action, re EP Application No. 08 775 893.4, dated Jun. 25, 2012.
European Office Action, re EP Application No. 08775 890.0, dated Jan. 10, 2014.
European Office Action, re EP Application No. 15183456.1, dated Dec. 23, 2015.
European Office Action, re EP Application No. 18153512.1, dated May 9, 2018.
European Office Action, re EP Application No. 08762609.9, dated Jul. 16, 2010.
Hicks, T., "Mechanical Engineering Formulas Pocket Guide", McGraw-Hill, Feb. 2003, in 4 pages.
Info V.A.C. User Manual—KCI—Dec. 2006, in 76 pages.
International Search Report, re PCT Application No. PCT/GB2008/050507, dated Oct. 15, 2008.
International Preliminary Report on Patentability, re PCT Application No. PCT/GB2008/050507, dated Jan. 5, 2010.
International Preliminary Report on Patentability, re PCT Application No. PCT/GB2008/002118, dated Jan. 5, 2010.
International Search Report, re PCT Application No. PCT/GB2008/002118, dated Mar. 12, 2009.
International Written Opinion from PCT/GB2008/002118 dated Mar. 12, 2009 in 6 pages.
International Search Report, re PCT Application No. PCT/GB2008/002112, dated Feb. 18, 2009.
International Preliminary Report on Patentability, re PCT Application No. PCT/GB2008/002112, dated Jan. 5, 2010.
International Preliminary Report on Patentability re PCT/GB2008/050511, dated Feb. 9, 2010 in 6 pages.
International Search Report and Written Opinion, re PCT Application No. PCT/GB2008/050511, dated Oct. 31, 2008.
International Search Report, re PCT Application No. PCT/GB2008/002101, dated Mar. 12, 2009.
International Written Opinion, re PCT Application No. PCT/GB2008/002101, dated Mar. 12, 2009.
International Preliminary Report on Patentability, re PCT Application No. PCT/GB2008/002101, dated Feb. 9, 2010.
International Search Report, re PCT Application No. PCT/GB2008/002099, dated Dec. 3, 2009.
International Written Opinion, re PCT Application No. PCT/GB2008/002099, dated Dec. 3, 2009.
International Preliminary Report on Patentability, re PCT Application No. PCT/GB2008/002099, dated Feb. 9, 2010.
International Search Report and Written Opinion, re PCT Application No. PCT/GB2008/002349, dated Oct. 31, 2008.
International Preliminary Report on Patentability, re PCT Application PCT/GB2008/002349, dated Feb. 9, 2010.
International Search Report, re PCT Application No. PCT/GB2008/050507, dated Oct. 31, 2008.
International Preliminary Report on Patentability, re PCT Application No. PCT/GB2008/002346, dated Feb. 9, 2010.
International Search Report, re PCT Application No. PCT/GB2008/002346, dated Oct. 27, 2008.
International Search Report, re PCT Application No. PCT/GB2008/050515, dated Apr. 6, 2009.
International Preliminary Report on Patentability, re PCT Application No. PCT/GB2008/050515, dated Feb. 9, 2010.
International Invitation to Pay and Partial Search Report, re PCT Application No. PCT/US2014/050233, dated Nov. 5, 2014.
International Search Report and Written Opinion, re PCT Application No. PCT/US2014/050233, dated Jan. 7, 2015.
International Preliminary Report on Patentability, re PCT Application No. PCT/US2007/021790, dated Apr. 23, 2009.
International Search Report and Written Opinion, re PCT Application No. PCT/US2007/021790, dated Jul. 21, 2008.
Jeter, K. et al., "Managing Draining Wounds and Fistulae: New and Established Methods", Chronic Wound Care, 1990, pp. 240-246, in 7 pages.
Landis, E.M. et al., The Effects of Alternate Suction and Pressure on Blood Flow to the Lower Extremities, Alternate Suction and Pressure, J Clin Invest. Sep. 1933, vol. 12(5), pp. 925-961.
Notice of Opposition—Statement of Facts and Evidence, re European Patent No. EP 2 175 906, dated Oct. 13, 2016, in 14 pages.
Notice of Opposition—Statement of Facts and Evidence, re European Patent No. EP 2 175 908, dated May 17, 2017, in 8 pages.
Nursing75, "Wound Suction: Better Drainage with Fewer Problems", Nursing, vol. 5, No. 10, Oct. 1975, pp. 52-55, in 4 pages.
Preliminary and Non-binding Opinion of the Opposition Division, re European Patent No. EP 2 175 908, dated Mar. 13, 2018, in 6 pages.
Reply of the Patent Proprietor to the Notice of Opposition, re European Patent No. EP 2 175 908, dated Nov. 2, 2017, in 5 pages.
Response to Jul. 16, 2010 European Office Action from European Patent Application No. 08762609.9.
Sadasivan, N. et al., "Studies on Frequency and Magnitude of Fluctuations of Pressure Drop in Gas-Solid Fluidised Beds", Power Technology, vol. 26, May-Jun. 1980, in 8 pages.
US Medco Healthcare, Healing through Technology, HYPOwound Therapy System, downloaded from internet Apr. 18, 2006, in 8 pages. URL: http://www.usmedco.net.
International Written Opinion, re PCT Application No. PCT/GB2008/050507, dated Jan. 2, 2010.
International Written Opinion from PCT/GB2008/050507, dated Oct. 15, 2008.
International Written Opinion, re PCT Application No. PCT/GB2008/002112, dated Feb. 18, 2009.
International Written Opinion, re PCT Application No. 6, 2010.
International Written Opinion, re PCT Application No. PCT/GB2008/050515, dated Feb. 6, 2010.
Communication of the Board of Appeal Pursuant to Article 15(1) for European Patent No. 2985044, mailed Nov. 9, 2023, 11 pages.
Forwarding of Submissions to Parties of a Letter of the Patent Proprietor for European Patent No. 2985044, dated Dec. 10, 2023, mailed on Dec. 14, 2023, 14 pages.

\* cited by examiner

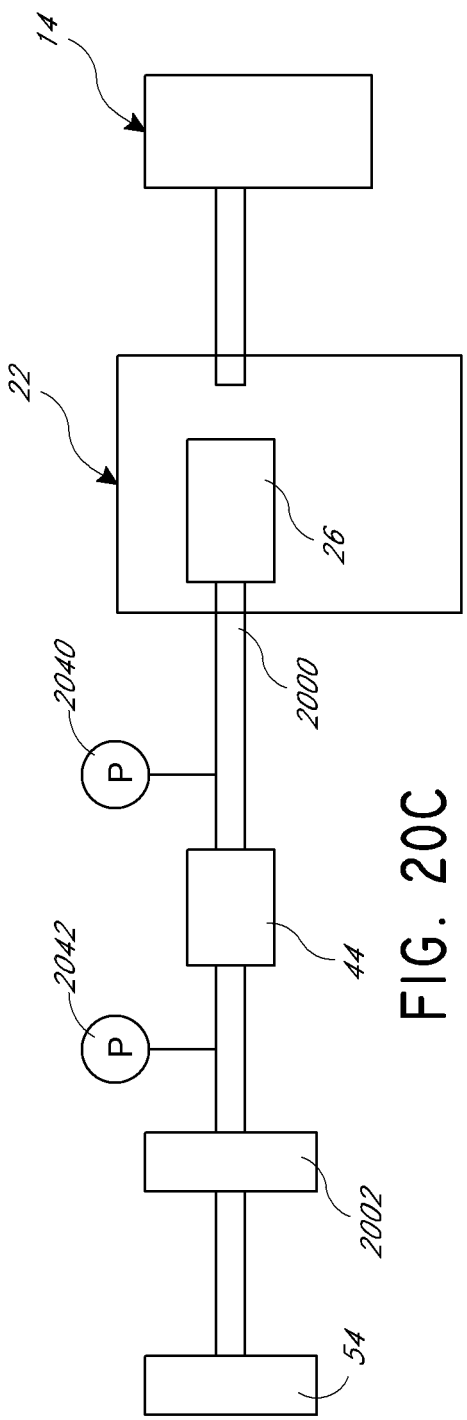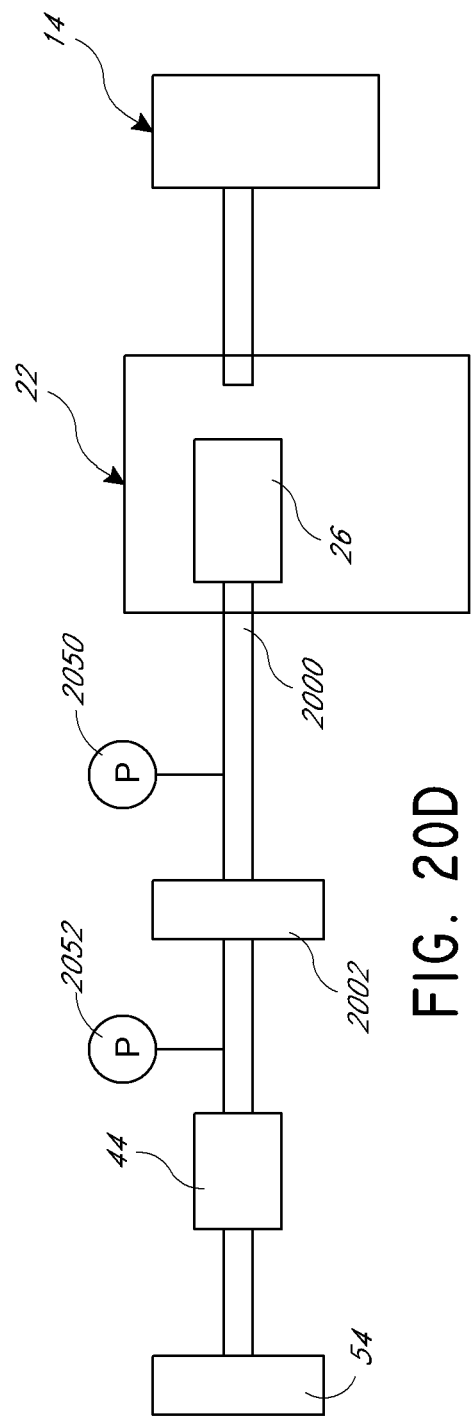

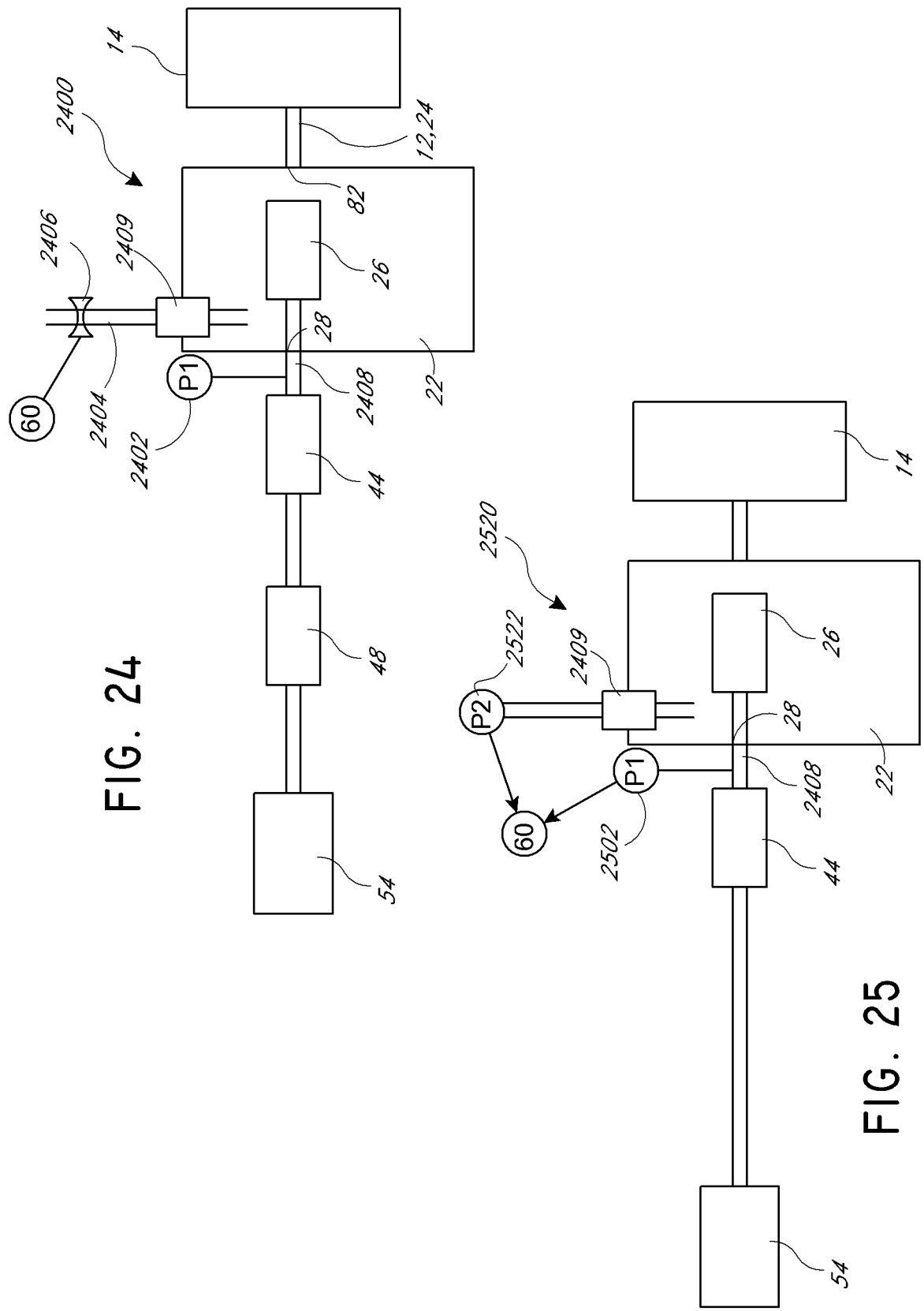

SYSTEMS AND METHODS FOR CONTROLLING OPERATION OF NEGATIVE PRESSURE WOUND THERAPY APPARATUS

CROSS-REFERENCE TO RELATED APPLICATIONS

This application is a continuation of U.S. application Ser. No. 15/228,987, filed Aug. 4, 2016, which is a divisional of U.S. application Ser. No. 13/589,021, filed Aug. 17, 2012, which is a continuation-in-part of U.S. application Ser. No. 12/667,228, filed Dec. 29, 2009, which is a U.S. National Phase of the PCT International Application No. PCT/GB2008/050507, filed Jun. 27, 2008, which designated the U.S., published Jan. 8, 2009 as WO 2009/004367, and claims priority to Great Britain Patent Application No. 0712736.8, filed Jul. 2, 2007. U.S. application Ser. No. 13/589,021 is also a continuation-in-part of U.S. application Ser. No. 12/667,231, filed Jun. 30, 2010, which is a U.S. National Phase of the PCT International Application No. PCT/GB2008/002118, filed Jun. 20, 2008, which designated the U.S., published Jan. 8, 2009 as WO 2009/004291, and claims priority to Great Britain Patent Application No. 0712759.0, filed Jul. 2, 2007. U.S. application Ser. No. 13/589,021 is also a continuation-in-part of U.S. application Ser. No. 12/667,326, filed Jul. 6, 2010, which is a U.S. National Phase of the PCT International Application No. PCT/GB2008/002112, filed Jun. 20, 2008, which designated the U.S., published Jan. 8, 2009 as WO 2009/004288, and claims priority to Great Britain Patent Application No. 0712757.4, filed Jul. 2, 2007. U.S. application Ser. No. 13/589,021 is also a continuation-in-part of U.S. application Ser. No. 12/672,055, filed Feb. 3, 2010, which is a U.S. National Phase of the International Application No. PCT/GB2008/050511, filed Jun. 27, 2008, which designated the U.S., published Feb. 12, 2009 as WO 2009/019495, and claims priority to Great Britain Patent Application No. 0715211.9, filed Aug. 6, 2007. U.S. Application No. 13/589,021 is also a continuation-in-part of U.S. application Ser. No. 12/672,063, filed Sep. 23, 2011, which is a U.S. National Phase of the PCT International Application No. PCT/GB2008/002101, filed Jun. 20, 2008, which designated the U.S., published Feb. 12, 2009 as WO 2009/019415, and claims priority to Great Britain Patent Application No. 0715264.8, filed Aug. 6, 2007. U.S. application Ser. No. 13/589,021 is also a continuation-in-part of U.S. application Ser. No. 12/672,065, filed Feb. 3, 2010, which is a U.S. National Phase of the PCT International Application No. PCT/GB2008/002099, filed Jun. 20, 2008, which designated the U.S., published Feb. 12, 2009 as WO 2009/019414, and claims priority to Great Britain Patent Application No. 0715263.0, filed Aug. 6, 2007. U.S. application Ser. No. 13/589,021 is also a continuation-in-part of U.S. application Ser. No. 12/672,490, filed Feb. 5, 2010, which is a U.S. National Phase of the PCT International Application No. PCT/GB2008/002349, filed Jul. 9, 2008, which designated the U.S., published Feb. 12, 2009 as WO 2009/019420, and claims priority to Great Britain Patent Application No. 0715276.2, filed Aug. 6, 2007. U.S. application Ser. No. 13/589,021 is also a continuation-in-part of U.S. application Ser. No. 12/672,468, filed Feb. 5, 2010, which is a U.S. National Phase of the PCT International Application No. PCT/GB2008/002346, filed Jul. 9, 2008, which designated the U.S., published Feb. 12, 2009 as WO 2009/019419, and claims priority to Great Britain Patent Application No. 0715259.8, filed on Aug. 6, 2007. U.S. application Ser. No. 13/589,021 is also a continuation-in-part of U.S. application Ser. No. 12/672,472, filed May 19, 2011, which is a U.S. National Phase of the PCT International Application No. PCT/GB2008/050515, filed Jun. 27, 2008, which designated the U.S., published Feb. 12, 2009 as WO 2009/019496, and claims priority to Great Britain Patent Application No. 0715210.1, filed Aug. 6, 2007. The disclosures of these prior applications are hereby incorporated by reference in their entireties and should be considered a part of this specification.

BACKGROUND

Technical Field

The present disclosure relates to apparatuses and a methods for the application of topical negative pressure (TNP) therapy to wounds. In particular, but not exclusively, the present disclosure relates to controlling pressure provided by a TNP device and alerting users to malfunctions.

Description of the Related Art

There is much prior art available relating to the provision of apparatus and methods of use thereof for the application of TNP therapy to wounds together with other therapeutic processes intended to enhance the effects of the TNP therapy. Examples of such prior art include those listed and briefly described below.

TNP therapy assists in the closure and healing of wounds by reducing tissue oedema; encouraging blood flow and granulation of tissue; removing excess exudates and may reduce bacterial load and thus, infection to the wound. Furthermore, TNP therapy permits less outside disturbance of the wound and promotes more rapid healing.

In our co-pending International patent application, WO 2004/037334, apparatus, a wound dressing and a method for aspirating, irrigating and cleansing wounds are described. In very general terms, this application describes the treatment of a wound by the application of topical negative pressure (TNP) therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In our co-pending International patent application, WO 2005/04670, apparatus, a wound dressing and a method for cleansing a wound using aspiration, irrigation and cleansing wounds are described. Again, in very general terms, this document utilizes similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound.

In our co-pending International patent application, WO 2005/105180, apparatus and a method for the aspiration, irrigation and/or cleansing of wounds are described. Again, in very general terms, this document describes similar apparatus to the two previously mentioned documents hereinabove but with the additional step of providing means for the supply and application of physiologically active agents to the wound site/dressing to promote wound healing.

The content of the above references is included herein by reference.

However, the above apparatus and methods are generally only applicable to a patient when hospitalized as the apparatus is complex, needing people having specialist knowledge in how to operate and maintain the apparatus, and also relatively heavy and bulky, not being adapted for easy mobility outside of a hospital environment by a patient, for example.

Some patients having relatively less severe wounds which do not require continuous hospitalization, for example, but whom nevertheless would benefit from the prolonged application of TNP therapy, could be treated at home or at work subject to the availability of an easily portable and maintainable TNP therapy apparatus.

GB-A-2 307 180 describes a portable TNP therapy unit which may be carried by a patient clipped to belt or harness. It will be appreciated however that there may be certain inaccuracies associated with the provision of a desired pressure or flow rate at a wound site.

Pressure and flow rate provided by the pump must fall within predetermined desired threshold values. It will be appreciated that with prior known pump units a problem is that as the pump wears over time or when certain environmental factors change, the pressure and flow rate provided by the pump can vary which can cause complications or non-ideal environments.

Also with prior known TNP units the control of pressure particularly on 'start-up' of the TNP system or when a new desired pressure is entered by a user can lead to undesirable effects. For example under certain circumstances prior known control mechanisms drive a pump too hard which can damage pump components and thus lead to the need for costly replacement. Also during use a rapid increase or decrease in pump speed can often lead to audible effects. This can concern a user who may think that the TNP system is faulty. Still further rapid changes can lead to pressure 'over shooting' a target value which can lead to increased pain and on occasions bleeding. A rapid change in pressure resulting in pain and discomfort to a patient may lead to immediate fear and rejection by the patient. Also in certain known techniques a user has little or no ability to control pressure provided by a pump.

Another problem which can occur is that when a canister utilized to filter and store waste product becomes full correct operation of the TNP system can be impeded.

In common with most prior art TNP therapy apparatus, the apparatus described cannot differentiate between a blocked or kinked aspiration conduit leading from a dressing to a waste canister and a blockage of the canister itself due to it being full, for example. The alarm to the user on this apparatus can be caused by a number of different faults or conditions.

Also, with current devices two pressure sensors are required on each side of a canister to detect such an event. A change in measured pressure between the two sensors implies a blocked canister filter which further implies a full canister. It will be appreciated that the use of two such sensors is both expensive and prone to error and requires complex processing elements to determine when a canister is full.

It is an aim of some embodiments to at least partly mitigate the above mentioned problems.

It is an aim of some embodiments to provide a method and apparatus of determining a negative pressure and flow rate generated by a pump of a topical negative pressure (TNP) system.

It is an aim of some embodiments to provide control of a suction pump of a topical negative pressure system without requiring both a pressure sensor and flow meter in the system.

It is an aim of some embodiments to provide a method and apparatus for controlling pressure provided by a pump of a topical negative pressure (TNP) system. Another aim is to determine the pressure provided in a controlled manner without over or under exerting a pump or without causing rapid noise changes during use.

It is an aim of some embodiments to provide a method and apparatus for controlling pressure so that jitter and noise caused by sudden changes in pump speed are reduced or avoided altogether.

It is an aim of some embodiments to provide a method and apparatus which allows for early detection of leaks in a TNP system.

It is an aim of some embodiments to provide a method and apparatus of determining status of a canister of a TNP system. More particularly, but not exclusively, it is an aim of some embodiments to provide a method and apparatus for determining when a canister of a TNP system is full.

It is an aim of some embodiments to provide an indication of when a canister of a TNP system is full without a requirement for two pressure sensors in the TNP system.

It is an aim of some embodiments to provide an apparatus which is able to distinguish between at least some distinct aspirant fluid non-flow conditions in TNP therapy apparatus so that a user is appropriately informed.

For purposes of summarizing the disclosure, certain aspects, advantages and novel features have been described herein. It is to be understood that not necessarily all such advantages can be achieved in accordance with any particular embodiment disclosed herein. Thus, the disclosure described herein can be embodied or carried out in a manner that achieves or optimizes one advantage or a group of advantages as taught herein without necessarily achieving other advantages as can be taught or suggested herein.

SUMMARY

According to some embodiments, an overall apparatus for the provision of TNP therapy to a patient in almost any environment is provided. The apparatus is lightweight, may be mains or battery powered by a rechargeable battery pack contained within a device (henceforth, the term "device" is used to connote a unit which may contain all of the control, power supply, power supply recharging, electronic indicator means and means for initiating and sustaining aspiration functions to a wound and any further necessary functions of a similar nature). When outside the home, for example, the apparatus may provide for an extended period of operation on battery power and in the home, for example, the device may be connected to the mains by a charger unit whilst still being used and operated by the patient.

In some embodiments, the overall apparatus comprises: a dressing covering the wound and sealing at least an open end of an aspiration conduit to a cavity formed over the wound by the dressing; an aspiration tube comprising at least one lumen therethrough leading from the wound dressing to a waste material canister for collecting and holding wound exudates/waste material prior to disposal; and, a power, control and aspiration initiating and sustaining device associated with the waste canister.

In some embodiments, the dressing covering the wound may be any type of dressing normally employed with TNP therapy and, in very general terms, may comprise, for example, a semi-permeable, flexible, self-adhesive drape material, as is known in the dressings art, to cover the wound and seal with surrounding sound tissue to create a sealed cavity or void over the wound. There may aptly be a porous barrier and support member in the cavity between the wound bed and the covering material to enable an even vacuum distribution to be achieved over the area of the wound. The porous barrier and support member being, for example, a gauze, a foam, an inflatable bag or known wound contact type material resistant to crushing under the levels of vacuum created and which permits transfer of wound exudates across the wound area to the aspiration conduit sealed to the flexible cover drape over the wound.

In some embodiments, the aspiration conduit may be a plain flexible tube, for example, having a single lumen therethrough and made from a plastics material compatible with raw tissue, for example. However, the aspiration conduit may have a plurality of lumens therethrough to achieve specific objectives disclosed herein. A portion of the tube sited within the sealed cavity over the wound may have a structure to enable continued aspiration and evacuation of wound exudates without becoming constricted or blocked even at the higher levels of the negative pressure range envisaged.

In some embodiments, it is envisaged that the negative pressure range for the apparatus may be between about −50 mmHg and −200 mmHg (note that these pressures are relative to normal ambient atmospheric pressure thus, −200 mmHg would be about 560 mmHg in practical terms). Aptly, the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

In some embodiments, the aspiration conduit at its distal end remote from the dressing may be attached to the waste canister at an inlet port or connector. The device containing the means for initiating and sustaining aspiration of the wound/dressing may be situated between the dressing and waste canister, however, in a preferred embodiment, the device may aspirate the wound/dressing via the canister thus, the waste canister may preferably be sited between the wound/dressing and device.

The aspiration conduit at the waste material canister end may preferably be bonded to the waste canister to prevent inadvertent detachment when being caught on an obstruction, for example.

In some embodiments, the canister may be a plastics material moulding or a composite unit comprising a plurality of separate mouldings. The canister may aptly be translucent or transparent in order to visually determine the extent of filling with exudates. However, the canister and device may in some embodiments provide automatic warning of imminent canister full condition and may also provide means for cessation of aspiration when the canister reaches the full condition.

In some embodiments, the canister may be provided with filters to prevent the exhaust of liquids and odors therefrom and also to prevent the expulsion of bacteria into the atmosphere. Such filters may comprise a plurality of filters in series. Examples of suitable filters may comprise hydrophobic filters of 0.2 µm pore size, for example, in respect of sealing the canister against bacteria expulsion and 1 µm against liquid expulsion.

Aptly, in some embodiments, the filters may be sited at an upper portion of the waste canister in normal use, that is when the apparatus is being used or carried by a patient the filters are in an upper position and separated from the exudate liquid in the waste canister by gravity. Furthermore, such an orientation keeps the waste canister outlet or exhaust exit port remote from the exudate surface.

Aptly, in some embodiments, the waste canister may be filled with an absorbent gel such as ISOLYSEL (trade mark), for example, as an added safeguard against leakage of the canister when full and being changed and disposed of. Added advantages of a gel matrix within the exudate storing volume of the waste canister are that it prevents excessive movement, such as slopping, of the liquid, minimizes bacterial growth and minimizes odors.

In some embodiments, the waste canister may also be provided with suitable means to prevent leakage thereof both when detached from the device unit and also when the aspiration conduit is detached from the wound site/dressing.

In some embodiments, the canister may have suitable means to prevent emptying by a user (without tools or damage to the canister) such that a full or otherwise end-of-life canister may only be disposed of with waste fluid still contained.

In some embodiments, the device and waste canister may have mutually complementary means for connecting a device unit to a waste canister whereby the aspiration means in the device unit automatically connects to an evacuation port on the waste canister such that there is a continuous aspiration path from the wound site/dressing to an exhaust port on the device.

Aptly, in some embodiments, the exhaust port from the fluid path through the apparatus is provided with filter means to prevent offensive odors from being ejected into the atmosphere.

In some embodiments, the device unit comprises an aspirant pump; means for monitoring pressure applied by the aspirant pump; may have a flowmeter to monitor fluid flow through the aspirant pump; a control system which controls the aspirant pump in response to signals from sensors such as the pressure monitoring means and the flowmeter, for example, and which control system also controls a power management system with regard to an on-board battery pack and the charging thereof and lastly a user interface system whereby various functions of the device such as pressure level set point, for example, may be adjusted (including stopping and starting of the apparatus) by a user. The device unit may contain all of the above features within a single unified casing.

In view of the fact that the device unit contains the majority of the intrinsic equipment cost therein ideally it will also be able to survive impact, tolerate cleaning in order to be reusable by other patients.

In some embodiments, in terms of pressure capability the aspiration means may be able to apply a maximum pressure drop of at least 200 mmHg to a wound site/dressing. The apparatus is capable of maintaining a predetermined negative pressure even under conditions where there is a small leak of air into the system and a high exudate flow.

In some embodiments, the pressure control system may prevent the minimum pressure achieved from exceeding for example 200 mmHg so as not to cause undue patient discomfort. The pressure required may be set by the user at a number of discreet levels such as 50, 75, 100, 125, 150, 175 mmHg, for example, depending upon the needs of the wound in question and the advice of a clinician. Thus suitable pressure ranges in use may be from 25 to 80 mmHg, or 50 to 76 mmHg, or 50 to 75 mmHg as examples. The control system may also advantageously be able to maintain the set pressure within a tolerance band of +/−10 mmHg of the set point for 95% of the time the apparatus is operating given that leakage and exudation rates are within expected or normal levels.

Aptly, in some embodiments, the control system may trigger alarm means such as a flashing light, buzzer or any other suitable means when various abnormal conditions apply such as, for example: pressure outside set value by a large amount due to a gross leak of air into system; duty on the aspiration pump too high due to a relatively smaller leakage of air into the system; pressure differential between wound site and pump is too high due, for example, to a blockage or waste canister full.

In some embodiments, the apparatus may be provided with a carry case and suitable support means such as a shoulder strap or harness, for example. The carry case may be adapted to conform to the shape of the apparatus comprised in the joined together device and waste canister. In particular, the carry case may be provided with a bottom opening flap to permit the waste canister to be changed without complete removal of the apparatus form the carry case.

In some embodiments, the carry case may be provided with an aperture covered by a displaceable flap to enable user access to a keypad for varying the therapy applied by the apparatus.

According to some embodiments, there is provided a method of determining a negative pressure generated by a suction pump of a topical negative pressure (TNP) system, the method comprising the steps of:
  disconnecting a drive voltage from a pump of a TNP system;
  determining an EMF generated by a free-wheeling element of the pump;
  selecting a new drive voltage for the pump; and
  reconnecting the new drive voltage to the pump.

According to some embodiments, there is provided apparatus that determines a negative pressure generated by a suction pump of a topical negative pressure (TNP) system, comprising:
  a pump that provides a negative pressure responsive to a pump speed;
  a PWM generator that provides an output signal which provides a drive voltage for the pump; and
  a processor that calculates an EMF generated by a free-wheeling element of the pump and selects a new drive voltage responsive thereto; wherein
  the PWM generator is arranged to receive a control signal that disconnects the pump from a drive voltage and reconnects the new drive voltage to the pump.

According to some embodiments, there is provided a method of determining pressure provided by a pump of a topical negative pressure (TNP) system, the method comprising the steps of:
  determining a value associated with a measured pressure;
  determining a difference between the measured pressure value and a predetermined desired value; and
  increasing or decreasing a speed of pumping of the pump responsive to the difference.

According to some embodiments, there is provided apparatus that controls pressure provided by a pump of a topical negative pressure TNP system, comprising:
  a pressure sensor that measures pressure at an inlet to the pump;
  a user interface via which a user can indicate a predetermined desired value; and
  a processing unit that compares a value, associated with the measured pressure, with said predetermined value and increases or decreases a speed of pumping of the pump responsive to the compared result.

According to some embodiments, there is provided a method of determining pressure provided by a pump element of a topical negative pressure (TNP) system, comprising the steps of:
  determining current pressure provided by a pump element of a TNP system;
  comparing the determined pressure with a predetermined pressure;
  selecting a target pressure intermediate the current and predetermined pressure and increasing or decreasing pump speed to respectively increase or decrease pressure until the current pressure matches the target pressure.

According to some embodiments, there is provided apparatus for determining pressure provided by a pump element of a topical negative pressure (TNP) system, comprising:
  a pressure sensor for determining current pressure provided by a pump element;
  a processing unit comprising at least one processing element arranged to compare the current pressure with a predetermined pressure and select a target pressure intermediate the current and predetermined pressure; and
  a pump speed control unit arranged to increase or decrease pump speed and thereby pressure until the current pressure matches the target pressure.

Some embodiments provide a controlled manner in which pump pressure can be increased or decreased from a current pressure to desired pressure. The pressure changes are stepped so that rather than a rapid large step change in pressure the stepped change is controlled. As a result a pump unit of the TNP system is not over taxed and also audible effects which may otherwise concern a user are obviated.

Some embodiments also provide a method and apparatus which allow for early detection of leaks of a TNP system. The leaks are detected as a failure to achieve any of a plurality of temporary 'set pressures'. This can be used to trigger an audible and/or visual alarm. Disclosed embodiments which allow such early detection are preferable to prior known systems in that the fault is detected when failure to achieve a modest stepped change is noted rather than subsequent to the failure to achieve the final operating pressure which may otherwise be expected to occur later in time than the attainment of a smaller stepped change.

According to some embodiments, there is provided apparatus for determining flow rate in a topical negative pressure (TNP) system, comprising:
  a pump element, comprising a rotor element that provides negative pressure in a flow path;
  a pressure sensor arranged to determine a pressure in the flow path; and
  a processing unit that determines a pumping speed associated with the pump element and determines flow rate in the flow path responsive to the pumping speed and pressure.

According to some embodiments, there is provided apparatus for determining pressure in a topical negative pressure (TNP) system, comprising:
  a pump element, comprising a rotor element that provides negative pressure in a flow path;
  a flow meter arranged to determine a flow rate in the flow path; and a processing unit that determines a pumping speed associated with the pump element and determines pressure in the flow path responsive to the pumping speed and flow rate.

Some embodiments provide a method and apparatus in which the flow rate and pressure in a TNP system may be determined without the need for a flow meter and pressure sensor. Flow rate can be calculated using only a pressure sensor which is placed in any one of a number of optional locations in a flow path. Pressure can be calculated using only a flow meter, the flow meter can be placed anywhere along a flow path to achieve pressure calculations. This provides a very versatile pressure sensing technique which can be utilized to measure pressure in locations where a pressure sensor would not otherwise be usable. This results in a very versatile system. A flow meter could be used instead to measure flow rate, but is far more costly than utilization of a pressure sensor and a mechanism for determining pump speed. The flow rate calculated according to embodiments is also highly accurate. Additionally, some embodiments reduce part count in a TNP system in which a flow meter or pressure sensor is already often useful or necessary.

According to some embodiments, an alternative flow and pressure measurement mechanisms can be provided in addition to flow meters and pressure sensors in a TNP system. This can be utilized as a safety back up by comparing results and determining that an error has occurred if the results do not match. In such instances one or more pressure sensors and flow meters may optionally be utilized.

According to some embodiments, there is provided apparatus for determining status in a canister of a topical negative pressure (TNP) system, comprising:

a canister arranged to collect exudate from an aspirant tube locatable at a wound site;

a pump element arranged to pump air and/or exudate from the tube through the canister;

a pressure sensor for monitoring pressure provided by the pump element; and a processing unit comprising at least one processing element that determines at least one characteristic associated with the monitored pressure and determines status of at least one parameter associated with the canister responsive to the determined characteristic.

According to some embodiments, there is provided a method of determining the occurrence of a blockage of a canister filter in a topical negative pressure (TNP) system comprising the steps of:

monitoring pressure provided by a pump element of the TNP system; and determining if a monitored pressure falls below a pre-determined threshold value.

According to some embodiments, there is provided apparatus for determining the occurrence of a blockage of a canister filter in a topical negative pressure (TNP) system, comprising:

a canister arranged to collect exudate from an aspirant tube locatable at a wound site;

a filter arranged to filter air in the canister;

a pump element arranged to pump air and/or exudate from the tube through the canister;

a pressure sensor arranged to monitor pressure generated by the pump; and a processing unit comprising at least one processing element arranged to determine if a monitored pressure falls below a pre-determined threshold value.

Some embodiments provide a method and apparatus which allows the status of a canister of a topical negative pressure (TNP) system to be determined without the necessity to provide two pressure sensors in the TNP system. By monitoring the magnitude of pressure 'pulses' created by a pump possible leakage or the fact that a canister filter may be full can be detected. Optionally two or more sensors can be used if very prompt detection of errors is desired.

According to some embodiments, there is provided a method of determining status in a canister of a topical negative pressure (TNP) system, comprising the steps of:

monitoring pressure provided by a pump element of the TNP system;

determining at least one characteristic associated with the monitored pressure; and determining status of at least one parameter associated with a canister of the TNP system responsive to the determined characteristics.

According to some embodiments, there is provided a method of alerting a user of topical negative pressure therapy apparatus to a full waste canister condition, the method comprising the steps of placing fluid flow restriction means in the fluid flow path of said vacuum pump and monitoring fluid pressures upstream and downstream of said fluid flow restriction means.

In the general structure of the TNP device described, a system for determining and alerting a user to a full canister condition may be based on a flowmeter sensor. In such a system the control system monitors readings of fluid flow through a flowmeter at intervals and when the fluid (gas) flow approaches or falls to zero an alarm is activated to warn the user of the condition. In reality the fluid flow may fall to zero due either to the aspiration conduit being blocked (by wound exudate, for example) or to the waste canister being full and the exit port filters in the waste canister being blocked, for example. Thus, the flowmeter in the system effectively equates low or zero flow, when the pump is otherwise functioning normally, to a blocked or full waste system. In any event, whether the aspiration conduit is blocked or the waste canister is full it is a condition which requires attention from the user to rectify since under both circumstances the wound is not being aspirated.

According to some embodiments and alternatively to the flowmeter-based control system described in the preceding paragraph, a flowmeter is dispensed with and a flow restriction, such as a small orifice, is placed in the fluid flow path within the device exhaust system, preferably at a position near to an exhaust outlet port. Aptly the fluid flow restriction may be placed downstream of the vacuum aspirant pump. A pressure sensor monitors the pressure differential at upstream and downstream positions relative to the restriction. Alternatively, two pressure sensors may be used to monitor pressure in the fluid flow path at upstream and downstream position relative to the restriction, signals from the two pressure sensors being monitored by the control system and the difference therebetween calculated at intervals. When the pressure differential or difference between the two positions tends to zero the control system interprets this as the fluid flow also tending to zero which as in the flowmeter based system effectively equates this as a full or blocked waste system as before.

In some embodiments, the size of the restriction placed in the fluid flow path towards the exhaust may be an aperture, aptly a round aperture as this is the most economic shape to make, but does not exclude other shapes such as square or hexagonal, for example, of a size of less than 1 mm diameter or, more preferably, lying between 0.05 to 1.0 mm in diameter. The actual size may depend upon the flow rate of fluid passing through the fluid flow path. In general typical pumps used in the present apparatus may have flow rates, open port, in the range from 4 to 20 l/min. This flow rate clearly reduces as the vacuum or negative pressure in the system up to the dressing increases. An example of a suitable pump for use in the present apparatus may have an open port flow rate of 4.8 l/min. Under free flow conditions where there is no blockage in the aspirant conduit and the waste canister is substantially less than full, flow rates of up to 3 l/min have been measured with such a pump. Thus, the size of the aperture must be chosen so as to produce accurate pressure signals at low flow rates when the aspirated system is becoming full or otherwise blocked and flow rates tend to zero on the downstream side of the pump. The size of the tubing used in the flow path on the downstream side of the pump also has an effect on flow rates. In general the tubing used in what is effectively the exhaust system of the apparatus is desirably of a suitable bore which does not itself impede flow too much and tubing sizes of 3 mm and above are preferred. In general a flow rate of about 0.1 l/min minimum may be needed in order to maintain flow of wound exudate from the wound/dressing site, through the aspiration conduit and into the waste canister, this flow rate being dependent to an extent on other factors such as the bore size of the aspiration conduit, for example.

In some embodiments, when the fluid flow through the apparatus is relatively high and relatively unrestricted, an abnormal burden may be placed on the vacuum pump causing it to operate inefficiently or perhaps necessitating a larger or more powerful than necessary pump to overcome the flow restriction caused by the restrictor. In some embodiments to deal with this possible disadvantage, a variable area flow restrictor electrically connected to the control system may be employed. A pressure sensor upstream of the flow restrictor sends signals to the control system. When that pressure is greater than a stored value in the control system memory, the control system adjusts the area of the variable area flow restrictor so that the area is increased and the flow restriction consequently reduced. When fluid flow falls due to an impending or actual blockage in the fluid flow system, the pressure sensed by the sensor connected to the control system falls to below the stored value causing the control system to adjust the variable area flow restrictor to a lower, predetermined value. At this lower, predetermined value the flow is restricted so that accuracy of pressure sensing is enhanced at low flow rates of gaseous aspirated fluid and the control system operates as before to activate an alarm when flow rates fall to a level where the pressure differential sensed falls below a stored value in the control system.

In some embodiments, as an alternative to a variable area flow restrictor, a by-pass conduit across a fixed aperture flow restrictor may be employed, the by-pass having a valve therein. The valve may be a settable valve adjusted to open and permit flow through the by-pass conduit when the pressure upstream of the restrictor is greater than the preset value in the settable valve. Thus, load on the pump is reduced under normal free-flow operating conditions. When the fluid flow rate starts to fall and the pressure drops below the preset value in the valve, the valve closes and fluid flow is again directed through a fixed area restrictor.

According to some embodiments, the control system may work with the following logic steps:
1. Initiate blockage sensing process
2. Read pressure sensor value
3. Compare value to stored minimum value
4. If read value is less than stored value the system is considered blocked (or the canister is full)
5. Trigger the "Canister full" alarm (visual and/or audible)
6. End blockage sensing process
7. Repeat when next required (based on software timings).

In prior art TNP apparatus blockages in the waste canister filter due to full canister, for example, or a blocked aspirant conduit due to waste exudate or a kink in the conduit can be detected by measuring differential pressure readings or by using a flow meter. However, this is not sufficient to be able to distinguish whether the cause of a decrease in aspirant fluid flow rate is a full waste canister or a blocked aspirant conduit. In the apparatus according to some embodiments, it is desired to be able to distinguish between various aspirant fluid non-flow conditions and to be able to alert a user with a specific warning appropriate to the specific condition or fault.

According to some embodiments, there is provided a method of alerting a user of topical negative pressure therapy apparatus to a non-flow condition of aspirant fluid in the apparatus, the apparatus comprising a device having vacuum pump means and a waste canister connected to the device; the waste canister being operably connected to a wound dressing by aspiration conduit means for aspirating fluid from the wound; the aspiration conduit means, the waste canister and the device providing a fluid flow path therethrough and the vacuum pump means providing for fluid flow therethrough; the device having flowmeter means and first pressure sensing means at an upstream position between an outlet port for aspirated fluid from said waste canister and said pump means; said waste canister having further provision for selectable valve means for admission of ambient air to said waste canister; and, a control system for receiving signals from said flowmeter means and said pressure sensor and initiating control signals in response and activating an appropriate user alarm, said method comprising the steps of: measuring fluid flow and comparing actual fluid flow with a stored fluid flow value in control system memory means; opening said selectable valve means in response to actual fluid flow being below said stored value; measuring actual fluid flow after opening said selectable valve means; and activating an alarm corresponding to one of "canister full" and "aspirant conduit blocked" according to actual fluid flow value after opening of said selectable valve means.

According to some embodiments, there is provided a method of alerting a user of topical negative pressure therapy apparatus to a non-flow condition of aspirant fluid in the apparatus, the apparatus comprising a device having vacuum pump means and a waste canister connected to the device; the waste canister being operably connected to a wound dressing by aspiration conduit means for aspirating fluid from the wound; the aspiration conduit means, the waste canister and the device providing a fluid flow path therethrough and the vacuum pump means providing for fluid flow therethrough; the device having first pressure sensing means at an upstream position between an outlet port for aspirated fluid from said waste canister and said pump means; said waste canister having second pressure sensor means associated therewith; and, a control system for receiving signals from said first and second pressure sensor means and initiating control signals in response to said signals and activating an appropriate user alarm, said method comprising the steps of: measuring pressure at said first pressure sensor and at said second pressure sensor; comparing said first and said second pressures; if a pressure difference between first and second pressures is greater than a stored value in a memory of said control system, activating a "canister full" alarm; alternatively, if a difference between the first pressure and second pressure is less than the stored value in said control system memory, activating a "conduit blocked" alarm.

According to some embodiments, there is provided apparatus for alerting a user of topical negative pressure therapy apparatus to a non-flow condition of aspirant fluid in the apparatus, the apparatus comprising: a device having vacuum pump means and a waste canister connected to the device; the waste canister being operably connected to a wound dressing by aspiration conduit means for aspirating fluid from the wound; the aspiration conduit means, the waste canister and the device providing a fluid flow path therethrough and the vacuum pump means providing for fluid flow therethrough; the device having first pressure sensing means at an upstream position between an outlet port for aspirated fluid from said waste canister and said pump means; said waste canister having further provision selected from one of, selectable valve means for admission of ambient air to said waste canister and second pressure sensing means for sensing pressure in said waste canister; and, a control system for receiving signals from said sensors and initiating control signals in response and activating an appropriate user alarm.

In some embodiments of the method and apparatus, the waste canister is provided with a further port having an air access tube and/or a selectable valve associated therewith. The selectable valve may be a solenoid type valve, for example, and be selected in accordance with control responses from the control system. The port may be opened to atmosphere by opening of the selectable valve. When the control system senses a blockage by, for example, a fall in aspirated fluid flow rate through the fluid flow path, the control system opens the valve so as to admit air into the waste canister (it will be understood that the interior of the waste canister forms part of the fluid flow path through the apparatus, the fluid flow path extending from the end of the aspirant conduit at the wound site/dressing to the final exhaust port venting aspirated gaseous fluid to atmosphere in the device). If the canister is full then the effect that opening this port and the subsequent air flow into the canister will have on the flow meter located in the device and which is in electrical connection with the control system, will be much less than the effect which would pertain if the fault is a blocked aspirant conduit. If the aspirant conduit between the waste canister and the wound site/dressing is blocked by waste matter or the conduit is kinked, for example, the blockage measured by the flowmeter will effectively disappear as inflowing air into the canister via the selectable valve will restore the fluid flow rate in the fluid flow path. If, however, the blockage is due to a full waste canister or a blocked waste canister filter adjacent the fluid outlet port in the waste canister then opening the valve will have little or no effect on the fluid flow rate through the fluid flow path. Thus depending upon the resulting effect of opening the selectable valve to atmosphere, the control system can determine the cause and location of the blockage and alert the user appropriately. This is important to a user since if the problem is merely a kinked or twisted or otherwise caught aspirant conduit then the user is able to instantly remedy the fault and has no need to check if the canister is full.

In some embodiments, where a selectable valve is employed in the waste canister to admit ambient air therein it is preferred that the opening so formed is provided with appropriate filters so as to prevent any possible ejection of waste material and/or bacteria from the canister.

In some embodiments, in the control system memory a pressure value for a blocked system (from any cause) is defined. At periodic intervals, whilst the apparatus is in use, the control system samples the pressure at the sensor upstream of the pump and compares that pressure with the stored blocked system value and takes appropriate action when certain criteria are fulfilled.

In some embodiments, the two pressure sensors need to detect whether the canister is full or if the aspirant conduit is blocked. Under normal operating conditions the first pressure at the pump inlet will be whatever the set pressure may be and the second pressure in the canister will be somewhat lower, for example about 20mmHg less (i.e. 20 mmHg less negative), due to the pressure drop caused by the flow of fluid through the filter at the canister exit port. Thus, when the apparatus is operating normally with no blockages of any kind the pressure difference between first and second pressures may be of the order of +20 mmHg. When the canister is full and can no longer transmit aspirant (gaseous) fluid through the filter to the canister exit port due to the filter being occluded by waste material, the pressure in the canister will eventually rise towards atmospheric as the pressure in the aspirant conduit connected to the dressing will rise due to no vacuum being applied by the pump due to the occluded canister filter.

Consequently, the pressure difference will rise (increase in the negative direction if being measured relative to atmosphere) to a difference significantly more than that pertaining under normal operating conditions thus, the control system will recognize diverging first and second pressures as indicating a full canister. However, in the case where the aspirant conduit is blocked by kinking or twisting, for example, the pressure difference will diminish between first and second pressures as the vacuum level in the canister (second pressure) will decrease to approach that at the pump inlet (first pressure). Consequently, the control system will recognize converging first and second pressures as indicating a blocked aspirant conduit. Depending upon which condition exists an appropriate alarm will be activated.

In some embodiments, the "stored value" in the control system may be a range or tolerance band of pressures rather than a single unique pressure to permit more meaningful operation of the two conditions described above. Thus, under "normal" operating conditions the control system will recognize pressures lying within a stored range.

The method according to some embodiments may also employ flowmeter means, the control system memory also having a stored value of fluid flow below which a potential blockage is recognized.

BRIEF DESCRIPTION OF THE DRAWINGS

In order that the disclosure may be more fully understood, examples will now be described by way of illustration only with reference to the accompanying drawings, of which:

FIGS. 20A-20F show embodiments configured to determine if there is a blockage in the flow path;

FIG. 24 shows a schematic diagram of apparatus according to some embodiments;

FIG. 25 shows a schematic diagram of apparatus according to some embodiments;

DETAILED DESCRIPTION

Figure 1:
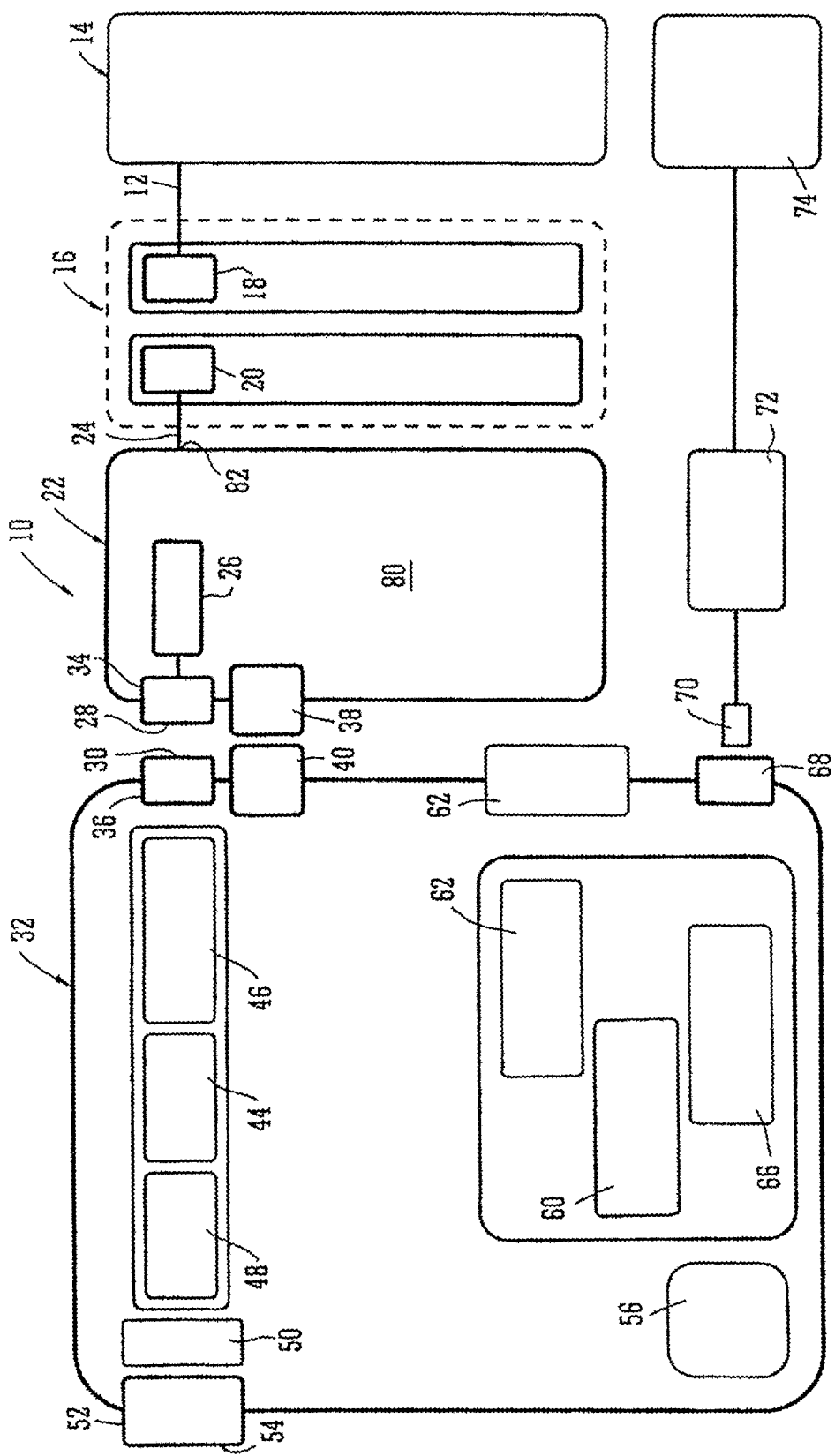
FIG. 1 shows a generalized schematic block diagram showing a general view of an apparatus and the constituent apparatus features thereof.

Referring now to FIGS. 1 to 4 of the drawings and where the same or similar features are denoted by common reference numerals.

FIG. 1 shows a generalized schematic view of an apparatus 10 of a portable topical negative pressure (TNP) system according to some embodiments. It will be understood that disclosed embodiments are generally applicable to use in such a TNP system. Briefly, negative pressure wound therapy assists in the closure and healing of many forms of "hard to heal" wounds by reducing tissue oedema; encouraging blood flow and granular tissue formation; removing excess exudate and may reduce bacterial load (and, therefore, infection). In addition the therapy allows for less disturbance of a wound leading to more rapid healing. The TNP system is detailed further hereinafter but in summary includes a portable body including a canister and a device with the device capable of providing an extended period of continuous therapy within at least a one year life span. The system is connected to a patient via a length of tubing with an end of the tubing operably secured to a wound dressing on the patient.

More particularly, as shown in FIG. 1, the apparatus comprises an aspiration conduit 12 operably and an outer surface thereof at one end sealingly attached to a dressing 14. The dressing 14 will not be further described here other than to say that it is formed in a known manner from well know materials to those skilled in the dressings art to create a sealed cavity over and around a wound to be treated by TNP therapy with the apparatus. The aspiration conduit has an in-line connector 16 comprising connector portions 18, 20 intermediate its length between the dressing 14 and a waste canister 22. The aspiration conduit between the connector portion 20 and the canister 22 is denoted by a different reference numeral 24 although the fluid path through conduit portions 12 and 24 to the waste canister is continuous. The connector portions 18, 20 join conduit portions 12, 24 in a leak-free but disconnectable manner. The waste canister 22 is provided with filters 26 which prevent the escape via an exit port 28 of liquid and bacteria from the waste canister. The filters may comprise a 1 μm hydrophobic liquid filter and a 0.2 μm bacteria filter such that all liquid and bacteria is confined to an interior waste collecting volume of the waste canister 22. The exit port 28 of the waste canister 22 mates with an entry/suction port 30 of a device unit 32 by means of mutually sealing connector portions 34, 36 which engage and seal together automatically when the waste canister 22 is attached to the device unit 32, the waste canister 22 and device unit 32 being held together by catch assemblies 38, 40. The device unit 32 comprises an aspirant pump 44, an aspirant pressure monitor 46 and an aspirant flowmeter 48 operably connected together. The aspiration path takes the aspirated fluid which in the case of fluid on the exit side of exit port 28 is gaseous through a silencer system 50 and a final filter 52 having an activated charcoal matrix which ensures that no odors escape with the gas exhausted from the device 32 via an exhaust port 54. The filter 52 material also serves as noise reducing material to enhance the effect of the silencer system 50. The device 32 also contains a battery pack 56 to power the apparatus which battery pack also powers the control system 60 which controls a user interface system 62 controlled via a keypad (not shown) and the aspiration pump 44 via signals from sensors 46, 48. A power management system 66 is also provided which controls power from the battery pack 56, the recharging thereof and the power requirements of the aspirant pump 44 and other electrically operated components. An electrical connector 68 is provided to receive a power input jack 70 from a SELV power supply 72 connected to a mains supply 74 when the user of the apparatus or the apparatus itself is adjacent a convenient mains power socket.

Figure 2:
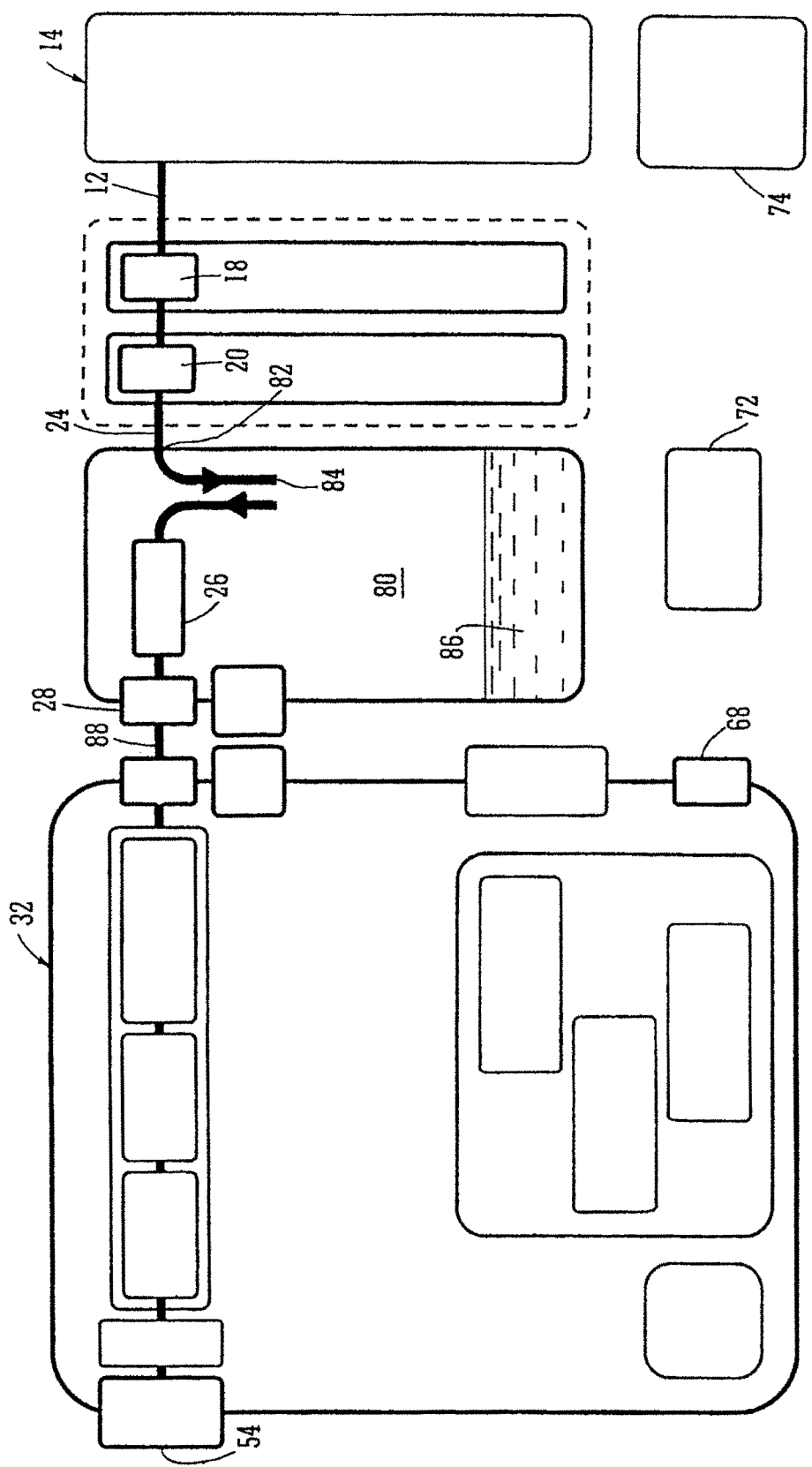
FIG. 2 shows a similar generalized schematic block diagram to FIG. 1 and showing fluid paths therein.

FIG. 2 shows a similar schematic representation to FIG. 1 but shows the fluid paths in more detail. The wound exudate is aspirated from the wound site/dressing 14 via the conduit 12, the two connector portions 18, 20 and the conduit 24 into the waste canister 22. The waste canister 22 comprises a relatively large volume 80 in the region of 500ml into which exudate from the wound is drawn by the aspiration system at an entry port 82. The fluid 84 drawn into the canister volume 80 is a mixture of both air drawn into the dressing 14 via the semi-permeable adhesive sealing drape (not shown) and liquid 86 in the form of wound exudates. The volume 80 within the canister is also at a lowered pressure and the gaseous element 88 of the aspirated fluids is exhausted from the canister volume 80 via the filters 26 and the waste canister exhaust exit port 28 as bacteria-free gas. From the exit port 28 of the waste canister to the final exhaust port 54 the fluid is gaseous only.

Figure 3:
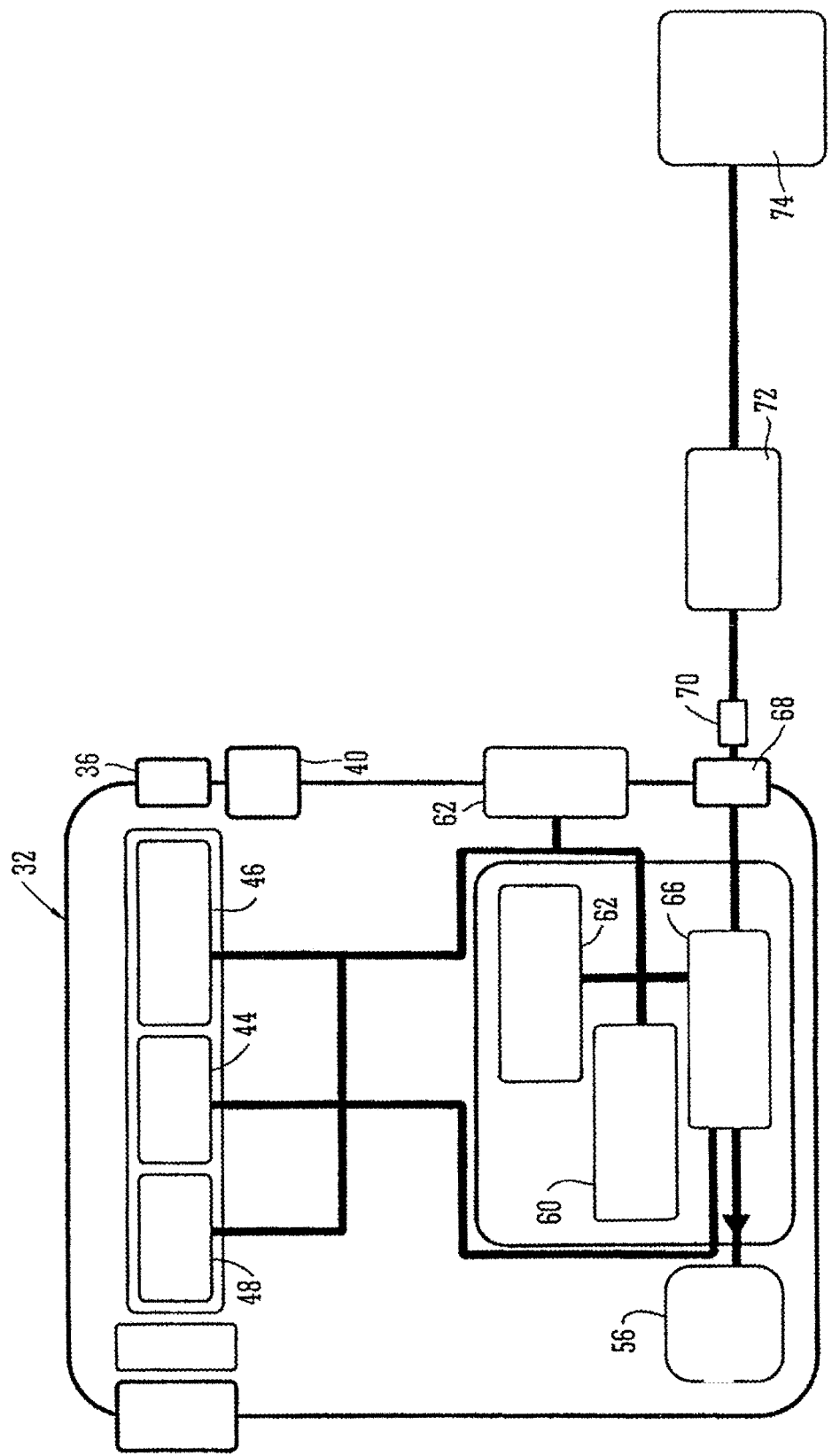
FIG. 3 shows a generalized schematic block diagram similar to FIG. 1 but of a device unit only and showing power paths for the various power consuming/producing features of the apparatus.

FIG. 3 shows a schematic diagram showing only the device portion of the apparatus and the power paths in the device of the apparatus according to some embodiments.

Power is provided mainly by the battery pack 56 when the user is outside their home or workplace, for example, however, power may also be provided by an external mains 74 supplied charging unit 72 which when connected to the device 32 by the socket 68 is capable of both operating the device and recharging the battery pack 56 simultaneously. The power management system 66 is included so as to be able to control power of the TNP system. The TNP system is a rechargeable, battery powered system but is capable of being run directly from mains electricity as will be described hereinafter more fully with respect to the further figures. If disconnected from the mains the battery has enough stored charge for approximately 8 hours of use in normal conditions. It will be appreciated that batteries having other associated life times between recharge can be utilized. For example batteries providing less than 8 hours or greater than 8 hours can be used. When connected to the mains the device will run off the mains power and will simultaneously recharge the battery if depleted from portable use. The exact rate of battery recharge will depend on the load on the TNP system. For example, if the wound is very large or there is a significant leak, battery recharge will take longer than if the wound is small and well-sealed.

Figure 4:
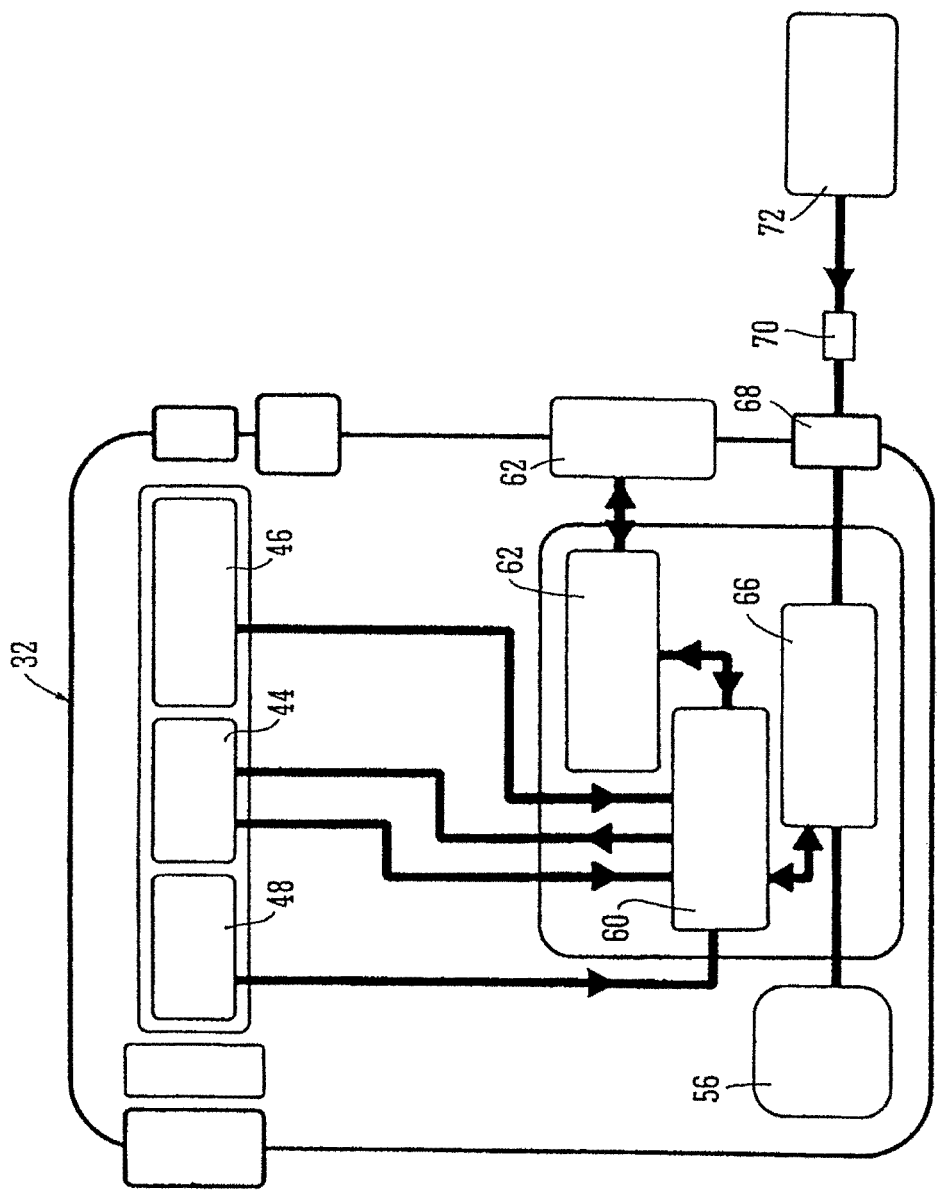
FIG. 4 shows a similar generalized schematic block diagram to FIG. 3 of the device unit and showing control system data paths for controlling the various functions and components of the apparatus.
Figure 5:
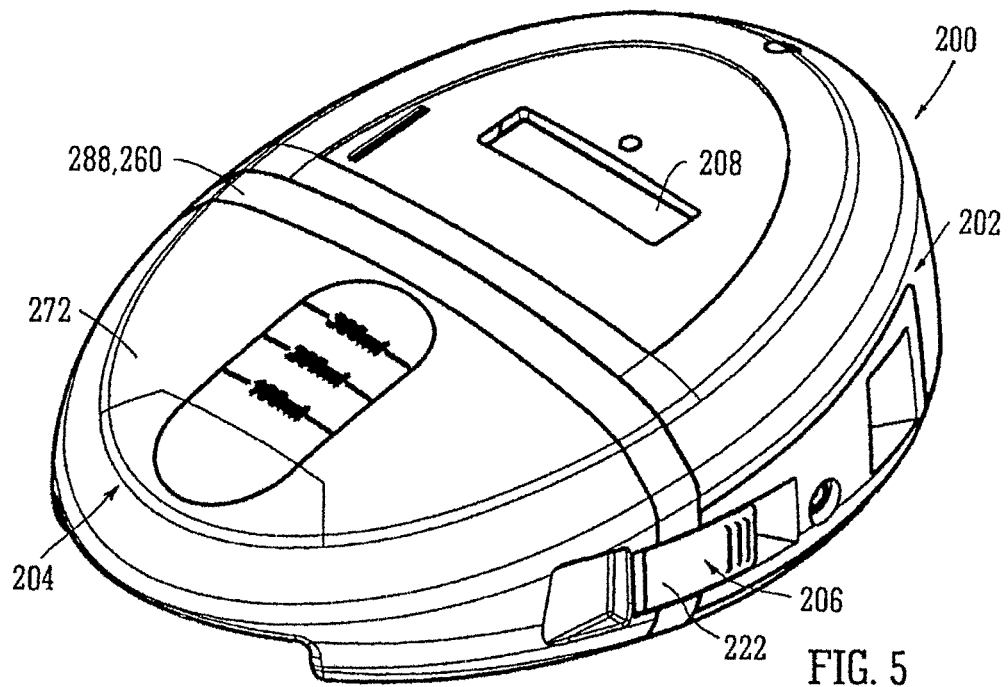
FIG. 5 shows a perspective view of an apparatus.
Figure 6:
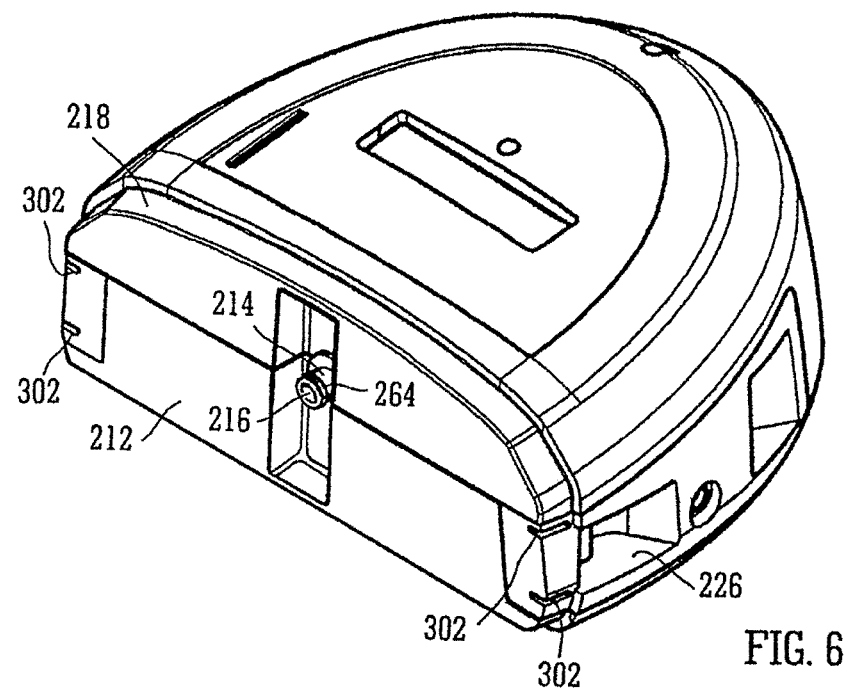
FIG. 6 shows a perspective view of an assembled device unit of the apparatus of FIG. 5.
Figure 7:
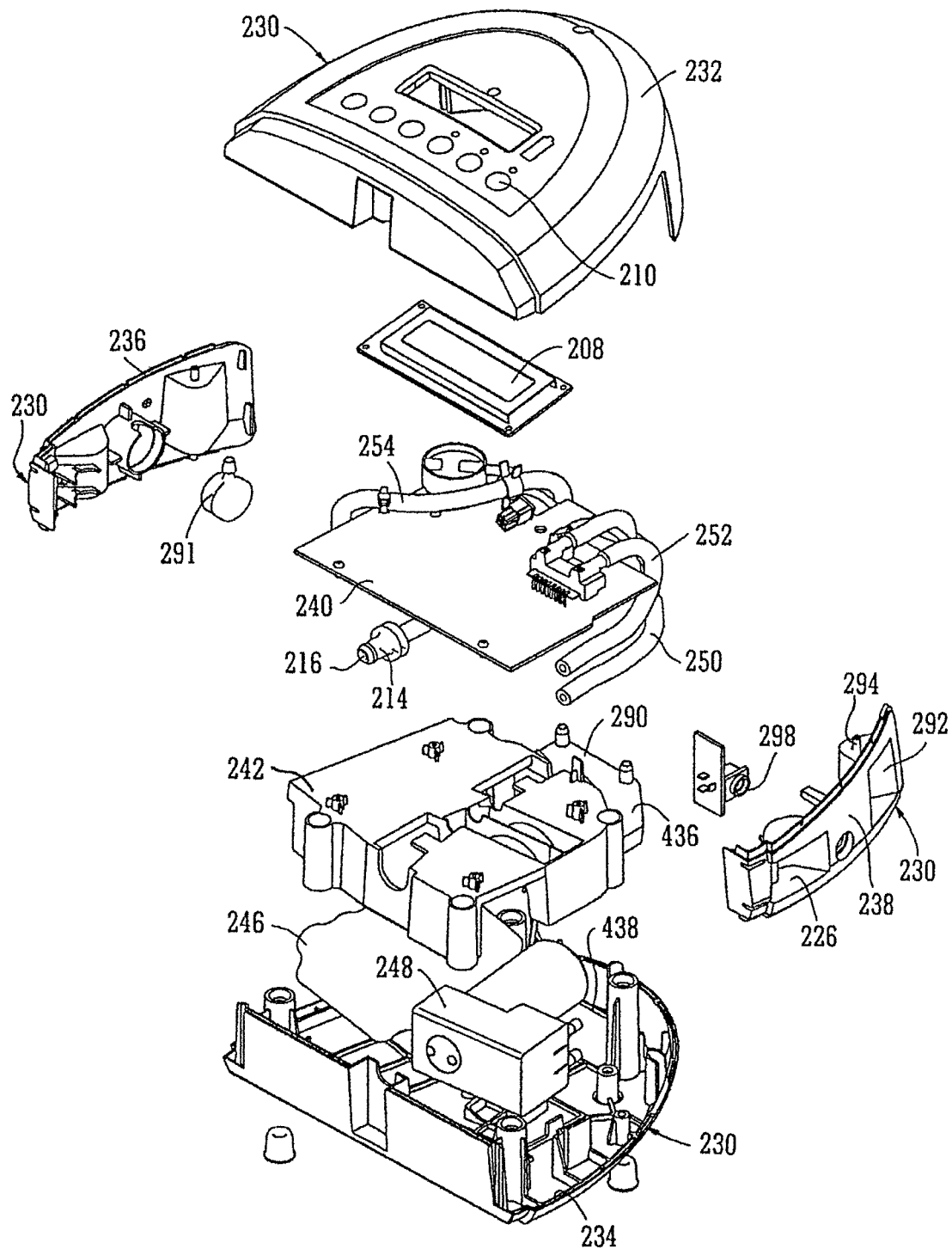
FIG. 7 shows an exploded view of the device unit of FIG. 6.

FIG. 4 shows the device 32 part of the apparatus according to some embodiments and the data paths employed in the control system for control of the aspirant pump and other features of the apparatus. A key purpose of the TNP system is to apply negative pressure wound therapy. This is accomplished via the pressure control system which includes the pump and a pump control system. The pump applies negative pressure; the pressure control system gives feedback on the pressure at the pump head to the control system; the pump control varies the pump speed based on the difference between the target pressure and the actual pressure at the pump head. In order to improve accuracy of pump speed and hence provide smoother and more accurate application of the negative pressure at a wound site, the pump is controlled by an auxiliary control system. The pump is from time to time allowed to "free-wheel" during its duty cycle by turning off the voltage applied to it. The spinning motor causes a "back electro-motive force" or BEMF to be generated. This BEMF can be monitored and can be used to provide an accurate measure of pump speed. The speed can thus be adjusted more accurately than can prior art pump systems.

According to some embodiments, actual pressure at a wound site is not determined but the difference between a measured pressure (at the pump) and the wound pressure is minimized by the use of large filters and large bore tubes wherever practical. If the pressure control determines that the pressure at the pump head is greater than a target pressure (closer to atmospheric pressure) for a period of time, the device sends an alarm and displays a message alerting the user to a potential problem such as a leak.

In addition to pressure control a separate flow control system can be provided. Flow rate can be determined and is used to detect when a canister is full or the tube has become blocked. If the flow falls below a certain threshold, the device sounds an alarm and displays a message alerting a user to the potential blockage or full canister.

Referring particularly to FIG. 4, in one embodiment, a pseudocode for monitoring the condition of filing of the waste canister 22 comprises the sequence of software steps:

```
1)   Check for blockage
     i)    Get Pressure value p(current)
     ii)   Get Flow Meter value f(current)
     iii)  If p(current) – p(set)   <   allowable pressure difference limit
              If f(current)   <   less than min. flow needed
                    sound buzzer
                    display "Blockage/Full" error message
2)   End Check for Blockage.
```

Where p(set) is a reference pressure for comparison with the p(current) pressure. Similarly, f(current) is the instantaneous measured flow rate and should be greater than a preset minimum flow rate under the given pressure conditions.

The above sequence of steps is repeated at a frequency of 200 Hz, however, the sensor may be sampled at a higher frequency and the signals averaged.

The control system 60 obtains the current pressure from the pressure monitor 46 and compares the current pressure with a predetermined value stored in the control system memory: if the difference between the two pressure values is less than predetermined limit and, if the flow rate is less than a predetermined minimum value also stored in the control system memory, then the control system will activate one or more of the alarms included in the device.

Figure 8:
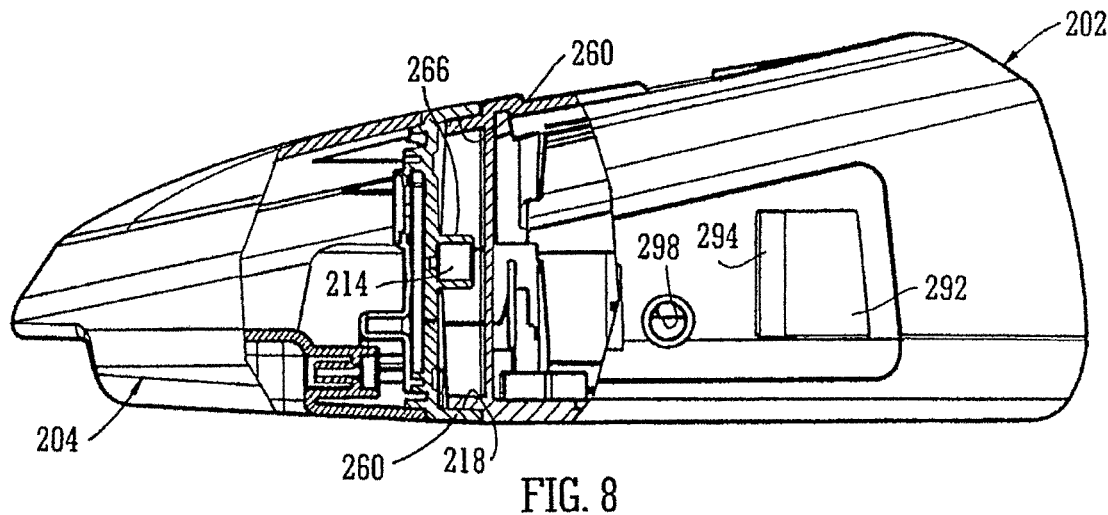
FIG. 8 shows a partially sectioned side elevation view through the interface between a waste canister and device unit of the apparatus.
Figure 9:
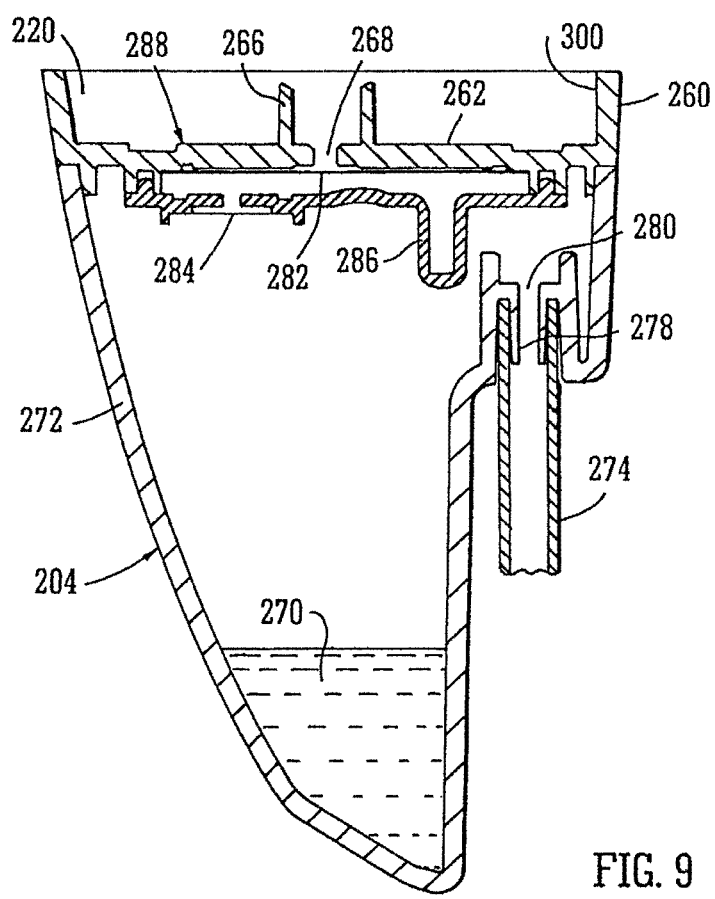
FIG. 9 shows a cross section through a waste canister of the apparatus of FIGS. 5 to 8.

Referring now to FIGS. 5 to 9 which show various views and cross sections of a preferred embodiment of apparatus 200 according to some embodiments. The preferred embodiment is of generally oval shape in plan and comprises a device unit 202 and a waste canister 204 connected together by catch arrangements 206. The device unit 202 has a liquid crystal display (LCD) 208, which gives text based feedback on the wound therapy being applied, and a membrane keypad 210, the LCD being visible through the membrane of the keypad to enable a user to adjust or set the therapy to be applied to the wound (not shown). The device has a lower, generally transverse face 212 in the center of which is a spigot 214 which forms the suction/entry port 216 to which the aspiration means (to be described below) are connected within the device unit. The lower edge of the device unit is provided with a rebated peripheral male mating face 218 which engages with a co-operating peripheral female formation 220 on an upper edge of the waste canister 204 (see FIGS. 8 and 9). On each side of the device 202, clips 222 hinged to the canister 204 have an engaging finger (not shown) which co-operates with formations in recesses 226 in the body of the device unit. From FIG. 7 it may be seen that the casing 230 of the device unit is of largely "clamshell" construction comprising front and back mouldings 232, 234, respectively and left-hand and right-hand side inserts 236, 238. Inside the casing 230 is a central chassis 240 which is fastened to an internal moulded structural member 242 and which chassis acts as a mounting for the electrical circuitry and components and also retains the battery pack 246 and aspiration pump unit 248. Various tubing items 250, 252, 254 connect the pump unit 248 and suction/entry port 216 to a final gaseous exhaust via a filter 290. FIG. 8 shows a partially sectioned side elevation of the apparatus 200, the partial section being around the junction between the device unit 202 and the waste canister 204, a cross section of which is shown at FIG. 9. These views show the rebated edge 218 of the male formation on the device unit co-operating with the female portion 220 defined by an upstanding flange 260 around the top face 262 of the waste canister 204. When the waste canister is joined to the device unit, the spigot 214 which has an "O" ring seal 264 therearound sealingly engages with a cylindrical tube portion 266 formed around an exhaust/exit port 268 in the waste canister. The spigot 214 of the device is not rigidly fixed to the device casing but is allowed to "float" or move in its location features in the casing to permit the spigot 214 and seal 264 to move to form the best seal with the bore of the cylindrical tube portion 266 on connection of the waste canister to the device unit. The waste canister 204 in FIG. 9 is shown in an upright orientation much as it would be when worn by a user. Thus, any exudate 270 would be in the bottom of the internal volume of waste receptacle portion 272. An aspiration conduit 274 is permanently affixed to an entry port spigot 278 defining an entry port 280 to receive fluid aspirated from a wound (not shown) via the conduit 274. Filter members 282 comprising a 0.2 µm filter and 284 comprising a 1 µm filter are located by a filter retainer moulding 286 adjacent a top closure member or bulkhead 288 the filter members preventing any liquid or bacteria from being drawn out of the exhaust exit port 268 into the pump and aspiration path through to an exhaust and filter unit 290 which is connected to a casing outlet moulding at 291 via an exhaust tube (not shown) in casing side piece 236. The side pieces 236, 238 are provided with recesses 292 having support pins 294 therein to locate a carrying strap (not shown) for use by the patient. The side pieces 230 and canister 204 are also provided with features which prevent the canister and device from exhibiting a mutual "wobble" when connected together. Ribs (not shown) extending between the canister top closure member 288 and the inner face 300 of the upstanding flange 260 locate in grooves 302 in the device sidewalls when canister and device are connected. The casing 230 also houses all of the electrical equipment and control and power management features, the functioning of which was described briefly with respect to FIGS. 3 and 4 hereinabove. The side piece 238 is provided with a socket member 298 to receive a charging jack from an external mains powered battery charger (both not shown).

Figure 10:
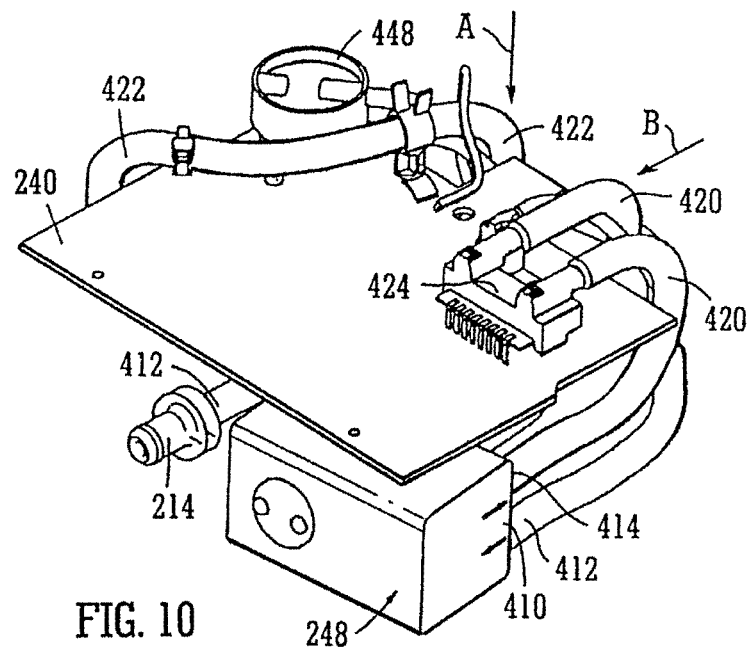
FIG. 10 shows a detail of a preferred embodiment of apparatus for the application TNP therapy and embodying functional elements of a control system for determining a waste canister full condition according to some embodiments.
Figure 11:
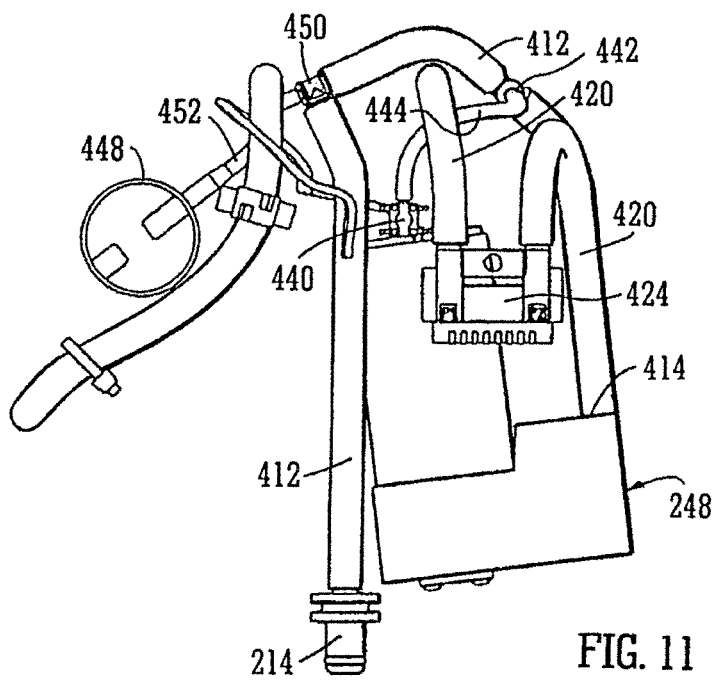
FIG. 11 which is a view of the apparatus of FIG. 10 in the direction of arrow A of FIG. 10 but with chassis plate omitted.
Figure 12:
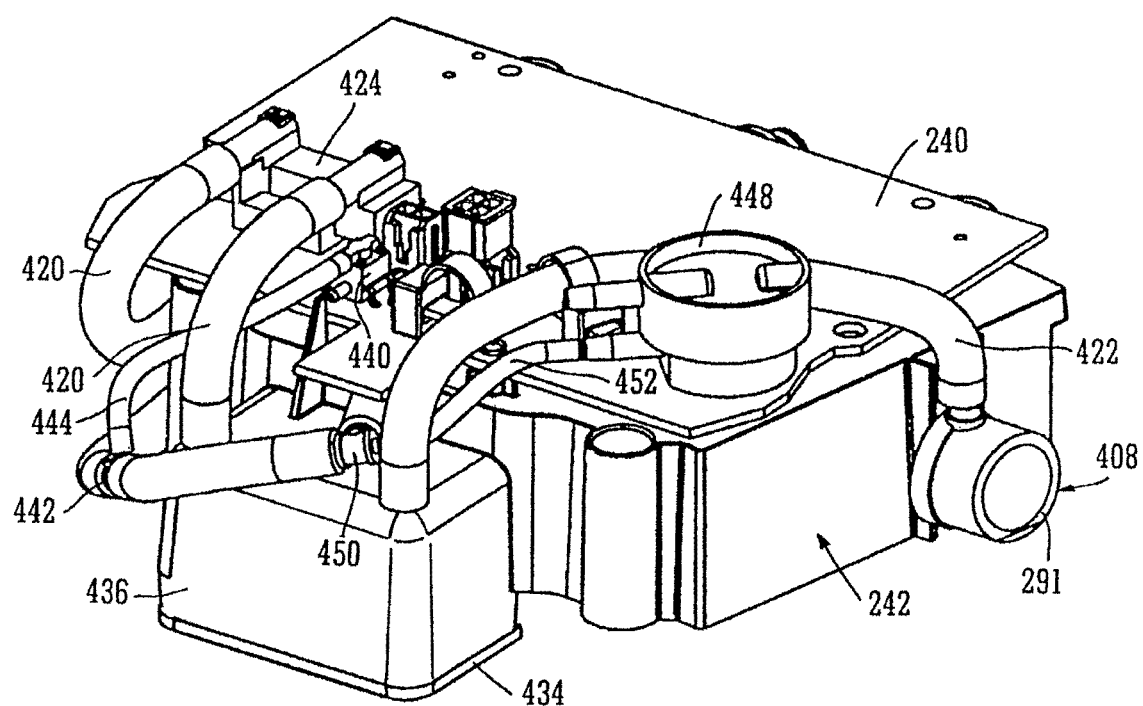
FIG. 12 which is a view of the apparatus of FIG. 10 in the direction of arrow B of FIG. 10.

Referring now to FIGS. 10 to 12 where a preferred embodiment of apparatus is described and the same features are denoted by common reference numerals.

Gaseous fluid exits from the waste canister 204 via spigot 214 into the gaseous fluid flow path defined in its initial stage to the pump 248 inlet port 410 by conduit 412 attached to the spigot 214. A silencing system is provided between the pump outlet port 414 and the exhaust outlet 408. A first exhaust conduit portion 420 is provided between the pump outlet port 414 and a plenum chamber 404; and, a second exhaust conduit portion 422 between the plenum chamber 404 and the exhaust outlet 408. However, the first exhaust conduit portion 420 is provided with a flow meter 424 intermediate its ends at the pump outlet 414 and an inlet 426 of the plenum chamber 404. A pressure sensing device 440 is connected to the first conduit portion 412 by means of a T-piece 442 and conduit 444. Similarly a pressure relief valve 448 is connected into the first exhaust conduit portion 412 also by a T-piece 450 and conduit 452. The pressure relief valve 448 is a safety device for preventing excessive negative pressures from being applied by the apparatus to the wound of user. The flow meter 424 is provided to fulfil various control functions including determining when the waste canister 204 is full. Since it is necessary that the fluid flow values measured by the flow meter 424 are accurate it is preferably positioned in the first conduit portion 420 rather than the second conduit portion 422 in case the plenum chamber 404 should leak for any reason and cause spurious flow measurements. However, other than this reason, the flow meter 424 could be positioned in the second conduit portion 422. The flow meter 424 and the pressure sensing device 440 are both connected electrically to the control system described hereinabove with reference to FIGS. 3 and 4. The second exhaust conduit portion 422 is connected to an outlet 430 of the plenum chamber 404 and the exhaust outlet 408. At the exhaust outlet 408, the second exhaust conduit portion 422 is connected to the moulding 291 which locates in the outer casing side piece 236 described with reference to FIG. 7 hereinabove. The moulding 291 may contain a final diffuser element such as an open-pore foam pad (not shown) to further break up any remaining sound waves which reach the outlet 408, however, such a foam pad may not be employed as the first and second exhaust conduit portions and the plenum chamber are generally sufficient to reduce the exhaust noise level to an acceptably low level. The plenum chamber 404 comprises a rectangular box-like structure 436 having a lower open face 432 and inlet 426 and outlet 430 and is fixed to the moulded structural member 242. A sealing gasket 434 is provided to engage with an outer rim defining the open face 432. When the complete device 230 is assembled, the rear outer case member 234 (see FIG. 7) has an upstanding rectangular rim 438 which both receives the sealing gasket 434 therein and also the rim defining the lower open face 432 of the plenum chamber 404. Thus when the front and rear casing members 232, 234 are fixed together such as by screws (not shown), for example, the sealing gasket 43 is squeezed between the outer casing member 234 and the rim defining the open face 432 to completely seal the plenum chamber 404. Before assembly the internal volume of the plenum chamber box 436 is filled with fibrous or porous sound absorbing material (not shown) which also serves as an odour filter by virtue of being impregnated with a suitable material such as activated charcoal, for example. The sound absorbing and odour filtering material serves to break up sound waves as they bounce back and forth between opposing walls of the box-like structure 436.

Figure 13:
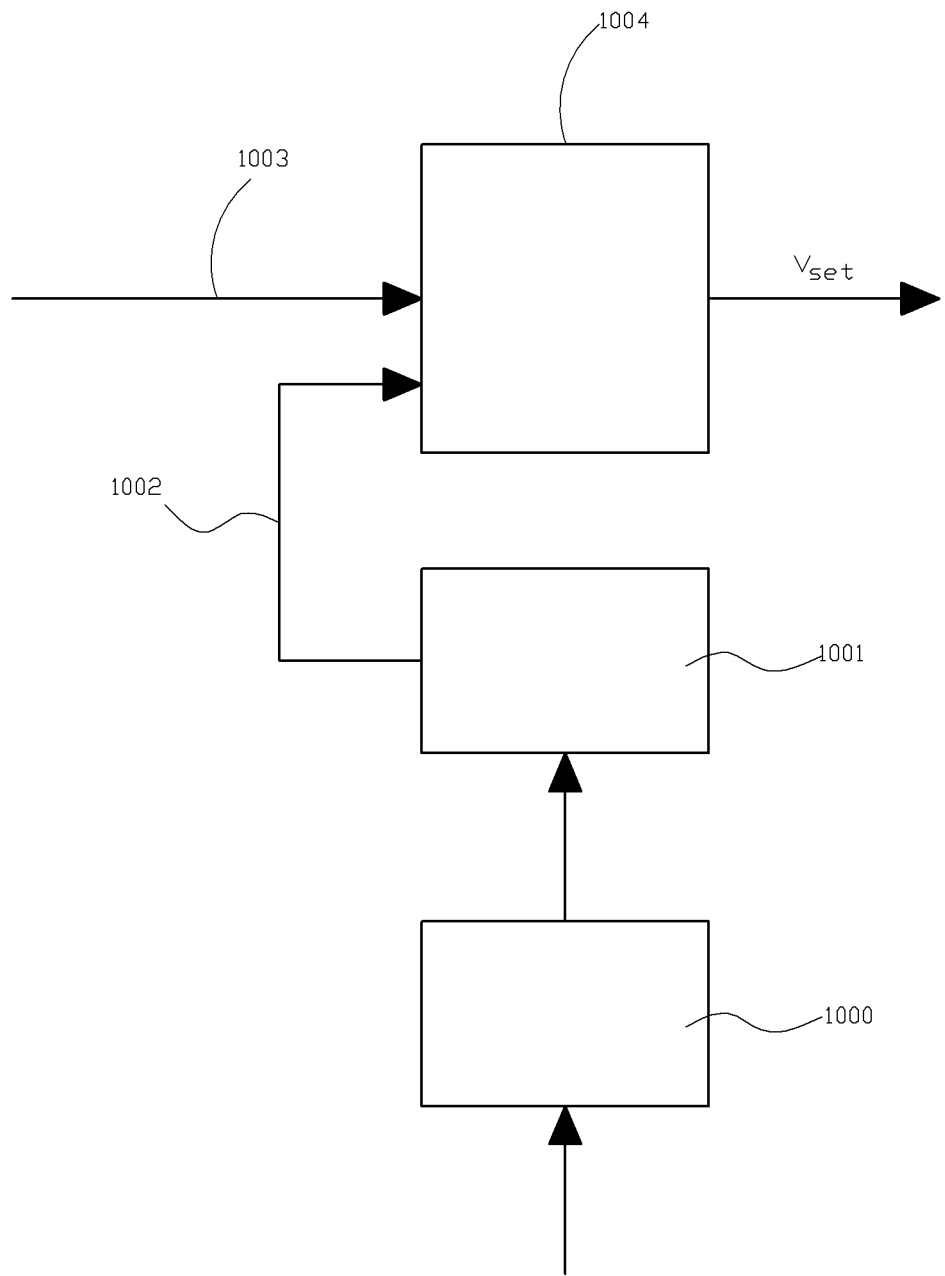
FIG. 13 illustrates how pump speed can be measured and selected.
Figure 14:
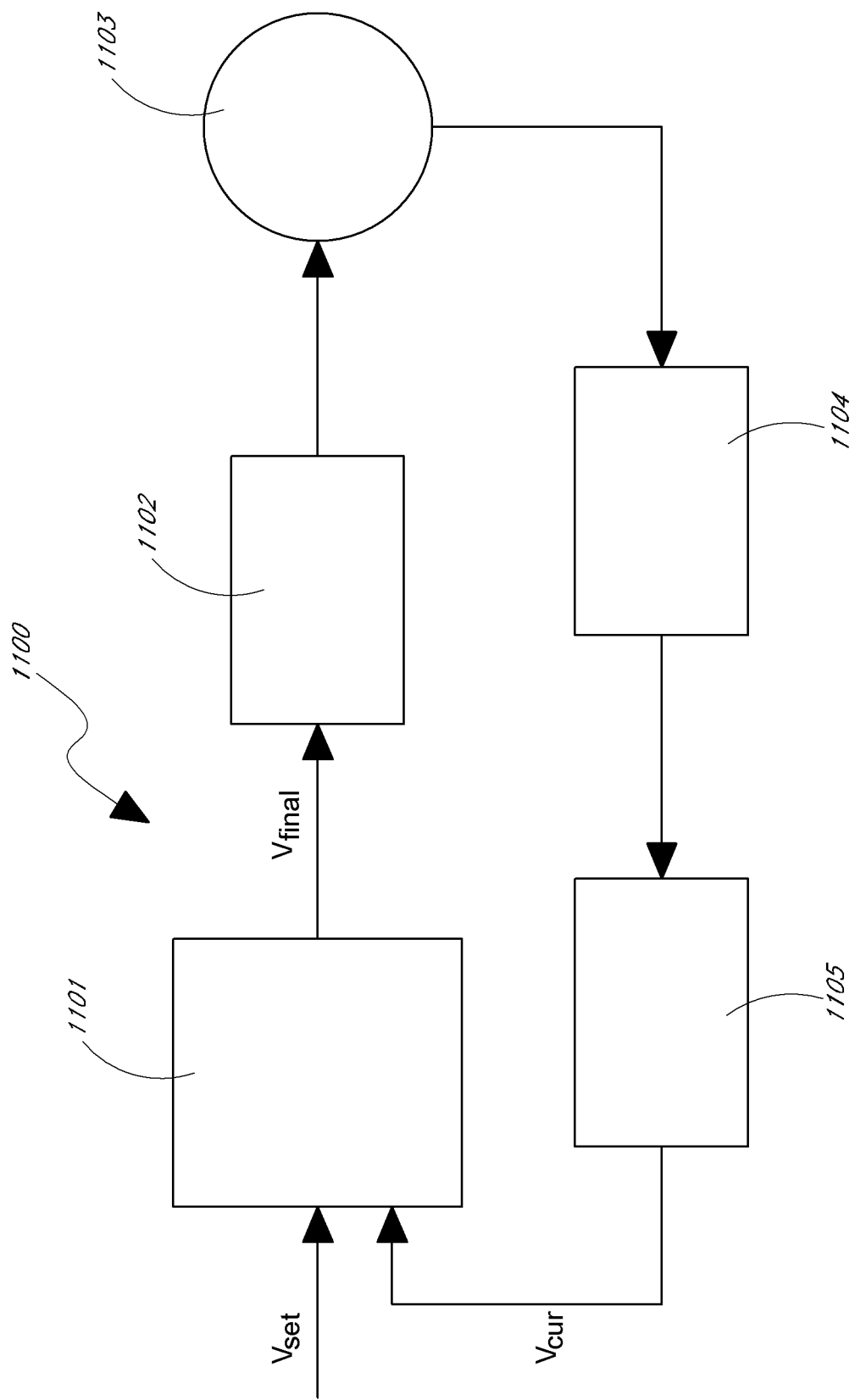
FIG. 14 illustrates how pressure generated by a pump can be controlled.

FIGS. 13 and 14 illustrate how the pressure provided by a pump of the TNP system can be set, monitored and controlled according to an embodiment. As illustrated in FIG. 13 a pressure sensor such as a pressure transducer is utilized to measure actual pressure at a pump inlet, which during use will be located at or close to a wound site. It will be appreciated that according to some embodiments the pressure sensor may be located at some predetermined location along the tube connecting the device unit to the wound site.

Pumping pressure is controlled by an initial pump speed setting system which measures pressure and sets a desired pump speed responsive to the measured pressure and a predetermined pressure set by a user, and a further control loop system in which actual pump speed is monitored and compared with the determined pump speed. Pumping is actually controlled responsive to the comparison.

As illustrated in FIG. 13 the pressure determined by the sensor is converted into a digital value in an analogue digital converter 1000 and the value scaled to thereby filter pressure reading before being fed into the control loop to thereby minimise the effect of noise in the reading thereby reducing jitter. This also helps minimise false alarms due to over or under pressure situations.

Pump speed control is achieved by implementing a control loop in hardware or software. The measured scaled pressure provides an input 1002 into the pressure controller whilst a further input 1003 is provided by a user entering a desired pressure via a user interface. The pressure controller 1004 takes the pressure set point and the actual measure of pressure as inputs to deliver a new desired pump speed as its output Vset. The measured pressure values from the pressure transducer are averaged over a certain number of previous readings before feeding a value to the control loop. This minimises jitter and noise and serves as a first dampener of pump response.

The control sequence used for controlling pump response is given below:

| | |
|---|---|
| Defines >>> | Constants for control loop: kp, ki, t |
| | Bounds for output: Vmax, Vmin |
| Inputs >>> | Current pressure value: pv, |
| | Set point value: sp |
| | Calculate difference: e = sp − pv |
| | P = kp * e |
| | I = I + ki * e * t |
| | Verify I is between the Vmin and V max bounds |
| | V = P + I |
| | Verify V is between the Vmin and V max bounds |

Thus the difference between the measured pressure and a desired pressure is calculated and then scaled using experimentally predetermined constants to yield the output value of pump speed Vset. The constants are optimised for best pump response and to minimise pressure overshoot or undershoot. The scaling further dampens the effect of the current pressure difference by taking into account a certain number of previous pressure differences. The control loop is provided to allow only a certain maximum step change in pressure at a time by bounding the output pump speed value within predetermined sensible limits. Thus a sudden change in measured pressure (due to any reason for example the user changing position) or a change in the pressure set point is fed back to the pump drive circuitry incrementally in small steps rather than as a dramatic change.

This mechanism of pump speed control thus results in a better reaction to rapid changes in pressure as the pump does not instantly 'overreact'. Since the pump does not have a drastic reaction to pressure changes the overall 'perceived' noise levels are lower. Gradual adjustment of pump speed also results in lower pump wear and tear which enhances device performance and longevity. Furthermore averaging the pressure transducer readings before feeding them to the control loop reduces the likelihood of false alarms with respect to over or under pressure situations.

FIG. 14 illustrates how accurate speed control of a suction pump on the TNP device allows fine control of a negative pressure applied at a wound site and which thus helps reduce noise during device operation and minimises discomfort to the user. The system provides a control loop that periodically turns off power to a pump motor and records an electromotive force (EMF) generated by a freewheeling element such as a rotor of the pump. The measured EMF is used to calculate the actual pump speed and drive signals supplied to the pump can thus be modified to accurately achieve a desired speed.

As illustrated in FIG. 14 a control loop 1100 uses the desired and actual pump speeds at a given instant to accurately determine the drive voltage that needs to be applied to the pump in order to accurately achieve final desired speed and thus pressure. The control loop operates by calculating the difference between the desired speed Vset and the current speed Vcur. The pump controller 1101 scales the difference and optionally accumulates the scaled differences from a certain number of previous iterations. The control loop 1101 outputs a value Vfinal for the pump drive voltage that leads to the pump achieving its final desired speed. The scaling constants for the control are determined experimentally prior to operation to ensure acceptable performance of the device (ie. ability to maintain set pressure at specified wound leak rates). The scaling constants can be calculated in various ways however aptly on start-up conditions to provide a predetermined pressure can be applied. A measured actual pressure will indicate operational parameters indicative of pressure change, leaks, wound size and volumes in the waste canister. Scaling constants are then set responsive to these.

The pump control system is responsible for maintaining the pump speed which in turn drives the pressure generated at the wound. The motor speed is controlled by varying a pulse width modulation (PWM) input. The duty cycle of the PWM generator 1102 is controlled responsive to the drive voltage signal Vfinal and the output of the PWM generator is utilized to drive the pump 1103.

The actual speed of the pump is obtained by measuring the terminal voltage across the pump with the current at zero. This is achieved by intermittently turning the pump power off by controlling the PWM generator output. Subsequent to turn off a short period is allowed to wait for the EMF of the freewheeling pump to settle during a certain predetermined time period and thereafter the steady value of the EMF is sampled. This EMF is a direct measure of pump shaft speed. The EMF generated is converted into a digital signal via an analogue digital converter 1104 and then scaled with a scaling unit 1105. The EMF sampling rate is varied according to pump speed to counter the aliasing and to minimise the effect on pump speed. The EMF sampling rate may be reduced at higher pump speed since the inertia of the pump maintains a more constant motion at high pump speeds.

Operation of the control utilized can be summarised by the following control sequence:

```
Pump_Speed_Controller
    Turn pump_enable and PWM off
    Turn pump_enable on after current drops
    Allow EMF to settle
    Sample EMF and estimate current speed (Vcur)
    new_PWM = PI (Vset, Vcur)
    Enable pump PWM
    New pump duty cycle = new_PWM
End Motor_Controller
PI (Vset, Vcur)
    Defines >>    constants kp, ki, t
    Inputs >>     current motor speed Vcur
                  Desired motor speed Vset
    Calculate difference: e = Vset − Vcur
    P = kp * e
    I = I + ki * e * t
End PI
```

Accurate pump control results in overall lower noise levels during device operation. Specifically abrupt changes in noise are avoided because the pump speed is adjusted frequently and in small steps. Maintaining accurate control of pump speeds can extend pump and battery life. Moreover a steady pump delivers a steady negative pressure thereby minimising patient discomfort.

Figure 15:
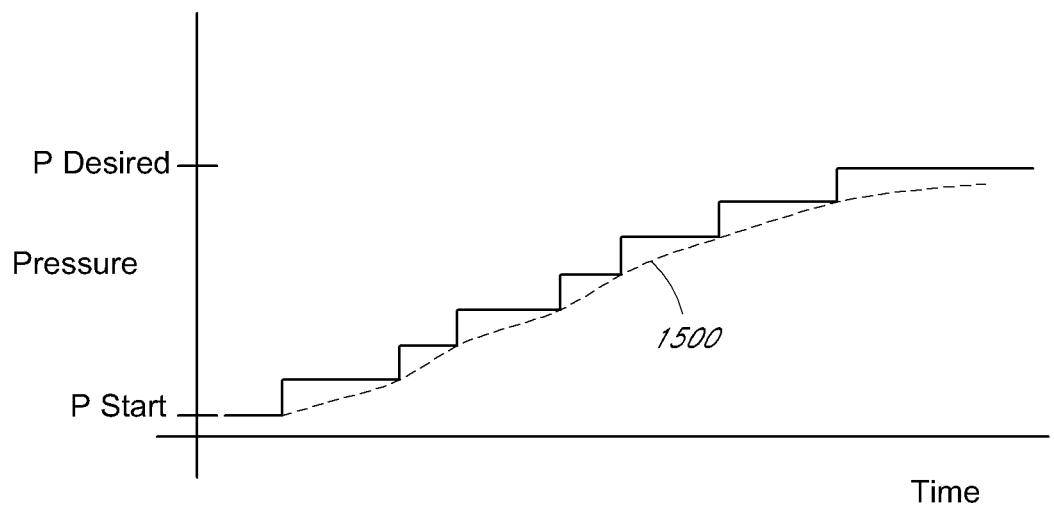
FIG. 15 illustrates how pressure can be increased.

FIG. 15 illustrates how pressure supplied by a TNP system may be determined according to some embodiments. It will be appreciated that whilst some embodiments refer to the determination of pressure other parameters such as flow rate etc. can be controlled in a similar manner according to other embodiments.

In contrast to prior known techniques in which pressure supplied by a TNP system is varied from a current value to a desired value as a 'ramp rate' variation, some embodiments vary pressure in a step wise manner. A set pressure is thus incremented only when the system confirms that the current set pressure has been achieved by the pump. This leads to the pump control system attempting to 'keep up' with a changing set point until it reaches a new required pressure. It will be appreciated that whilst some embodiments relate to the increase of pressure from a current value to a desired value, the other embodiments also permit decreases in pressure to likewise be controlled.

FIG. 15 illustrates how a current pressure illustrated by the dotted line 1500 may be increased from a starting pressure $P_{start}$ to a desired pressure $P_{desired}$. The desired pressure may be input by a user using a user interface or may represent a predetermined value stored in a data store of the TNP system or coded in software. Such a value is particularly helpful on start up of the TNP system. The TNP system uses a feedback control loop to achieve and maintain the set pressures. The control loop calculates a pump speed necessary to achieve a certain pressure by measuring current pressure and calculating the difference between a new pressure and a current pressure. For example when the user changes the set point via a user interface or the device operates on start up, the TNP system determines at least one intermediate step value between the starting pressure and the final desired pressure. The one or more step values are fed to a control loop so that device pressure is increased incrementally rather than attempting to bridge the pressure difference in one big step.

As illustrated in FIG. 15 the stepped values are predefined as uniform increments. It will be appreciated that alternatively the new target pressure value intermediate the start and desired pressure values can be calculated for each change in set pressure based upon the gap to be bridged. FIG. 15 illustrates a schematic trace with the set pressure providing a target pressure for the control system incrementing (solid line) whilst the actual control system pressure provided continually 'catches up'.

Figure 16:
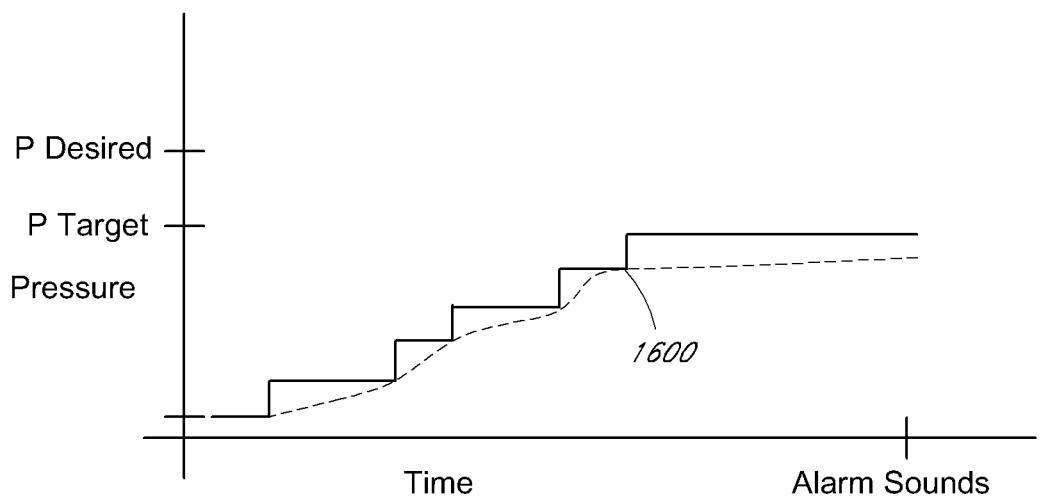
FIG. 16 illustrates how a leak may be detected.

FIG. 16 illustrates how some embodiments can be utilized to promptly detect a leak or some other such problem associated with the TNP system. At any time if the pump is not able to meet a desired step change in pressure a possible leak can be flagged. For example as shown in FIG. 16 an intermediate target pressure $P_{target}$ is set as the pressure is being increased to the desired pressure $P_{desired}$. However FIG. 16 illustrates when a leak has occurred in the TNP system how a current pressure indicated by the dotted line does not attain an intermediate target pressure. When this occurs the TNP system can issue an audible and/or visible alarm cue to indicate that a problem has occurred. The alarm is initiated a predetermined time subsequent to a new target pressure being set. This potentially allows for early detection of leaks as a failure to achieve anyone of the temporary 'target pressures' will trigger an alarm rather than only failure to achieve a final operating pressure $P_{desired}$.

Figure 17:
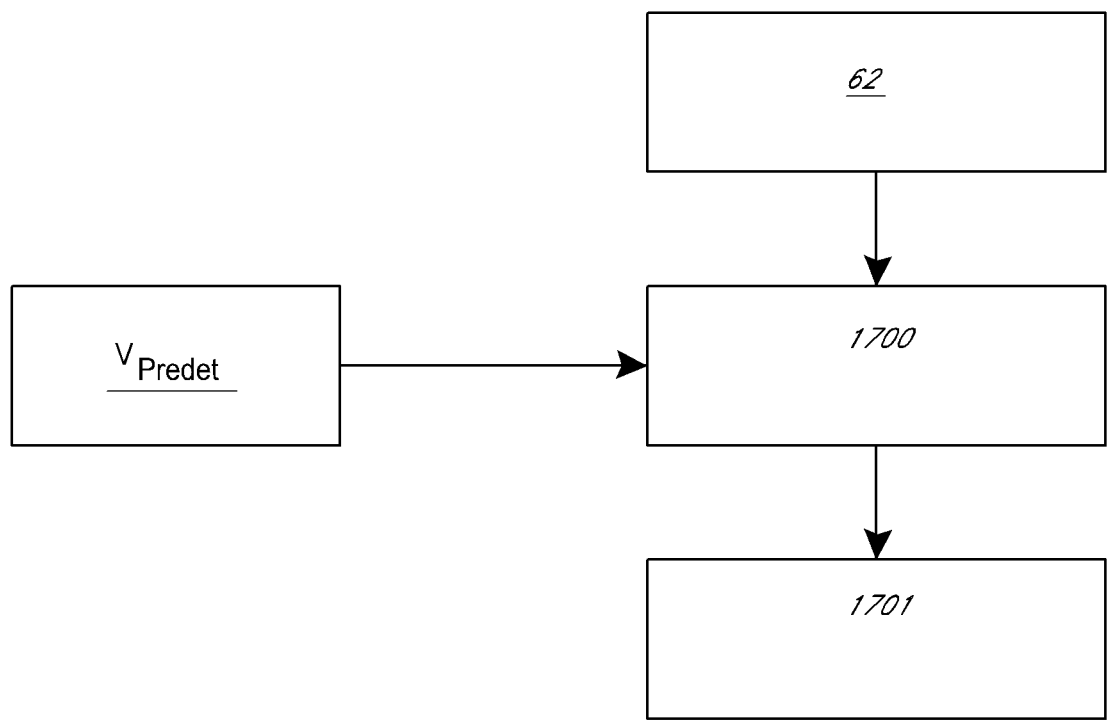
FIG. 17 illustrates pressure control.

FIG. 17 illustrates how some embodiments control the setting and control the pressure may be provided in software 1700 of the TNP system. It will be understood that some embodiments can be alternatively or additionally provided in hardware. When the user changes a set point via a user interface 62 or when a predetermined value $V_{predet}$ is initiated on start up these values are provided as a desired pressure value to the software of the TNP system. The software controls the pressure control system 1701 according to the methodology set out below:

```
Change_SetPoint
        Input: current_Setpt, new_Setpt
        Define: num_Increments
    Step = abs (new_Setpt − current_Setpt)/num_Increments
    For i=1, i< Num_Increments; ++ i
        incremental_pressure = current_setpt + i*step
        Call PI Loop( ) to set to incremental_pressure
        if PI Loop is no successful, flag a Leak
    End For
End Change_SetPoint
```

It will be appreciated by those skilled in the art that tuning of the control loop becomes far more predictable according to some embodiments when compared to prior art TNP systems. This is because operation is carried out over a narrower range of pressure differences i.e. over each incremental step as opposed to a full range selected by a user.

Figure 18A:
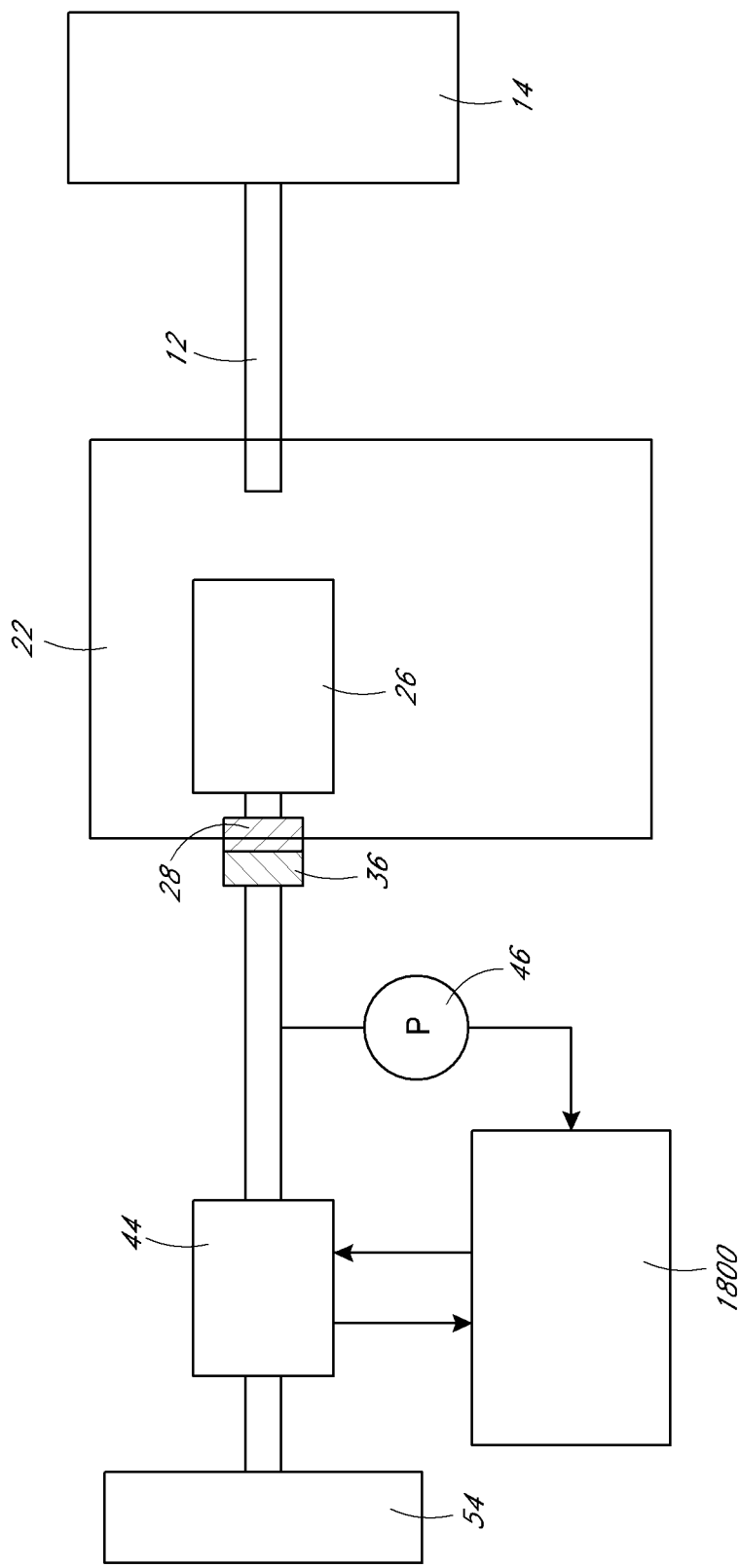
FIG. 18A illustrates how flow rate may be calculated without a flow meter.

FIG. 18A illustrates how some embodiments can determine a flow rate in a flow path without the need to include a flow meter in a TNP system according to some embodiments. It will be appreciated that a pressure sensor 46 and pump 44 will often be included in a TNP system and therefore a mechanism for determining flow rate without need for an expensive flow meter utilizing units already included in a TNP design produce a favorable system. The system measures the pressure at a pump inlet or some other such desired location as well as determining the speed of the pump via measurement of a back EMF. A known relationship between pump speed, pressure and flow rate can then be used to calculate the flow rate at a location where the pressure sensor is located. Particularly high or low flow rates can be utilized to trigger an alarm condition.

Figure 18B:
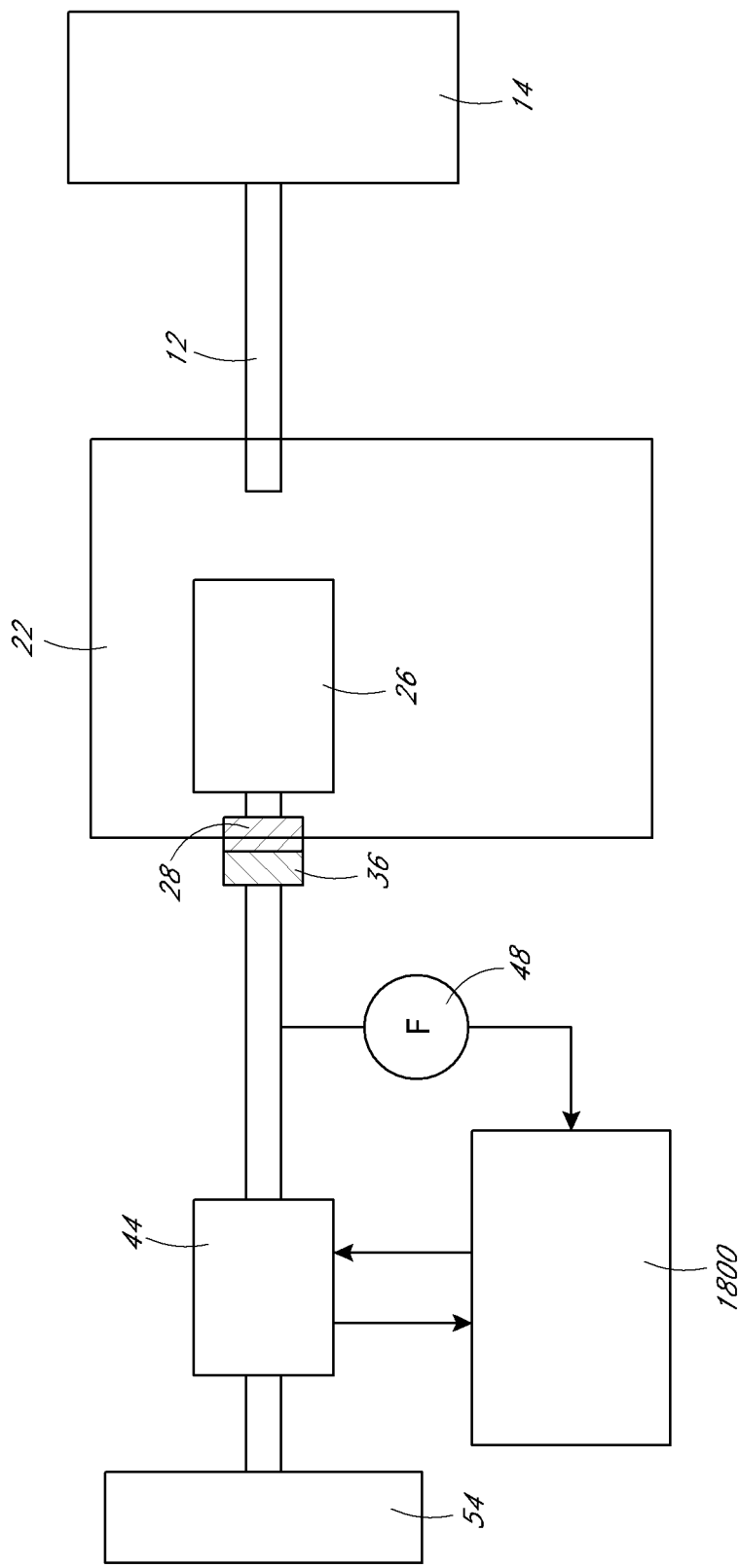
FIG. 18B illustrates how pressure may be calculated without a pressure sensor.

FIG. 18B illustrates how some embodiments can determine a pressure in a flow path without the need to include a pressure sensor in a TNP system according to some embodiments. It will be appreciated that a flow meter 48 and pump 44 will often be included in a TNP system and therefore a mechanism for determining pressure without the need for an expensive pressure sensor utilizing units already included in a TNP design produce a favorable system. The system measures the flow rate at a pump inlet or some other such desired location as well as determining the speed of the pump via measurement of a back EMF. A known relationship between the pump speed, pressure and flow rate can then be used to calculate the pressure at a location where the flow meter is located. Particularly high or low pressures can be utilized to trigger an alarm condition.

As illustrated in FIG. 18A and 18B the TNP wound care system includes a pump 44 required to provide the negative pressure. As noted previously, the back EMF of the pump can be determined during a free-wheeling mode of operation and the voltage generated is known to be directly proportional to the operating speed of the pump. The operating speed of the pump can thus be measured during device operation.

Again, as noted above, the pump is kept at a proper operating speed using a feedback mechanism including a feedback system 1800 which utilizes the measured back EMF as an indication of current pump speed. If a problem occurs with the system, for example a leak occurs, the feedback mechanism detects this as a decrease in pressure or in flow rate. The feedback mechanism increases the voltage to the pump to compensate. As the voltage increases, the back EMF will increase in time. The back EMF indicates pumping frequency. This pump frequency, along with the inlet pressure, can be used as a direct indication of system leaks (flow rate).

Figure 19A:
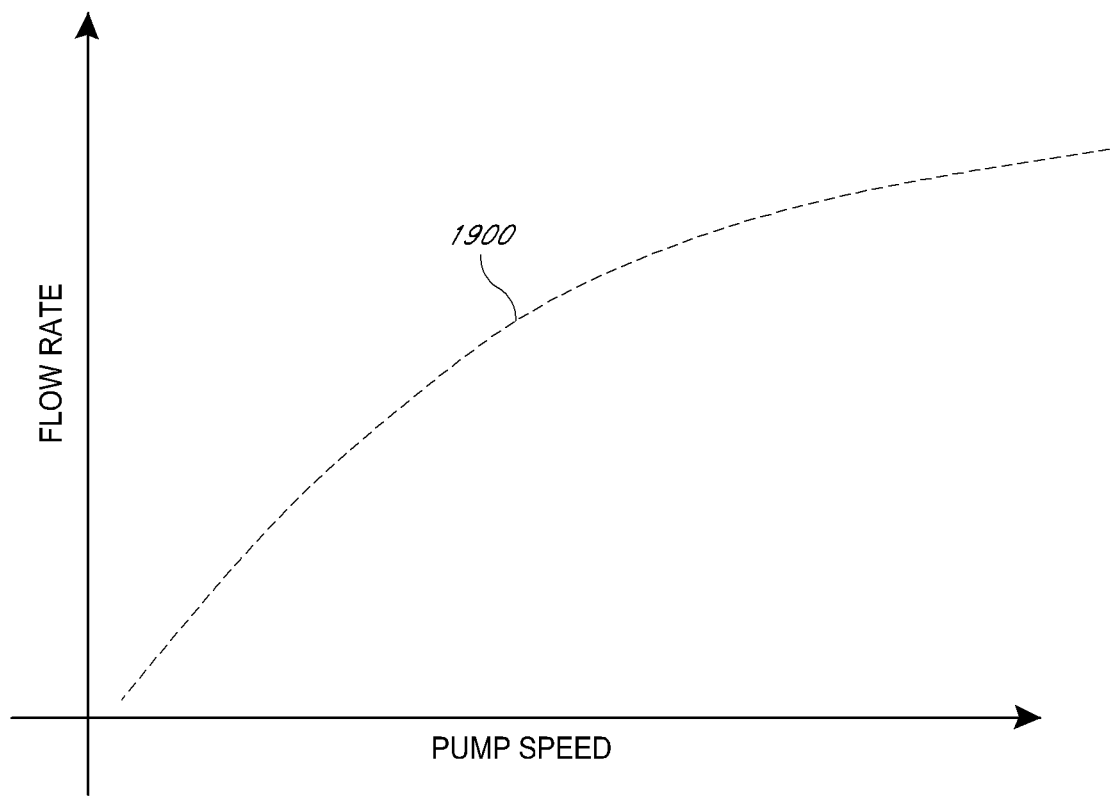
FIGS. 19A-19B illustrate relationships between flow rate, pressure, and pump speed.

FIG. 19A illustrates a known relationship between pump speed, flow rate and pressure difference. Here it will be understood that the pressure difference is the absolute pressure (or vacuum) achieved from atmospheric conditions. It will be appreciated that the particular relationship will be dependent upon the characteristics of the pump system and TNP system generally. To calculate a flow rate from an available pressure and pump speed, or to calculate a pressure from an available flow rate and pump speed, some embodiments utilize a "look-up table". This table is predetermined experimentally during set up or product development. The look-up tables are stored as data in a data store or are set out in software utilized by the TNP system.

As illustrated in FIG. 19A, for any TNP system a range of values indicating a predetermined relationship 1900 for flow rate can be determined as pump speed varies. This is for a single preset fixed pressure. Similar relationship curves 1900 indicating how flow rate varies with any particular pump speed are determined for many possible fixed pressure values or ranges during TNP system design.

As a result the pressure determined during use by a pressure sensor can be used to select from a look up table of possible pressure values a flow rate and pump speed relationship 1900 for that pressure or pressure range. A pump speed can then be compared to the range and a flow rate read off. It will be appreciated by those skilled in the art that rather than having a flow rate versus pump speed relationship stored in the look up table for a multitude of pressure ranges, a flow rate versus pressure relationship could alternatively be determined for fixed pump speeds. A pump speed would thus be utilized to select a specific look up table storing a relationship between flow rate and pressure.

Figure 19B:
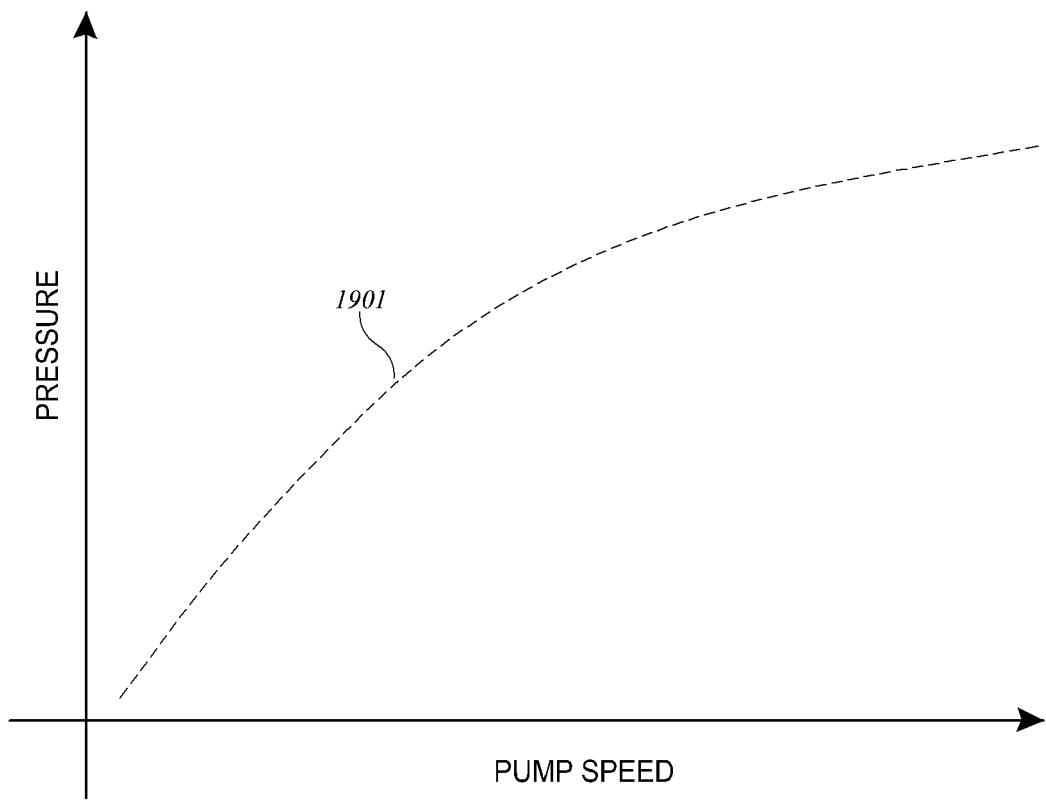

Also as illustrated in FIG. 19B, for any TNP system a range of values indicating a predetermined relationship 1901 for pressure can be determined as pump speed varies. This is for a single preset fixed flow rate. Similar relationship curves 1901 indicating how pressure varies with any particular pump speed are determined for many possible fixed flow rate values or ranges during TNP system design.

As a result the flow rate determined during use by a flow rate sensor can be used to select from a look-up table of possible flow rate values a pressure and pump speed relationship 1901 for that flow rate or flow rate range. A pump speed can then be compared to the range and a pressure read off. It will be appreciated by those skilled in the art that rather than having a pressure versus pump speed relationship stored in a look-up table for a multitude of flow rate ranges, a pressure versus flow rate relationship could alternatively be determined for fixed pump speeds. A pump speed would thus be utilized to select a specific look-up table storing a relationship between flow rate and pressure.

As indicated in FIGS. 19A and 19B, as a rough approximation the relationship between flow rate and pump speed for a fixed flow rate or pressure difference is linear at low pump speeds and then tends to flatten as the pump has a maximum flow rate it can maintain regardless of speed.

It will be appreciated that the flow meters or pressure sensors may be placed in alternative locations, such as in front of the canister or in front of the wound, to achieve pressure and flow rate calculations.

Some embodiments, which calculate flow rate without a flow meter, or pressure without a pressure meter can be utilized in conjunction with alternative pressure and flow measurements provided by pressure sensors or flow meters in the flow path of the TNP system as a safety back up. As a result, some embodiments provide increased user confidence and may be utilized to detect early leakages of dressings since pressure can be determined at a further location from where a pressure sensor is located and flow rate can be determined at a further location from where a flow meter is located. This can lead to reduced power usage which causes less drain on internal batteries and thus lowers cost.

Accurate pump control results in overall lower noise levels during device operation. Specifically abrupt changes in noise are avoided because the pump speed is adjusted frequently and in small steps. Maintaining accurate control of pump speeds can extend pump and battery life. Moreover a steady pump delivers a steady negative pressure thereby minimizing patient discomfort.

As an alternative to measuring pump speed via the establishment of a back EMF other methods could be adopted according to alternative embodiments. For example a speed sensor such as an optical tachometer or the like or other sensor type such as a Hall effect sensor able to determine speed could be included to determine pump speed.

Referring now to FIGS. 20A-20F and where the same or similar features are denoted by common reference numerals. In essence the same numerals notation as used in FIGS. 1 to 4 hereinabove is used for FIGS. 20A-20F except where they differ and which will be explained as appropriate.

Figure 20A:
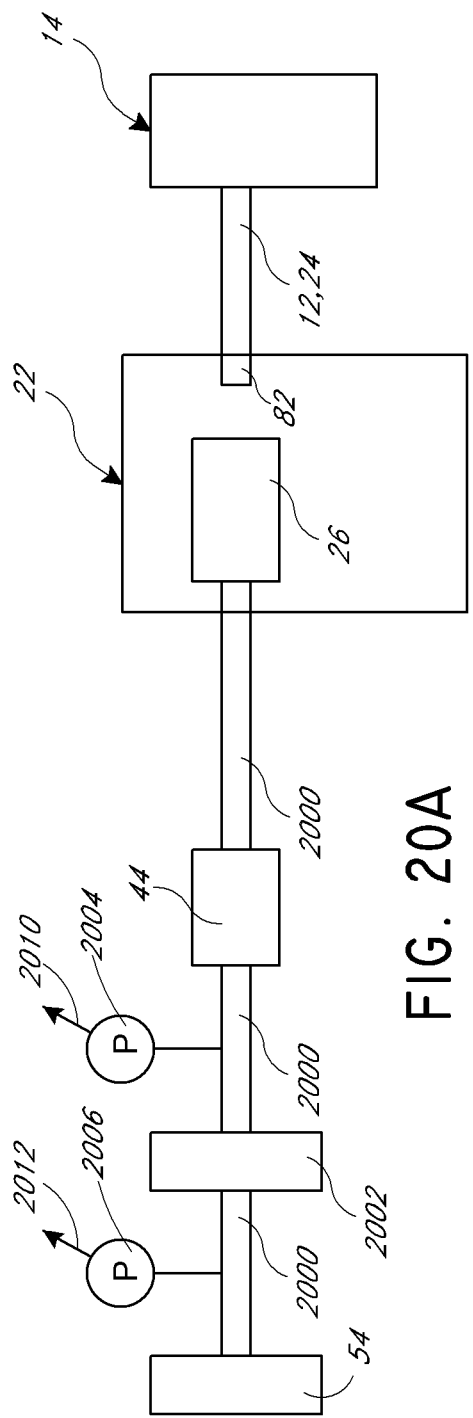

FIG. 20A shows a similar system to FIG. 1 comprising: a dressing 14; aspirant conduit 12, 24; waste canister 22 having filters 26 on an exit port thereof; internal tubing 2000 in the device 32 linking an aspirant vacuum pump 44 and an exhaust 54 (which may or may not have a filter therein).

However, in the illustrated embodiment of the apparatus, the flowmeter 48 of FIGS. 1 to 4 is replaced by a combination of a fluid flow restrictor 2002 and pressure sensors 2004, 2006. The flow in the fluid flow path from the canister downstream of the filters 26 to the exhaust 54 is essentially gaseous fluid flow since liquids and bacteria are retained in the waste canister by the filters 26. The fluid flow restrictor 2002 is a small aperture having a diameter in the range 0.1 to 0.5 mm in the fluid flow path intended to raise the pressure in the fluid on the upstream side of the restrictor relative to that on the downstream side under normal aspiration conditions when there is fluid flow through the system (up to the filter 26 the fluid is a mixture of gas and liquid). Pressure signals indicated by arrows 2010 and 2012 are communicated to the control system module 60 (see FIGS. 1 - 4) by the sensors 2004, 2006. When the pressure difference between sensors 2004, 2006 falls below a critical value stored in the memory of the control system 60 the control system recognizes this condition as a "blockage" and/or "canister full" condition and triggers a visual and/or audible alarm (not shown). The pseudo-code for the logic sequence has the form below:

```
Check for blockage
    Get pressure sensor value f (current)
        If f(current)< min pressure needed
            Sound buzzer
            Display "Blockage/Full" error message
End check for blockage.
```

Figure 20B:
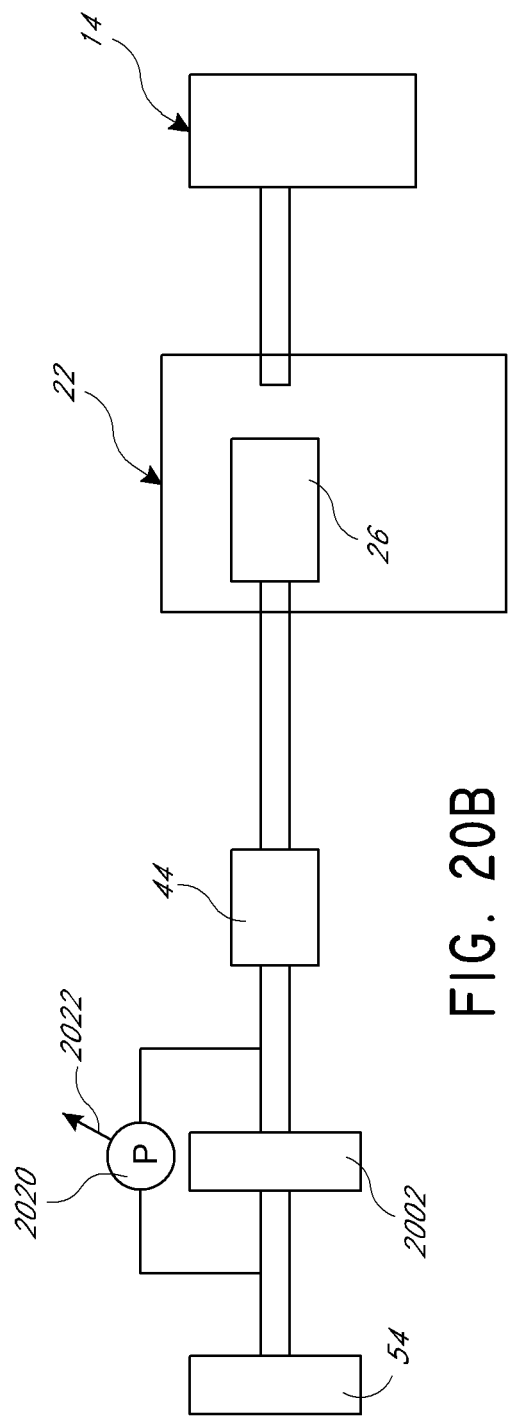

FIG. 20B shows a similar system to FIG. 20A but uses a single pressure monitor 2020 which monitors directly the pressure differential between the two positions upstream and downstream of the flow restrictor 2002. The control system works in the same manner being triggered by the sensor 2020 signals 2022 when a pressure difference below a pre-stored minimum is reached.

FIG. 20C shows a third embodiment where two pressures sensors 2040, 2042 are placed upstream of the pump 44 and between the pump 44 and flow restriction 2002. When the canister becomes full or the aspiration conduit blocked, pressure in the tubing 2000 will still be a negative pressure (below ambient atmospheric) and the pressure sensor 2040 will show a negative pressure. However, due to little or no flow of aspirant fluid through the pump 44, the pressure sensor 2042 will show effectively ambient atmospheric pressure which will pertain through the exhaust system to the exhaust aperture 54. Thus, if the pressure differential between sensors 2040 and 2042 signaled to the control system 60 is a negative differential the control system 60 will still activate the alarm. In reality the pressure differential is always likely to be negative since the pressure read by sensor 2040 will be in the region of −50 to −200 mm Hg, i.e. the negative pressure being applied at the wound site/dressing 14. The pressure in sensor 2042 may be in the range from 0 to 5 mm Hg. Thus, an alarm may be activated by the control system 60 when the pressure read by sensor 2042 approaches ambient indicating low to zero flow through the restrictor 2002.

FIG. 20D shows a fourth embodiment where the flow restrictor 2002 is placed between the canister 22 and pump 44 with pressure sensors 2050, 2052 placed between the canister and flow restrictor and between the flow restrictor and pump, respectively. When aspirant fluid flow through the restrictor 2002 falls to zero due to a full canister or blocked conduit, the two pressure sensors 2050, 2052 will both have the same reading albeit both reading a negative pressure as the pump is still running. Thus, equal or pressure signals less than a stored difference to the control system 60 will result in the alarm being activated.

Figure 20E:
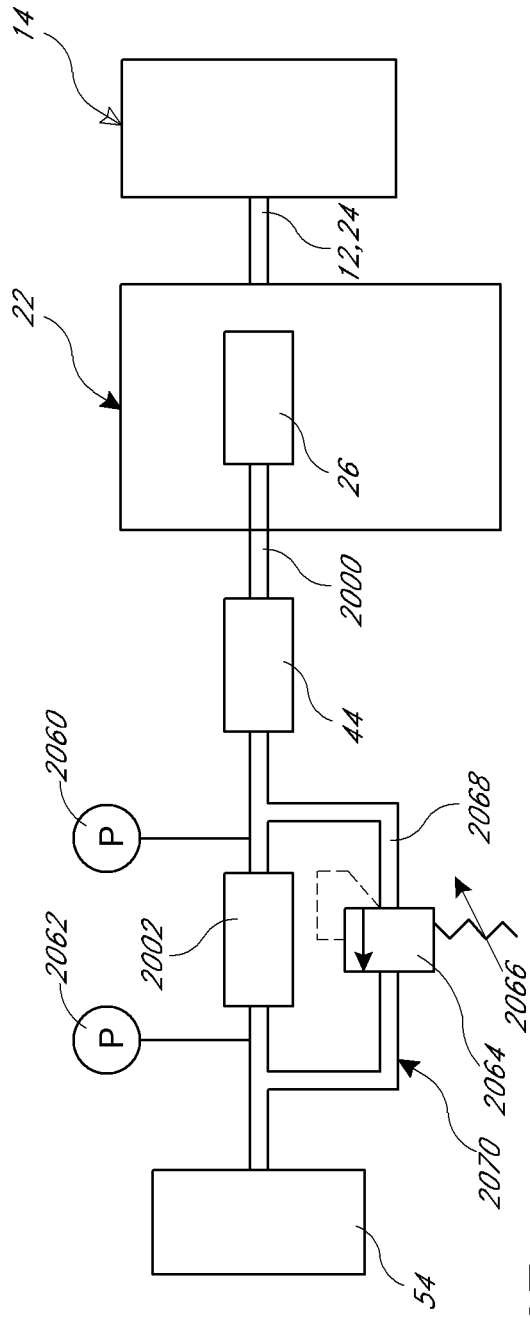

FIG. 20E shows a schematic diagram of a fifth embodiment where a flow restrictor 2002 is placed downstream of the pump 44 and which has pressure sensors 2060, 2062 placed either side as in FIG. 20A, for example, however, in this embodiment, there is a bypass conduit 2064 placed across the flow restrictor, the by-pass conduit 2064 having an adjustable pressure sensitive valve 2066 therein. The valve 2066 may be a simple, spring loaded device able to be set to open at a desired specific pressure. Thus, when, for example, there is relatively unrestricted fluid flow through the flow system in the overall apparatus due to the canister being less than full and the aspiration conduits 12, 24 being free and unblocked, the pump will have an unnecessary burden placed upon it due to the flow restrictor 2002 impeding flow and consequently the pump 44 will be operating inefficiently. Under these conditions pressure in the portion of the by-pass conduit 2068 will exceed a pressure set in the valve 2066 (for example +5 mm Hg) and the valve will consequently open to allow relatively unrestricted fluid flow through the valve 2066 into the downstream portion 2070 of the by-pass conduit 2064. The valve will operate to open and close so that pressure in the by-pass conduit portion 2068 is always at or slightly below the value set in the valve 2066. Under the circumstances when the flow of aspirant fluid starts to deteriorate sufficiently due to the aspirant conduit 12, 24 becoming blocked or the canister approaching full, the pressure in the by-pass conduit portion 2068 will fall below the set level in the valve 2066 and consequently the valve 2066 will then close permanently (unless a blockage of the conduits 12, 24 or filters 26 is cleared). As gaseous fluid flow rate continues to fall the pressure monitored by sensor 2060 will fall and eventually approach that sensed by sensor 2062 until the stored pressure differential value in the control system memory is reached which signals to the control system 60 that the alarm be activated.

Figure 20F:
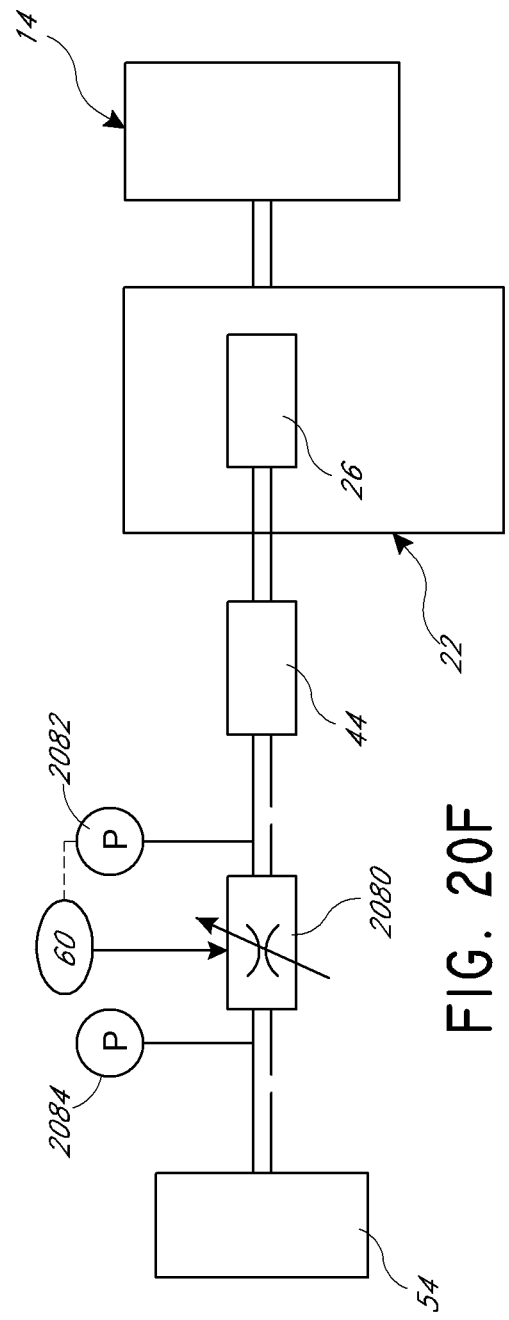

FIG. 20F shows a sixth embodiment where the fixed aperture fluid flow restrictor of previous embodiments is replaced by a variable area aperture flow restrictor 2080. In this embodiment an objective is to reduce or minimize any undue or unnecessary burden or load on the pump 44 as with the embodiment of FIG. 20F. Similarly, when there is no blockage of any kind and fluid flow is relatively high and unrestricted a small restriction places an unnecessary burden on the pump rendering it inefficient in operation. Therefore, in this embodiment, the first pressure sensor 2082 downstream of the pump 44 and upstream of the variable restrictor 2080 is electrically connected to the control system 60. When the pressure sensed by sensor 2082 exceeds a stored value in the control system memory, for example, greater than +5 mm Hg, the control system signals the variable aperture flow restrictor 2080 to increase the aperture area therein and so reduce the load or burden on the pump 44. The variable area flow restrictor 2080 may be a proportional device where the aperture area is proportional to the pressure sensed at the pressure sensor 2082 or may be a step device where the area is changed in predetermined increments or decrements according to the pressure sensed. As fluid flow in the apparatus falls due to a blockage or full canister the pressure sensed by sensor 2082 falls to a level below that stored in the control system memory and the area of the aperture in the variable area flow restrictor is reduced to a lower, predetermined area. As gaseous fluid flow continues to fall the pressure in the first sensor 2082 falls and approaches that sensed by a second sensor 2084 downstream of the variable area flow restrictor 2080. As in previous embodiments when fluid flow deteriorates sufficiently, signals from the two pressure sensors 2082, 2084 to the control system 60 eventually result in an alarm being activated.

Figure 21:
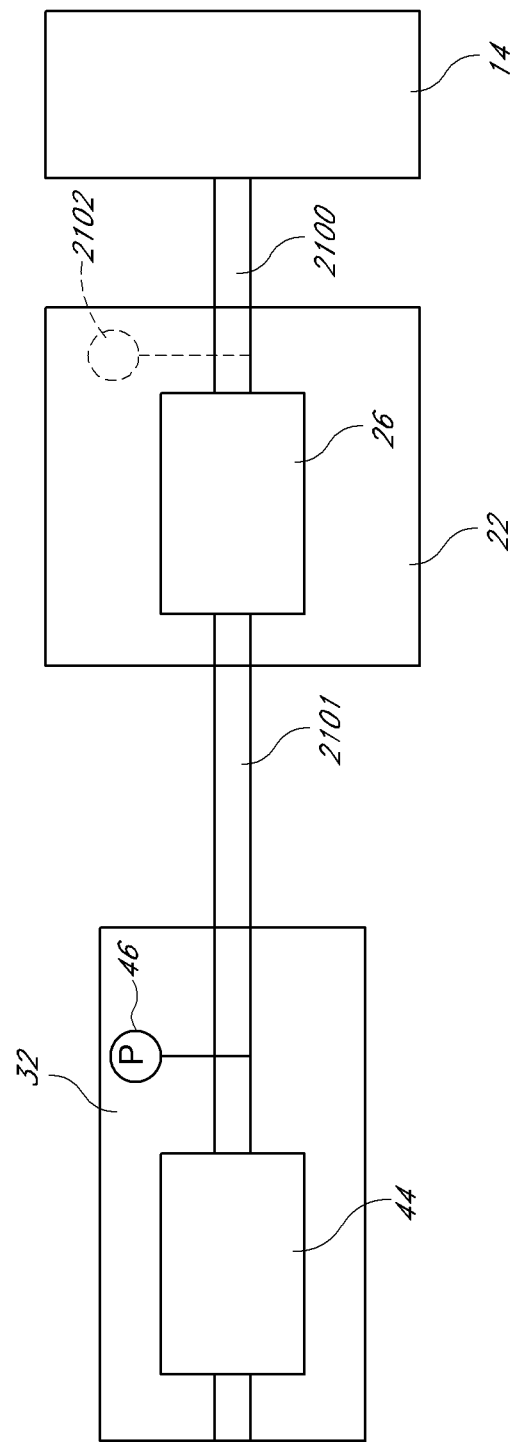
FIG. 21 illustrates part of a TNP system.

FIG. 21 illustrates schematically a TNP system. A more thorough discussion of many of the parts shown has been made previously with respect to FIG. 1. It is to be noted that a connecting tube 2100 is illustrated as connecting the dressing 14 to the canister 22 whilst a further connecting tube 2101 is illustrated connecting the canister to the aspirant system 32. These tubes are shown for illustrative purposes and it will be appreciated that rather than the tubes connector portions 34, 36 can be utilized between the aspirant system and canister and that likewise an inline connector 16 may be connected between the dressing and canister.

An aspirant pump 44 used to create the negative pressure of the TNP system is a diaphragm pump. This is utilized to move air and create the vacuum in the wound bed. The diaphragm acts as a miniature piston and, hence creates small pulses of pressure as it moves backwards and forwards. These pulses interfere with the flow of air through the system and their magnitude as measured, for example at the pump inlet, varies according to the status of the canister. This relationship is illustrated more clearly in FIG. 22. It will be appreciated that other types of pump providing a pulsatile output can be used according to other embodiments.

Figure 22:
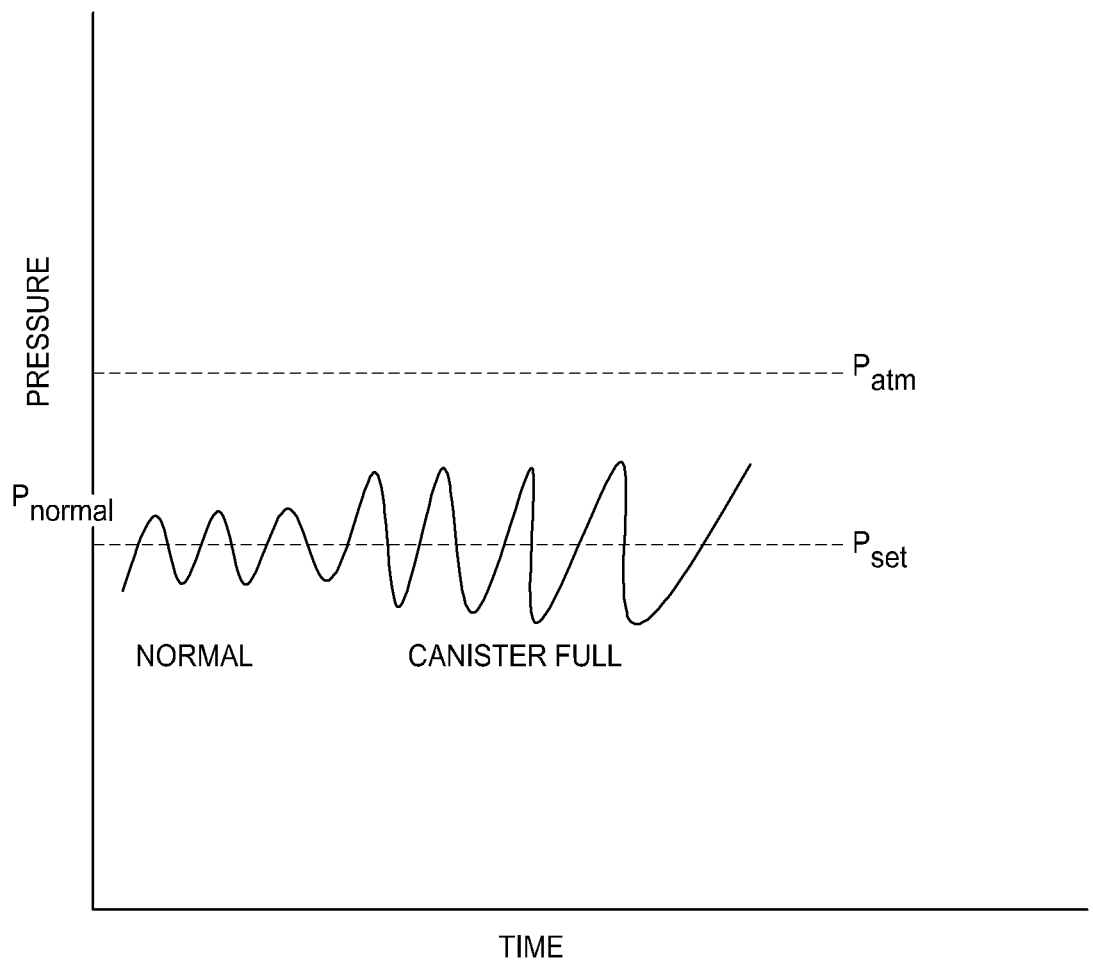
FIG. 22 illustrates how magnitude and/or frequency of pulses can vary.

As shown in FIG. 22 during a normal mode of operation the pressure pulses have relatively small magnitude centered around a pre-set pressure $P_{set}$. A maximum value of these pressure pulse readings $P_{normal}$ can thus be utilized to determine when a pump is working efficiently.

Thus by measuring the magnitude of the pressure pulses it is possible to detect whether a canister is blocked. FIG. 22 also illustrates operation with a canister filter full. Whilst the negative pressure delivered by the pump remains less than atmospheric pressure $P_{atm}$ the magnitude of the pulses is shown as later increased substantially above the predetermined normal operating pressure $P_{normal}$. It will also be appreciated that minimum pressure values taken at the minimum of the pressure curve or some other common sampling point could be utilized and compared as a predetermined set value. FIG. 22 thus illustrates how during a normal mode of operation the flow path provided by the tubing 2100, canister 22, tubing 2100 and tubing in the aspirant system provides a sufficiently large volume so that pulsatile elements of pressure variation caused by the diaphragm of the pump are moderated but still are detectable. When a canister filter 26 becomes full the flow path volume 'seen' by the aspirant pump is much diminished and includes the volume only of the tubing 2101 and tubing elements in the aspiration system. As such the pulsatile elements associated with the pumping pressure are 'magnified'.

It will also be appreciated that the frequency of pumping may also vary when a canister filter becomes full. The frequency can thus likewise additionally or optionally be utilized to determine status of at least one parameter such as fullness or leakiness associated with a canister of a TNP system.

Rather than initiating an alarm when the canister filter is full, the magnitude or frequency characteristics of the pressure can also be continually or periodically monitored with a magnitude being used to indicate current status. This can continually provide an indication such as percentage fullness which may be displayed via a user interface.

It will be appreciated that aptly the pressure is measured close to the location where the aspirant pump is provided in a TNP system. This is because damping effects caused by the volume of air in the flow path are minimized close to the pump inlet.

Figure 23:
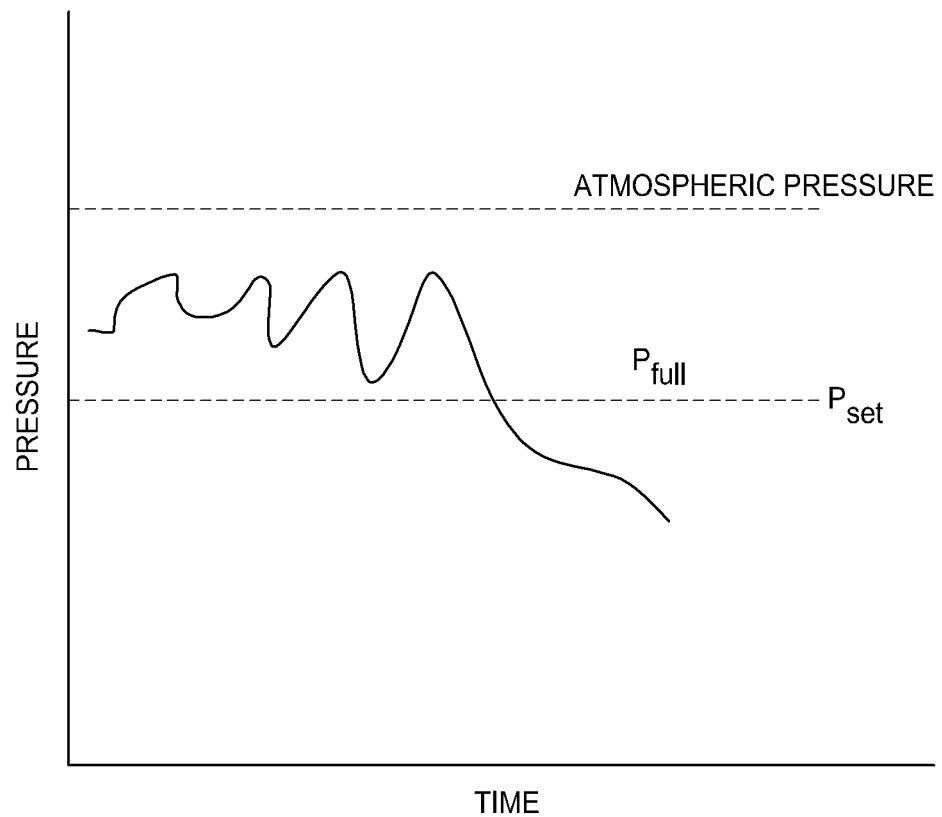
FIG. 23 illustrates pressure with a blocked canister filter.

FIG. 23 illustrates how some embodiments can utilize an optional pressure sensor 2102 to monitor pressure at a location downstream of a canister filter 26 between the filter and dressing 14. As illustrated in FIG. 23 due to the substantial volume of the flow path during normal operation at the pressure sensor 2102 the pulsatile effects on pressure are muffled somewhat. However as a canister filter fills the result is a blockage in the flow path. The sensor 2102 thus no longer measures any pulse like flow from the pump. When this measured pressure falls below a predetermined threshold value $P_{SET}$ an alarm in the form of an audible and/or visual cue can be initiated.

Some embodiments thus provide a manner in which the status of a canister such as a fullness of a filter associated with a canister can be determined by monitoring pressure provided by a pump of a TNP system. By determining a characteristic such as magnitude or frequency associated with the monitored pressure the status of at least one parameter such as fullness or a leak in a flow path associated with a canister can be determined. This can be achieved with only a single pressure sensor which obviates the need associated with prior known devices for two pressure sensors.

Some embodiments can utilize a single pressure sensor downstream of a canister filter between a canister filter and a dressing of a TNP system to determine when a canister filter is full and needs replacing.

Some embodiments can make use of two pressure sensors. One pressure sensor is located proximate to a pump inlet whilst a further pressure sensor is located downstream of a canister filter. This enables prompt detection of a leak and/or full canister filter.

Referring now to FIGS. 24 to 27 and where the same or similar features are denoted by common reference numerals. Reference to FIGS. 1 to 4 may also be made in the following description.

FIG. 24 shows a schematic diagram of an embodiment of apparatus 2400. The apparatus includes an aspiration conduit 12, 24 connected to a dressing 14; the aspiration conduit 24 being connected to a waste canister 22 having a filter 26 adjacent an outlet port 28; a device which houses an aspirant pump 44 and a control system (not shown in FIG. 24 but see 60 in FIGS. 1 to 4). The device has a pressure sensor 2402 at a position upstream of the pump 44 and in between the pump 44 and the outlet port 28 of the waste canister 22, the waste canister and pump being connected by tubing 2408 forming part of the aspirant fluid flow path. A flowmeter 48 is provided downstream of the pump 44 (but may, however, be sited upstream of the pump between the waste canister and pump). Downstream of the waste canister outlet port 28 the fluid flow is gaseous as all liquid and bacteria is retained in the canister by the filters 26 (see also 282 in FIG. 9), the pressure sensor 2402 being sited in this gaseous fluid flow region. The canister is also provided with a relief conduit 2404 having a selectable valve 2406, such as a solenoid valve, for example, therein which is able to open the relief line 2404 to atmosphere (note that access of air to the waste canister through the line 2404 and valve 2406 is directly thereto and not via the filters 26 in the waste canister), the relief line 2404 having a separate filter 2409 therein to prevent ejection of any waste matter or bacteria to the atmosphere when the valve 2406 is open. The selectable valve 2406 is electrically connected to the control system 60 which is able to open and close the valve in response to pressure signals from the sensor 2402. In response to the device control system 60 sensing a full canister or filter blockage or such, due to the fluid flow rate sensed by the flowmeter 48 decreasing below a stored value in the control system memory, the control system 60 opens the valve 2406 to allow air to flow into the interior of the waste canister since the waste canister interior is connected to the vacuum pump as it is part of the fluid flow path and the pressure therein is negative with respect to ambient air pressure. If the canister 22 is full the effect that the airflow into the canister will have on the flowmeter 48 (see FIGS. 1 to 4) in the fluid flow path will be relatively small and the control system will interpret this as a canister full condition and activate an appropriate alarm to the user. If, however, the opening of the valve 2406 results in normal fluid flow rate resuming then this is interpreted by the control system as a blocked or otherwise closed-off aspirant conduit since the inflow of air via the valve 2406 will immediately restore normal fluid flow rate as sensed by the flowmeter 48. In this latter case the control system will activate an alarm appropriate to a blocked conduit condition.

Sample pseudocode for a system incorporating the relief conduit 2404 and valve 2406 with pressure and flow measurement for blockage detection is given below:

```
Procedure Blockage_Detection
    Measure current flow = F_cur
    Measure current pressure = p_cur
    if F_cur < min_flow_needed
    and if p_cur - p_set < allowable_pressure_difference_limit
            filter_blocked = true
        else
            filter_blocked = false
    end if
    if (filter_blocked == true)
        Open relief line valve
        Wait
        Measure current pressure = p_new
        if p_new = P_cur
            convey canister full
        else
            convey blockage in tubing
        endif
    endif
End Procedure Blockage_Detection
```

As will be known to those skilled in the control system art, the steps recited above may be repeated by the control system software at predetermined intervals all the time the TNP apparatus is in use.

FIG. 25 shows a schematic diagram of an embodiment of apparatus and corresponds to the method according to some embodiments. Again, reference is also made to FIGS. 1 to 4. In this embodiment 2520 a second pressure sensor 2522 is situated so as to be able to monitor the pressure inside the waste canister upstream of the filters 26. The control system 60 monitors and compares the pressure readings from sensors 2502 and 2522, the level of pressure differential indicating the type of blockage which exists. If the pressure differential is low relative to a stored value or value range in the control system memory then the control system interprets this as a blocked aspirant conduit since the vacuum level in the canister is comparable to that at the pump inlet. If the pressure differential is larger than the stored value or value range in the control system memory, then the control system interprets this as a blocked filter in the canister due to the canister being full and unable to maintain the vacuum. The control system activates the appropriate alarm to the user whichever condition pertains. In this embodiment the flowmeter 48 of the first embodiment may not be needed and may be dispensed with to reduce cost.

Sample pseudocode for a system incorporating the differential pressure measurement method for blockage detection is given below:

```
Define p_full = pressure for canister full (filter blocked)
Define p_blockage = pressure for blockage between wound and
    canister
Procedure Blockage_Detection
Measure current pressure P1 = P1
Measure current pressure P2 = P2
If P1 - P2 ≤ p_blockage
    filter_blocked = true
else
    filter_blocked = false
end if
if P1 - P2 ≥ p_full
    tube_blocked = true
        else
    tube_blocked = false
end if
End Procedure Blockage_Detection
```

Figure 26A:
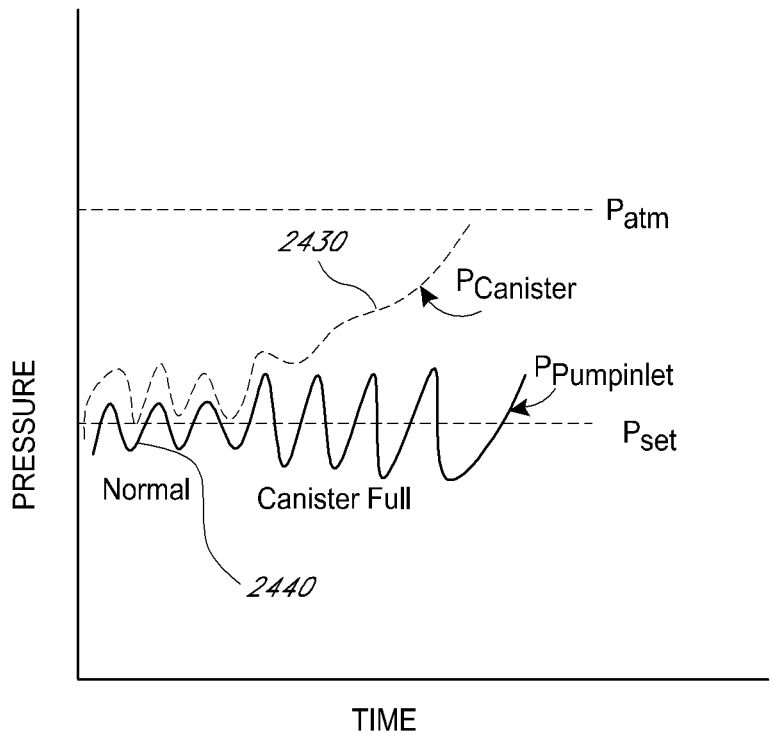
FIGS. 26A and 26B show graphs of sample pressure readings from two pressure sensors in connection with determining the cause of a blockage.
Figure 26B:
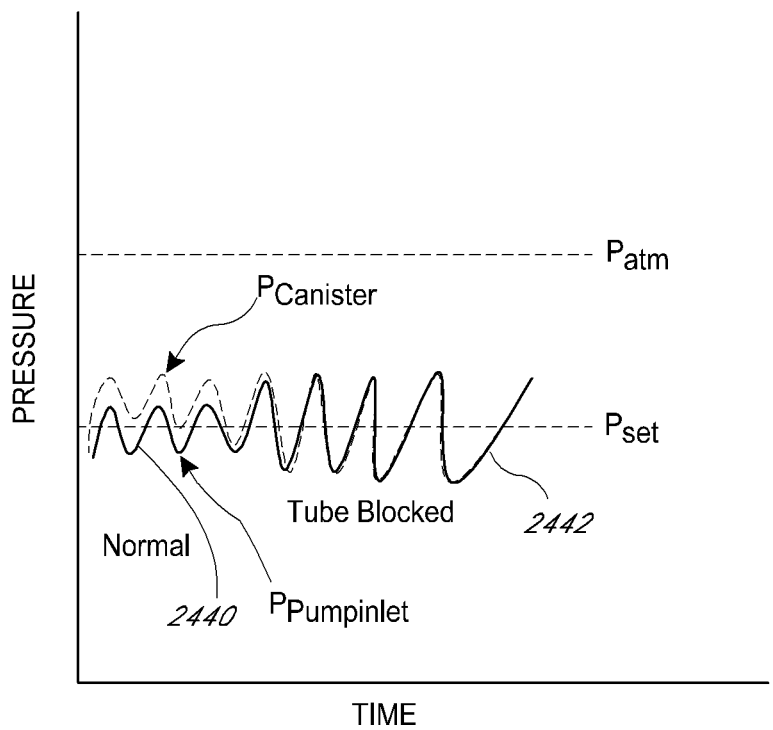

FIGS. 26A and 26B show graphs giving sample readings from the two sensors 2402, 2422. The solid line labeled "Ppumpinlet" indicates the pressure readings from sensor 2402 and the broken line labeled "Pcanister" indicates the pressure readings from sensor 2422. The graph indicates "Pset" which is the value or tolerance range stored in the control system memory and "Patm" which is ambient atmospheric pressure outside the canister. Under normal operating conditions, i.e. when there is no blockage of any kind, the canister being less than full and the aspirant conduit 12, 24 being open to unimpeded flow other than to usual viscosity effects and conduit interaction with the flowing fluid, the pressure monitored at the first pressure sensor 2402 is at or about a preset value 2440 to apply vacuum to the wound site/dressing 14 and, the pressure sensed by the second sensor 2422 is at a lower negative pressure due to the pressure drop caused by the filter 26. The pressure differential between sensors 2402 and 2422 may be about +20 mmHg, for example, when the apparatus is operating normally. When pressure Pcanister rises above a pre-stored tolerance level as at 2430 then the control system interprets this as a canister full condition. In contrast to this, and as shown in the graph of FIG. 26B, when the aspirant conduit is blocked the normal pressure difference of about +20 mmHg falls further and the first and second pressures converge towards each other as at 2442 and the control system recognizes this as a blocked aspirant conduit condition and activates an appropriate alarm.

Figure 27:
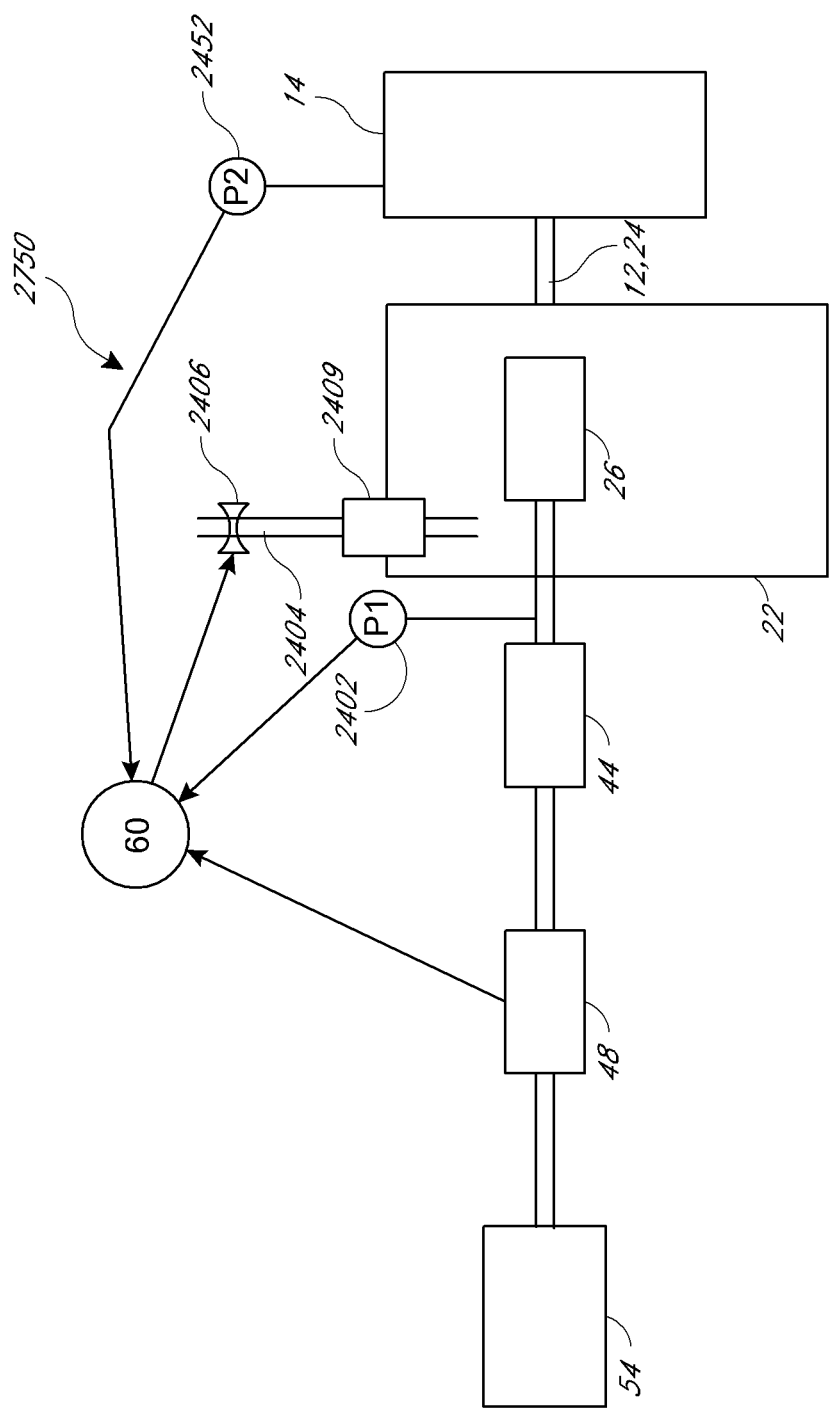
FIG. 27 shows a modified embodiment of the apparatus for the application TNP therapy shown in FIG. 10.

FIG. 27 shows a modified embodiment 2750 similar to that shown and described with reference to FIG. 24. However, in this modified embodiment a second pressure sensor 2452 is provided, both the first second pressure sensors 2402 and 2452 and the flowmeter 48 being in electrical connection to the control system 60 for transmitting signals thereto. The control system 60 is also electrically connected to the valve 2406 for opening and closing thereof. In this embodiment the control system 60 monitors the pressures from the sensors 2402 and 2452 and when the pressure differential exceeds a stored value in the control system memory by a greater negative amount the control system opens the valve 2406 to admit ambient air to the waste canister 22. Depending upon the effect of the admitted air on the fluid flow rate sensed by the flowmeter 48 the control system determines the cause of the blockage as in the description with reference to FIG. 24.

Throughout the description and claims of this specification, the words "comprise" and "contain" and variations of the words, for example "comprising" and "comprises," means "including but not limited to," and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Throughout the description and claims of this specification, certain aspects, advantages and novel features have been described herein. It is to be understood that not necessarily all such advantages can be achieved in accordance with any particular embodiment disclosed herein. Thus, the disclosure described herein can be embodied or carried out in a manner that achieves or optimizes one advantage or a group of advantages as taught herein without necessarily achieving other advantages as can be taught or suggested herein.

Features, integers, characteristics, compounds, chemical moieties or groups described in conjunction with a particular aspect, embodiment or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of the disclosure. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Depending on the embodiment, certain of the steps described above may be removed, others may be added. For instance, the various components illustrated in the figures may be implemented as software and/or firmware on a processor, controller, ASIC, FPGA, and/or dedicated hardware. Furthermore, the features and attributes of the specific embodiments disclosed above may be combined in different ways to form additional embodiments, all of which fall within the scope of the present disclosure.

Although the present disclosure provides certain preferred embodiments and applications, other embodiments that are apparent to those of ordinary skill in the art, including embodiments which do not provide all of the features and advantages set forth herein, are also within the scope of this disclosure. Certain embodiments are encompassed in the appended claims.

What is claimed is:

1. A negative pressure wound therapy apparatus comprising:
    a negative pressure source configured to be fluidically connected to a wound covered by a wound dressing and to aspirate fluid from the wound;
    a fluid flow path configured to transfer fluid from the wound toward the negative pressure source, the fluid flow path comprising:
        a first conduit configured to restrict a flow of fluid passing through the first conduit;
        at least one pressure sensor configured to measure a pressure differential in at least a portion of the first conduit; and
        a second conduit connected in parallel with the first conduit and configured to enable a higher flow of fluid through the second conduit than through the first conduit, the second conduit comprising a valve configured to:
            in an open state, direct the flow of fluid caused by operation of the negative pressure source through the second conduit and not through the first conduit, and
            in a closed state, block the flow of fluid through the second conduit and direct the flow of fluid caused by operation of the negative pressure source through the first conduit; and
    a controller programmed to provide indication of a blockage in the fluid flow path in response to the pressure differential measured by the at least one pressure sensor satisfying a first pressure threshold.

2. The apparatus of claim 1, wherein the valve is configured to transition into the open state in response to pressure in the second conduit not satisfying a second pressure threshold and transition into the closed state in response to the pressure in the second conduit satisfying the second pressure threshold, the second pressure threshold being associated with a low flowrate of fluid.

3. The apparatus of claim 1, wherein the first pressure threshold is associated with ambient pressure.

4. The apparatus of claim 1, wherein a diameter of the first conduit is between 0.1 mm and 0.5 mm.

5. The apparatus of claim 1, further comprising a canister configured to store at least some of the fluid aspirated from the wound.

6. The apparatus of claim 5, further comprising another valve in communication with the canister and configured to admit air into the canister, wherein the controller is further programmed to:
    determine a first fluid flow level in the fluid flow path when the another valve is closed;
    open the another valve in response the first fluid flow level satisfying a fluid flow threshold indicative of the blockage in the fluid flow path or the canister being full;
    determine a second fluid flow level after opening the another valve; and
    provide an indication of one of the blockage in the fluid flow path or the canister being full based on the second fluid flow level.

7. A kit comprising the apparatus of claim 1 and the wound dressing.

8. The apparatus of claim 1, wherein:
responsive to the valve being in the open state, the flow of fluid is directed through the second conduit and is not restricted, and
responsive to the valve being in the closed state, the flow of fluid is directed through the first conduit and is restricted.

9. The apparatus of claim 1, wherein the valve is configured to automatically open and close in response to a pressure in the second conduit.

10. The apparatus of claim 1, wherein the at least one pressure sensor comprises a differential pressure sensor.

11. The apparatus of claim 1, wherein the at least one pressure sensor comprises a first pressure sensor and a second pressure sensor positioned downstream of the first pressure sensor.

12. A method of operating a negative pressure wound therapy apparatus, the method comprising:
aspirating fluid from a wound covered by a wound dressing via a fluid flow path configured to transfer fluid from the wound toward a negative pressure source of the negative pressure wound therapy apparatus;
opening a valve positioned in an unrestricted portion of the fluid flow path and causing fluid to flow through the unrestricted portion of the fluid flow path, wherein fluid is caused to flow as a result of operation of the negative pressure source;
closing the valve and causing fluid to flow through a restricted portion of the fluid flow path, wherein a rate of fluid flow through the restricted portion of the fluid flow path is lower than a rate of fluid flow through the unrestricted portion of the fluid flow path; and
providing indication of a blockage in the fluid flow path in response to a pressure differential in the restricted portion of the fluid flow path satisfying a first pressure threshold.

13. The method of claim 12, wherein closing the valve is performed in response to pressure in the unrestricted portion of the fluid flow path satisfying a second pressure threshold indicative of a low flowrate of fluid.

14. The method of claim 13, further comprising opening the valve and causing the fluid to flow through the unrestricted portion of the fluid flow path in response to the pressure in the unrestricted portion of the fluid flow path no longer satisfying the second pressure threshold.

15. The method of claim 12, wherein the first pressure threshold is indicative of ambient pressure.

16. The method of claim 12, wherein the valve is configured to automatically open and close in response to a pressure in the unrestricted portion of the fluid flow path.

17. The method of claim 12, wherein the pressure differential in the restricted portion of the fluid flow path is measured by a differential pressure sensor.

18. The method of claim 12, wherein the pressure differential in the restricted portion of the fluid flow path is measured by a pair of pressure sensors.

19. The method of claim 12, further comprising storing at least some fluid aspirated from the wound in a canister.

20. The method of claim 12, wherein the unrestricted portion of the fluid flow path is connected in parallel with the restricted portion of the fluid flow path.

* * * * *